(12) United States Patent
Medina-Kauwe

(10) Patent No.: US 10,793,853 B2
(45) Date of Patent: Oct. 6, 2020

(54) TARGETED DELIVERY SYSTEM

(75) Inventor: Lali K. Medina-Kauwe, Porter Ranch, CA (US)

(73) Assignee: CEDARS-SINAI MEDICAL CENTER, Los Angeles, CA (US)

( * ) Notice: Subject to any disclaimer, the term of this patent is extended or adjusted under 35 U.S.C. 154(b) by 115 days.

(21) Appl. No.: 13/189,265

(22) Filed: Jul. 22, 2011

(65) Prior Publication Data
US 2012/0004181 A1  Jan. 5, 2012

Related U.S. Application Data

(63) Continuation-in-part of application No. PCT/US2010/021830, filed on Jan. 22, 2010.

(60) Provisional application No. 61/147,037, filed on Jan. 23, 2009.

(51) Int. Cl.
C07K 14/005 (2006.01)
C12N 15/11 (2006.01)

(52) U.S. Cl.
CPC .......... *C12N 15/111* (2013.01); *C07K 14/005* (2013.01); *C07K 2319/035* (2013.01); *C12N 2310/14* (2013.01); *C12N 2320/32* (2013.01); *C12N 2710/10322* (2013.01)

(58) Field of Classification Search
None
See application file for complete search history.

(56) References Cited

U.S. PATENT DOCUMENTS

| | | | |
|---|---|---|---|
| 5,439,829 | A | 8/1995 | Anderson et al. |
| 5,559,009 | A | 9/1996 | Wickham et al. |
| 5,885,808 | A | 3/1999 | Spooner et al. |
| 6,084,083 | A | 7/2000 | Levinson et al. |
| 6,270,747 | B1 | 8/2001 | Nadel et al. |
| 6,287,792 | B1 | 9/2001 | Pardridge et al. |
| 6,333,396 | B1 * | 12/2001 | Filpula et al. ............. 530/387.3 |
| 6,339,070 | B1 | 1/2002 | Emery et al. |
| 9,078,927 | B2 | 7/2015 | Medina-Kauwe |
| 2001/0055783 | A1 | 12/2001 | Allnutt et al. |
| 2003/0138432 | A1 | 7/2003 | Glazier |
| 2003/0170836 | A1 | 9/2003 | Rabinovich |
| 2005/0042753 | A1 | 2/2005 | Yang et al. |
| 2005/0048606 | A1 | 3/2005 | Wang et al. |
| 2006/0014712 | A1 | 1/2006 | Neuman |
| 2006/0093674 | A1 | 5/2006 | Slobodkin et al. |
| 2006/0178334 | A1 * | 8/2006 | Rossi ................... C12N 15/111 514/44 A |
| 2008/0234183 | A1 | 9/2008 | Hallbrink et al. |
| 2010/0331273 | A1 | 12/2010 | Medina-Kauwe |
| 2014/0335025 | A1 | 11/2014 | Medina-Kauwe |
| 2015/0240231 | A1 | 8/2015 | Medina-Kauwe |
| 2016/0008481 | A1 | 1/2016 | Medina-Kauwe |
| 2016/0060316 | A1 | 3/2016 | Medina-Kauwe et al. |
| 2016/0331840 | A1 | 11/2016 | Medina-Kauwe |
| 2017/0281802 | A1 | 10/2017 | Medina-Kauwe |
| 2018/0028678 | A1 | 2/2018 | Medina-Kauwe |

FOREIGN PATENT DOCUMENTS

| | | |
|---|---|---|
| WO | 2002062823 | 8/2002 |
| WO | WO-2002/094318 A1 | 11/2002 |
| WO | WO 2008/017473 * | 2/2008 |
| WO | 2009009441 | 1/2009 |
| WO | 2010085665 | 7/2010 |

OTHER PUBLICATIONS

Medina-Kauwe ('Targeting siRNA missiles to her2+ breast cancer' Jun. 2007 13 pages, retrieved from http://www.dtic.mil/cgi-bin/GetTRDoc?AD=ADA472023 on Aug. 13, 2013).*
Agadjanian et al ('Modified viral capsid protein mediates non-viral targeting of unique non-covalent drug conjugates to HER2+ breast cancer cells' Proceedings of the AACR Annual Meeting v48 p. 357 Apr 14-18, 2007, printed as 2 pages).*
Sawai et al ('Impact of single-residue mutations on the structure and function of ovispirin/novispirin antimicrobial peptides' Protein engineering 2002 v15(3) pp. 225-232, printed as 19 pages).*
Translation of SEQ ID No. 1 (retrieved from http://www.biochem.ucl.ac.uk/cgi-bin/mcdonald/cgina2aa.pl on Sep. 1, 2015, 4 pages).*
Year of publication (retrieved from http://rep945.infoeach.com/view-OTQ1fDgzNDY1NQ==.html on Sep. 1, 2015, 2 pages).*
Chen et al. ('Growth inhibition of human breast carcinoma and leukemia/lymphoma cell lines by recombinant interferon-beta2' PNAS v85 Nov. 1988 pp. 8037-8041).*
Poeck et al. ('5'-triphosphate-siRNA: turning gene silencing and Rig-I activation against melanoma' Nature Medicine v14(11) Nov. 2008 pp. 1256-1263).*
Morrissey et al. ('Potent and persistent in vivo anti-HBV activity of chemically modified siRNAs' Nature Biotechnology v23(8) Aug. 2005 pp. 1002-1007).*
Aris et al. ('Modular protein engineering for non-viral gene therapy' Trends in Biotechnology v22(7) Jul. 2004 pp. 371-377). (Year: 2004).*
Agadjanian et al., Specific delivery of corroles to cells via noncovalent conjugates with viral proteins. (2006) Pharm. Res. 23;367-377.
Baselga, J. et al., Phase II study of weekly intravenous recombinant humanized anti-p185HER2 monoclonal antibody in patients with HER2/neu-overexpressing metastatic breast cancer. (1996) J. Clin. Oncol., 14(3):737-44, Abstract only.
Braslawsky, G.R. et al., Antitumor activity of adriamycin (hydrazone-linked) immunoconjugates compared with free adriamycin and specificity of tumor cell killing. (1990) Cancer Res., 50, 6608-6614.
Chester, K.A. et al., Clinical applications of phage-derived sFvs and sFv fusion proteins, (2000) Disease Markers 16 (1-2);53-62, Abstract only.

(Continued)

Primary Examiner — Ronald T Niebauer
(74) Attorney, Agent, or Firm — Morrison & Foerster LLP

(57) ABSTRACT

The present invention relates a targeted delivery system for siRNA or antisense technology. In one embodiment, the invention provides for a method of treating cancer by administering a therapeutically effective dosage of Her-PBK10 combined with siRNA, resulting in the inhibition of Her2 expression and cell death. In another embodiment, a plurality of HerPBK10 combined with siRNA form a nanoparticle.

18 Claims, 31 Drawing Sheets
Specification includes a Sequence Listing.

(56) References Cited

OTHER PUBLICATIONS

Choudhury, A. et al., Small interfering RNA (siRNA) inhibits the expression of the Her2/neu gene, upregulates HLA class I and induces apoptosis of Her2/neu positive tumor cell lines. (2004) International Journal of Cancer 108, 71-77.
Denny, DNA-Intercalating ligands as anti-cancer drugs: prospects for future design, Anticancer Drug Des. 1989, vol. 4 (4); 241-63. Abstract only.
Drummond, D.C. et al., Optimizing liposomes for delivery of chemotherapeutic agents to solid tumors. (1999) Pharmacol. Rev., 51(4); 691-743.
Faltus, T. et al., Silencing of the HER2/neu gene by siRNA inhibits proliferation and induces apoptosis in HER2/neu-overexpressing breast cancer cells. (2004) Neoplasia 6(6);786-795.
Fisher, K.J. et al., The transmembrane domain of diphtheria toxin improves molecular conjugate gene transfer. (1997) Biochemical Journal 321;49-58.
Frankel, A.E. et al., Targeted toxins. (2000) Clinical Cancer Research 6:326-334.
Glockshuber, R. et al., A comparison of strategies to stabilize immunoglobulin Fv-fragments. (1990) Biochemistry 13;29(6):1362-7, Abstract only.
Goren, D. et al., Targeting of stealth liposomes to erbB-2 (Her/2) receptor: in vitro and in vivo studies. (1996) Br. J. Cancer 74:1749-1756.
Jeschke, M. et al., Targeted inhibition of tumor-cell growth by recombinant heregulin-toxin fusion proteins. (1995) International Journal of Cancer 60(5);730-9, Abstract only.
Kim et al., Interferon Induction by siRNA's and ssRNAs synthesized by phage polymerase. (2004) Nature Biotechnology, vol. 22(3);321-325.
Kute, T. et al., Development of Herceptin resistance in breast cancer cells. (2004) Cytometry Part A 57A:86-93, Abstract only.
Medina-Kauwe et al., Using GFP-ligand fusions to measure receptor-mediated endocytosis in living cells. (2002) Vitamins and Hormones, vol. 65;81-95, Abstract only.
Medina-Kauwe et al., 3PO, a novel non-viral gene delivery system using engineered Ad5 penton proteins. (2001) Gene Therapy 8;795-803.
Medina-Kauwe et al., Assessing the Binding and Endocytosis Activity of Cellular Receptors Using GFP-Ligand Fusions. (2000) BioTechniques 29, Abstract only.
Medina-Kauwe et al., Non-viral gene delivery to human breast cancer cells by targeted Ad5 penton proteins. (2001) Gene Therapy 8;1753-1761.
Medina-Kauwe et al., Intracellular trafficking of nonviral vectors. (2005) Gene Therapy 12;1734-1751.
Minotti, G. et al., Anthracyclines: molecular advances and pharmacologic developments in antitumor activity and cardiotoxicity. (2004) Pharmacol. Rev., vol. 56(2);185-229.
Siwak et al., The Potential of drug-carrying immunoliposomes as Anticancer Agents. (2002) Clin. Cancer Res., 8: 955-956.
Schmidt, M. et al., Suppression of metastasis formation by a recombinant single chain antibody-toxin targeted to full-length and oncogenic variant EGF receptors. (1999) Oncogene 18, 1711-1721.
Slamon, D.J. et al., Use of chemotherapy plus a monoclonal antibody against HER2 for metastatic breast cancer that overexpresses HER2. (2001) N Engl J Med 344, 783-792.
Trail, P.A. et al., Monoclonal antibody drug immunoconjugates for targeted treatment of cancer. (2003) Cancer Immunol. Immunother. 52(5):328-37, Abstract only.
Trail, P.A. et al., Antigen-specific activity of carcinoma-reactive BR64-doxorubicin conjugates evaluated in vitro and in human tumor xenograft models. (1992) Cancer Res., 52;5693-5700.
Trail, P.A. et al., Cure of xenografted human carcinomas by BR96-doxorubicin immunoconjugates. (1993) Science 261 (5118); 212-215, Abstract only.

Vogel, C.L. et al., Efficacy and safety of trastuzumab as a single agent in first-line treatment of HER2-overexpressing metastatic breast cancer. (2002) J. Clin. Oncol. 20(3):719-26, Abstract only.
Zabner, J. et al., Cellular and molecular barriers to gene transfer by a cationic lipid. (1995) Journal of Biological Chemistry 270(32);18997-19007.
U.S. Appl. No. 12/667,436 Restriction Requirement dated Feb. 21, 2012, 11 pages.
U.S. Appl. No. 12/667,436 Non-final Office Action dated Aug. 14, 2012, 12 pages.
PCT/US08/69239 International Search Report and Written Opinion dated Jan. 28, 2009, 14 pages.
PCT/US08/69239 International Report on Patentability dated Jan. 12, 2010, 9 pages.
PCT/US2010/021830 International Search Report and Written Opinion dated Jul. 15, 2010, 12 pages.
PCT/US2010/021830 International Preliminary Report on Patentability dated Jul. 26, 2011, 6 pages.
U.S. Appl. No. 12/667,436—US Final Office Action dated Feb. 28, 2013, 20 pages.
Agadjanian et al. (2009). "Tumor detection and elimination by a targeted gallium corrole", Proc Natl Acad Sci USA, vol. 106, pp. 6105-6110.
Goldman et al. (1990). "Heterodimerization of the erbB-1 and erbB-2 receptors in human breast carcinoma cells: a mechanism for receptor transregulation", Biochemistry, vol. 29, pp. 11024-11028.
Medina-Kauwe et al. (2002). "A Novel Gene Delivery System Targeted to Breast Cancer", U.S. Army Medical Research and Material Command Fort Detrick, Maryland, pp. 1-14.
Rentsendorj et al. (2006). "Typical and atypical trafficking pathways of Ad5 penton base recombinant protein: implications for gen transfer", Gen. Ther., vol. 13, pp. 821-836.
Sepp-Lorenzino et al. (1996). "Signal transduction pathways induced by heregulin in MDA-MB-453 breast cancer cells", Oncogene, vol. 12, pp. 1679-1687.
Sliwkowski et al. (1994). "$3^{rd}$ Coexpression of erbB2 and erbB3 proteins reconstitutes a high affinity receptor for heregulin", Journal of Biological Chemistry, vol. 269, pp. 14661-14665.
Medina-Kauwe (2008). "Targeting Sirna Missiles to Her2+ Breast Cancer", U.S. Army Medical Research and Material Command Fort Detrick, Maryland, pp. 1-10.
Medina-Kauwe (2009). "Targeting SiRNA Missiles to Her2+ Breast Cancer", U.S. Army Medical Research and Material Command Fort Detrick, Maryland, pp. 1-12.
Baselga, J et al. (Mar. 1996). "Phase II Study of Weekly Intravenous Recombinant Humanized Anti-p185$^{HER2}$ Monoclonal Antibody in Patients With HER2/Neu-Overexpressing Metastatic Breast Cancer," J. Clin. Oncol. 14(3):737-744.
Chester, K.A. et al. (2000). "Clinical applications of Phage-Derived sFvs and sFv Fusion Proteins," Disease Markers 16(1-2):53-62.
Cobleigh, M.A. et al. (1998). "Efficacy and Safety of Herceptin™ (Humanized Anti-HER2 Antibody) As a Single Agent in 222 Women With HER2 Overexpression Who Relapsed Following Chemotherapy for Metastatic Breast Cancer," Proc. Am. Soc. Clin. Oncol. 17:97a.
David, J.M. et al. (2016). "The IL-8/IL-8R Axis: A Double Agent in Tumor Immune Resistance," Vaccines 4(22):1-15.
Denny, (1989). "DNA-Intercalating Ligands As Anti-Cancer Drugs: Prospects for Future Design," Anticancer Drug Des. 4(4):241-263.
Glockshuber, R. et al. (1990). "A Comparison of Strategies to Stabilize Immunoglobulin $F_v$-Fragments," Biochemistry 29(6):1362-1367.
Jeschke, M. et al. (1995), "Targeted Inhibition of Tumor-Cell Growth by Recombinant Heregulin-Toxin Fusion Proteins," International Journal of Cancer 60(5):730-739.
Kute, T. et al. (2004). "Development of Herceptin Resistance in Breast Cancer Cells," Cytometry Part A 57A:86-93.
Medina-Kauwe, L.K. et al. (Sep. 2000). "Assessing the Binding and Endocytosis Activity of Cellular Receptors Using GFP-Ligand Fusions," Bio Techniques 29:602-609.
Medina-Kauwe, L.K. et al. (2002). "Using GFP-Ligand Fusions to Measure Receptor-Mediated Endocytosis in Living Cells'" Vitamins and Hormones 65:81-95.

(56) References Cited

OTHER PUBLICATIONS

Park, J.W. et al. (Apr. 2002). "Anti-HER2 Immunoliposomes: Enhanced Efficacy Attributable to Targeted Delivery," *Clin. Cancer Res.* 8:1172-1181.

Trail, P.A. et al. (Jul. 9, 1993). "Cure of Xenografted Human Carcinomas by BR96-Doxorubicin Immunoconjugates," *Science* 261(5118):212-215.

Trail, P.A. et al. (2003, e-pub. Jan. 16, 2003). "Monoclonal Antibody Drug Immunoconjugates for Targeted Treatment of Cancer," *Cancer Immunol. Immunother.* 52(5):328-337.

Vogel, C.L. et al. (2002). "Efficacy and Safety of Trastuzumab As a Single Agent in First-Line Treatment of HER2-Overexpressing Metastatic Breast Cancer," *J. Clin. Oncol.* 20(3):719-726.

Medina-Kauwe, L.K. et al. (Aug. 24-29, 1997). "A Novel Gene Delivery System for Cell-Specific Targeting," *FASEB Journal*, 11(9):A862, Meeting: 17th International Congress of Biochemistry and Molecular Biology in conjunction with the Annual Meeting of the American Society for Biochemistry and Molecular Biology, San Francisco, CA. Abstract Only, 1 page.

Medina-Kauwe, L.K. et al. (Nov. 2002). Ad5 Capsid Protein Uptake and Trafficking in HeLa Cells. *Molecular Biology of the Cell*, 13(Supplement):541a-542a. Meeting: 42nd Annual Meeting of the American Society for Cell Biology. San Francisco, CA, USA. American Society for Cell Biology.

Medina-Kauwe, L.K. (Nov. 14, 2003). "Endocytosis of Adenovirus and Adenovirus Capsid Proteins," *Adv. Drug Delivery Rev.* 55(11):1485-1496.

Medina-Kauwe, L.K. (2003). "Heregulin-Targeted Protein Uptake for Breast Cancer," NCI: 1R01CA102126-01, Abstract Only, 4 pages.

Medina-Kauwe, L.K. (2004). "Heregulin-Targeted Protein Uptake for Breast Cancer," NCI: 5R01CA102126-02, Abstract Only, 4 pages.

Medina-Kauwe, L.K. (2005). "Heregulin-Targeted Protein Uptake for Breast Cancer," NCI: 5R01CA102126-03, Abstract Only, 4 pages.

Medina-Kauwe, L.K. (2006). "Heregulin-Targeted Protein Uptake for Breast Cancer," NCI: 5R01CA102126-04, Abstract Only, 4 pages.

Medina-Kauwe, L.K. (Jun. 2005). "Introduction to the Special Issue: Traveling the Intracellular Highway to Gene Therapy," *Gene Therapy* 12(11):863-864.

Medina-Kauwe, L.K. (2006). "Non-Viral Mediated Gene Delivery for Therapeutic Applications," *Gene Therapy for Neurological Disorders*, 115-140 (Chapter 8).

Medina-Kauwe, L.K. (2007). "A Novel Targeted Therapeutic Using Viral Capsid Protein," NCI: 1R21CA116014-01A2, Abstract Only, 4 pages.

Medina-Kauwe, L.K. (2008). "A Novel Targeted Therapeutic Using Viral Capsid Protein," NCI: 5R21CA116014-02, Abstract Only, 4 pages.

Medina-Kauwe, L.K. (2009). "Protein-DNA Drug Carriers for Tumor Targeting," NCI: 1R01CA129822-01A2, Abstract Only, 4 pages.

Medina-Kauwe, L.K. (2010). "Protein-DNA Drug Carriers for Tumor Targeting," NCI: 5R01CA129822-02, Abstract Only, 4 pages.

Medina-Kauwe, L.K. (2011). "Protein-DNA Drug Carriers for Tumor Targeting," NCI: 4R01CA129822-03, Abstract Only, 4 pages.

Medina-Kauwe, L.K. (2010). "Tumor Targeted Corroles for Detection and Intervention," NCI: 1R01CA140995-01A1, Abstract Only, 5 pages.

Medina-Kauwe, L.K. (2011). "Tumor Targeted Corroles for Detection and Intervention," NCI:5R01CA140995-02, Abstract Only, 5 pages.

U.S. Appl. No. 15/703,323, filed Sep. 13, 2017 for Medina-Kauwe et al.

U.S. Appl. No. 15/816,881, filed Nov. 17, 2017 for Medina-Kauwe et al.

Aris, A. et al. (Jul. 2004). "Modular Protein Engineering for Non-Viral Gene Therapy," *Trends In Biotechnology* 22(7):371-377.

* cited by examiner

TARGETED DELIVERY SYSTEM

CROSS-REFERENCE TO RELATED APPLICATIONS

This application is a continuation-in-part of International PCT Application No. PCT/US10/21830, filed Jan. 22, 2010, which includes a claim of priority to U.S. provisional patent application No. 61/147,037, filed Jan. 23, 2009.

GOVERNMENT RIGHTS

This invention was made with government support under Grant No. W81XWH-06-1-0549 awarded by the Department of Defense. The government has certain rights in the invention.

FIELD OF THE INVENTION

The invention relates to the field of biotechnology; specifically, to methods of inhibiting sequence-specific gene expression.

BACKGROUND OF THE INVENTION

All publications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

In the late 1970s oligonucleotides complementary to messenger RNA (mRNA) were shown to have the capability to knock down, partially or completely, sequence-specific gene expression (antisense technology, AS). The potential of AS seemed vast: in the lab, AS technology could be used to study gene function and complex regulatory pathways by knocking down expression of one gene, or multiple genes, at a time and location of the researcher's choosing; in the clinic, the possibility of shutting off expression of genes known to be involved in disease processes (e.g., oncogenes) beckoned as a new and exciting treatment modality. However, the lack of vectors that could stably, safely, accurately and efficiently deliver therapeutic AS molecules to the desired cell or tissue type was, in many ways, the single biggest hurdle to exploitation of AS technology in the therapeutics market. This dearth confined the market to diseases in which therapeutics could be administered locally, for example, the eye (injection), respiratory passages (inhalation), and the liver. The first, and only, FDA-approved AS drug did not reach the market until 1998; that drug, Isis Pharmaceutical's formivirsen (Vitravene), a 21-mer oligonucleotide against cytomegalovirus (CMV) retinitis in AIDS patients, must be injected directly into the eye. It acts by specifically affecting CMV gene expression, shutting down the virus but not interfering with the normal functioning of human DNA.

Coincidentally, 1998 was the year in which Fire & Mello published their seminal work on RNA interference (RNAi), work that greatly accelerated advances in AS development and for which they were awarded the 2006 Nobel Prize in Physiology. RNAi is a naturally-occurring, evolutionarily conserved, cellular mechanism of gene regulation achieved through the action of sequence-specific short interfering RNA molecules (siRNA) of which there are several structural types.

Its advantages notwithstanding, use of RNAi presented its own drawbacks and shared with AS technology the lack of reasonably priced, non-toxic vectors that could deliver the nucleotide payload accurately and efficiently. This lack, as with AS technology, confined the development of RNAi therapeutics to those that could be administered locally (again, the eye, respiratory passages, and liver).

Thus, there is a need in the art for novel and effective means of targeted delivery of RNAi and AS therapeutics.

SUMMARY OF THE INVENTION

Various embodiments include a method of treating a disease in an individual, comprising providing a treatment delivery platform comprising a polypeptide sequence adapted to target and/or penetrate a type of cell, and a delivery molecule bound to the polypeptide sequence via electrostatic interactions, and administering a therapeutically effective amount of the treatment delivery platform to the individual to treat the disease. In another embodiment, the delivery molecule comprises siRNA. In another embodiment, the disease comprises cancer. In another embodiment, the polypeptide sequence comprises a decalysine motif. In another embodiment, the polypeptide sequence comprises a Her segment. In another embodiment, the polypeptide sequence comprises a penton base segment. In another embodiment, the polypeptide sequence comprises SEQ ID NO: 5. In another embodiment, the type of cell comprises a HER2+ cancer cell. In another embodiment, the delivery molecule comprises a T7 transcribed siRNA. In another embodiment, the treatment delivery platform is administered to the individual intravenously and/or by intratumoral injection. In another embodiment, the individual is a human. In another embodiment, the individual is a rodent. In another embodiment, the treatment delivery platform is a nanoparticle comprising a plurality of HerPBK10-siRNA molecules.

Other embodiments include a treatment delivery platform, comprising a polypeptide sequence adapted to target and/or penetrate a type of cell, and a delivery molecule bound to the polypeptide sequence via electrostatic interactions. In another embodiment, the the polypeptide sequence comprises a decalysine motif. In another embodiment, the polypeptide sequence comprises a Her segment. In another embodiment, the polypeptide sequence comprises a penton base segment. In another embodiment, the polypeptide sequence comprises SEQ ID NO: 5. In another embodiment, the type of cell comprises a HER2+ cancer cell. In another embodiment, the delivery molecule comprises siRNA. In another embodiment, the delivery molecule comprises a T7 transcribed siRNA.

Other embodiments include a pharmaceutical composition, comprising a treatment delivery platform comprising a polypeptide sequence adapted to target and/or penetrate a type of cell, and a delivery molecule bound to the polypeptide sequence via electrostatic interactions, and a pharmaceutically acceptable carrier. In another embodiment, the delivery molecule comprises siRNA. In another embodiment, the type of cell is a HER2+ cancer cell.

Various embodiments include a method of preparing a pharmaceutical composition, comprising combining a polypeptide sequence adapted to target and/or penetrate a type of cell, with a delivery molecule, wherein the polypeptide sequence binds to the delivery molecule via electrostatic interactions, and combining said treatment delivery platform with a pharmaceutically acceptable carrier. In another embodiment, the delivery molecule comprises siRNA. In another embodiment, the combining of the polypeptide sequence with the delivery molecule comprises incubating the polypeptide sequence with the delivery molecule.

Other features and advantages of the invention will become apparent from the following detailed description, taken in conjunction with the accompanying drawings, which illustrate, by way of example, various embodiments of the invention.

BRIEF DESCRIPTION OF THE DRAWINGS

Exemplary embodiments are illustrated in referenced figures. It is intended that the embodiments and figures disclosed herein are to be considered illustrative rather than restrictive.

and GFP fluorescence (MDAMB-231 cells), and applying DTMDA-MB-435=DTTotal-DTMDA-MB-231 as previously described [11]. Relative survival is shown for Day 2 of treatment. E, Targeted glioma cell death in vitro. U251 cells were treated once with the indicated HerDox (and competitive inhibitor where indicated) or Dox doses and measured for cell survival at the indicated time points after treatment. *, P<0.05 compared to Mock.

Figure 28:
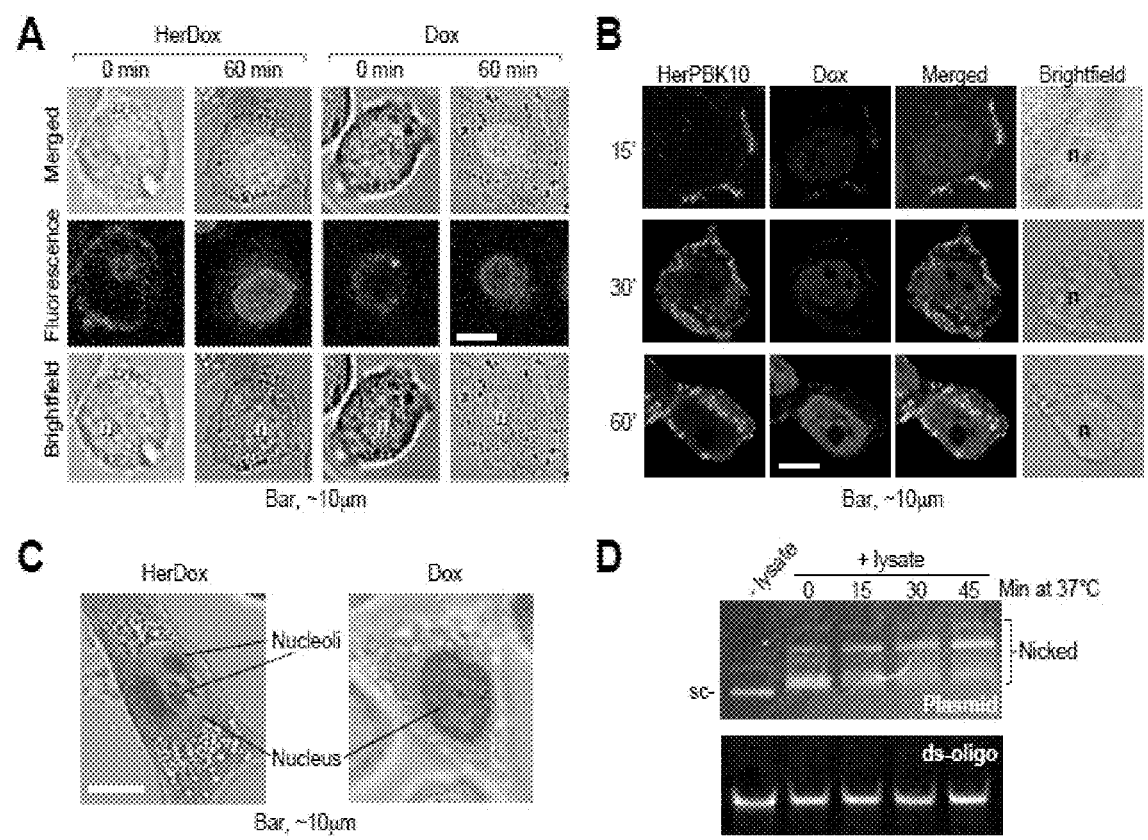

FIG. 28 depicts, in accordance with an embodiment herein, intracellular Dox release. HerDox and Dox (0.5 uM final Dox concentration) uptake and trafficking, assessed in fixed (A-B) and live (C) MDA-MB-435 cells. A, Uptake pattern of Dox fluorescence (red) when administered as free Dox or HerDox. B, HerPBK10 (green) and Dox (red) destinations after HerDox uptake. n, nucleus. C, Live MDA-MB-435 cells after incubation with HerDox or Dox for 1 h, followed by washing. Dox fluorescence (magenta) is overlaid on DIC images. D, Ds-oligo stability in cytosolic lysates. Gels show EtBr-staining of duplex and 3 kb plasmid after incubation with either lysate or HBS (-lysate). Relaxed (nicked) and supercoiled (sc) plasmid forms are indicated.

Figure 29:
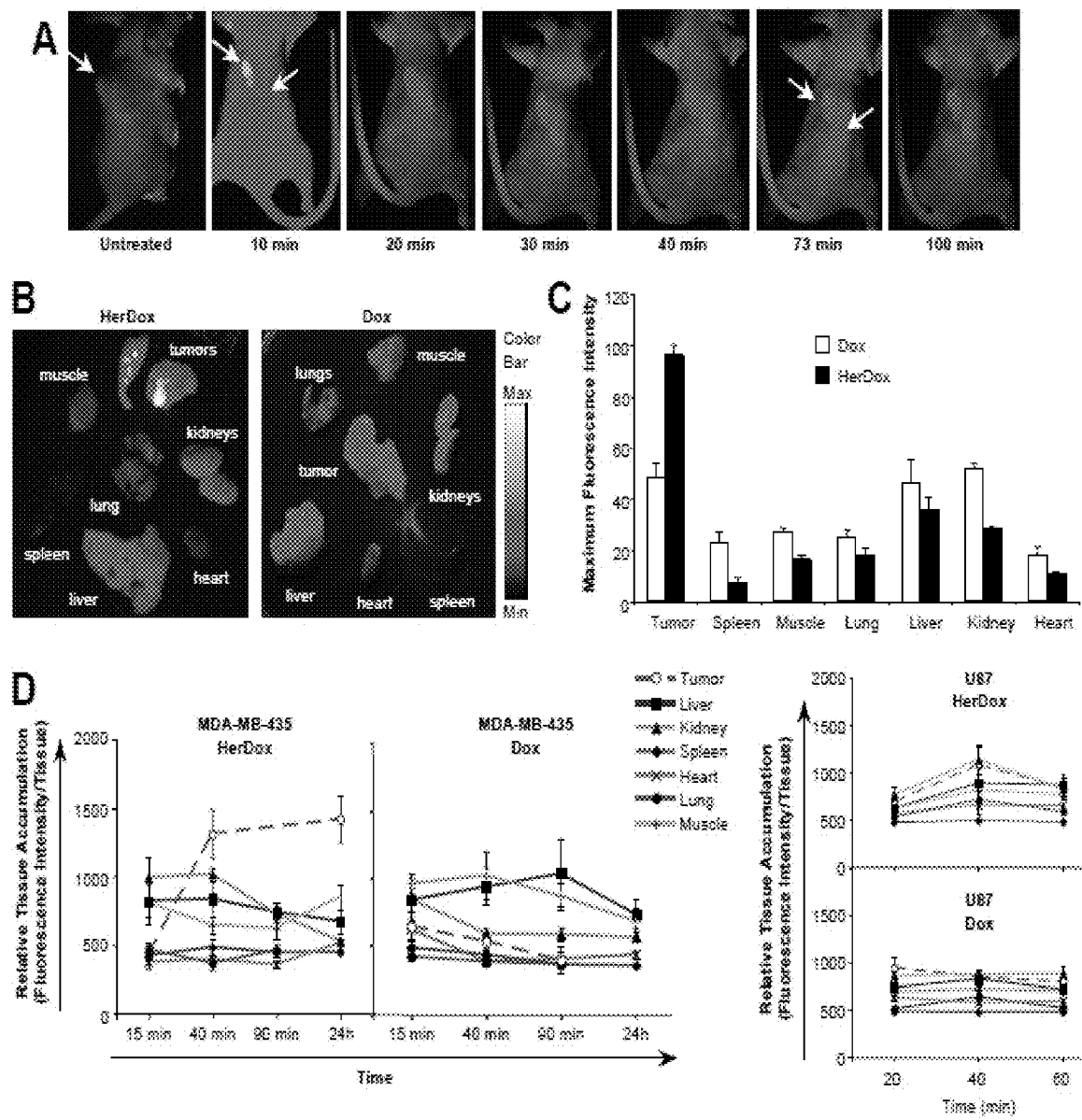

FIG. 29 depicts, in accordance with an embodiment herein, preferential targeting to HER2+ tumors. Tumor-bearing mice were i.v.-injected with HerDox or Dox and (A) imaged with a custom small animal imager adjusted to detect Dox fluorescence, or (B-D) euthanized, and tissues harvested at indicated timepoints for biodistribution and pharmacokinetic analyses. A, Live mouse imaging of HerDox at indicated time points after injection. Arrows, Tumors. B-C, Comparative biodistribution of HerDox and Dox in tissues harvested at 3 h post-injection. B, Imaging of biodistribution in harvested tissues. Pseudocolored FI corresponds to the color bar. Max, highest FI. C, Quantification of HerDox and Dox biodistribution, showing Dox FI/tissue. D, Comparative pharmacokinetics of HerDox and Dox in mice with tumors expressing differential HER2. Tissues were harvested from independently injected mice euthanized at indicated time points after injection and FI/tissue acquired using a small animal imaging system as described herein.

Figure 30:
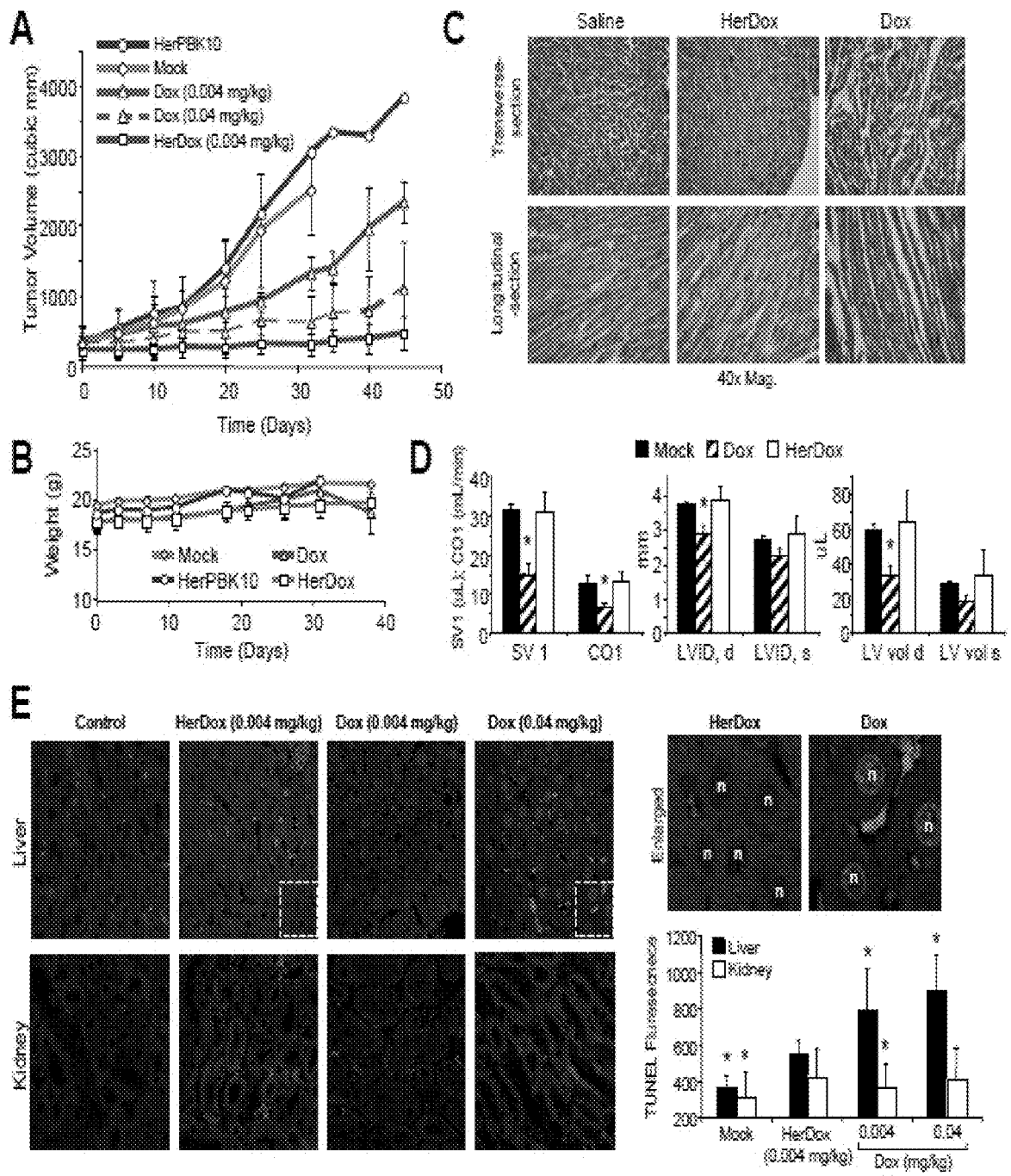

FIG. 30 depicts, in accordance with an embodiment herein, HerDox induces tumor-targeted growth ablation while sparing the heart after i.v. delivery. Comparison of HerDox (0.004 mg/kg) and Dox (0.004 or 0.04 mg/kg, where indicated) on (A) tumor growth (N=8-10 tumors per treatment), (B) animal weight (N=4-5 mice/treatment group), (C) cardiac tissue, (D) cardiac function (N=3 mice/treatment group), and (E) liver and kidney tissue. Day 0 in A-B corresponds to 3 days before tail vein injections. Control (saline-injected) mice were euthanized early due to tumor ulceration, in compliance with IACUC policy. Tumor growth in A was obtained by measuring tumor volumes. C, Histology of myocardia from treated mice. Micrographs show representative H&E stained specimens from treated mice. D, Echocardiography of mice obtained at 25 days following injections. *, P<0.05, compared to mock-treatment. B-D performed on mice receiving 0.004 mg/kg doses. HerPBK10 dose equates HerDox protein concentration. E, TUNEL staining and quantification in liver and kidney tissue obtained from treated mice. Micrographs obtained at 20× magnification (left set of panels) show fluorescently-stained nuclei in apoptotic cells (delineated areas are enlarged in micrographs to the right). Graph summarizes relative fluorescence intensities of each treated tissue (N>200 fields per treatment). Quantification procedure is described herein. *, P<0.0001 compared to each corresponding HerDox treatment.

Figure 31:
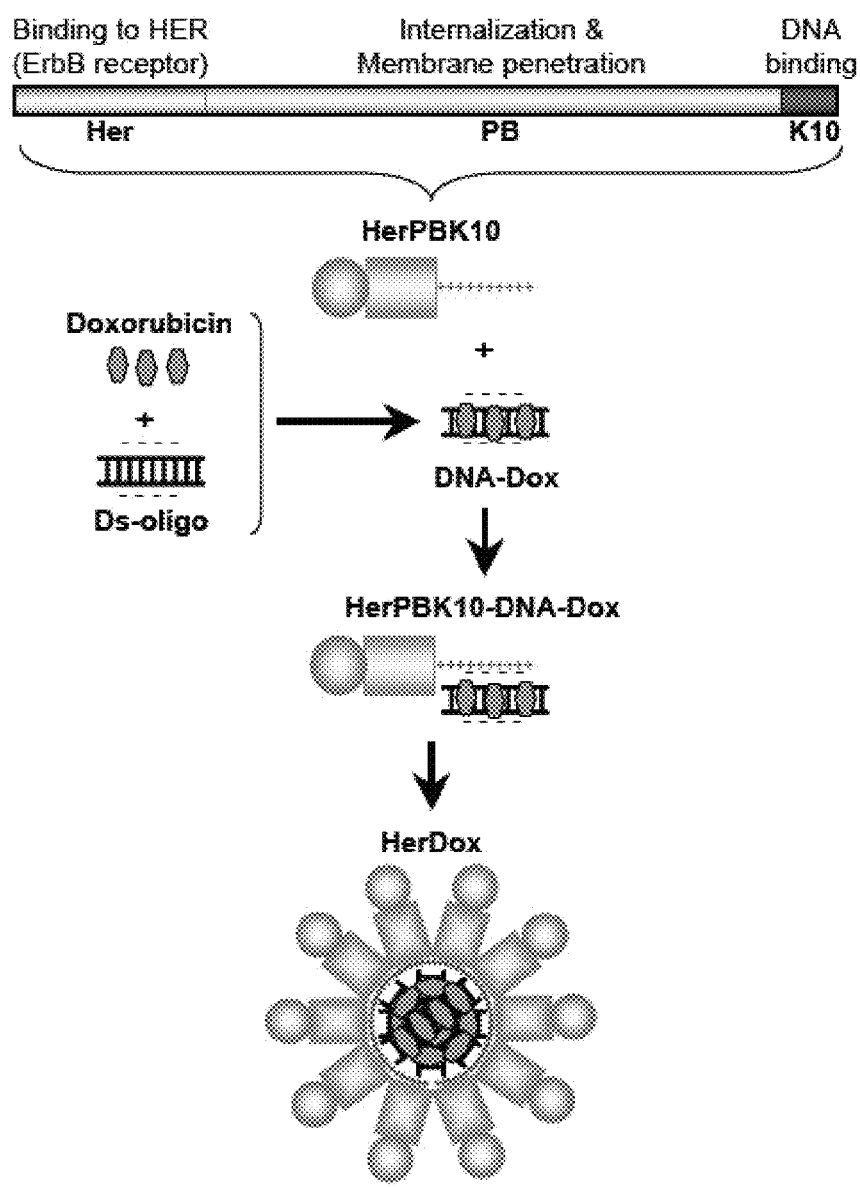

FIG. 31 depicts, in accordance with an embodiment herein, HerDox assembly. HerDox self-assembly is based on known intercalation and electrophilic interactions of both Dox and HerPBK10 with DNA, respectively, and results from the combination of an oligonucleotide duplex (ds-oligo) with doxorubicin (Dox) and the gene delivery protein, HerPBK10. Drawing of complex assembly is based on a 16:1 molar ratio of Dox:DNA (and is verified by complete capture of Dox at 16:1 ratio, and ~10:1 molar ratio of HerPBK10:DNA, verified in previous studies showing that proportionate DNA phosphates are neutralized by the HerPBK10 carboxy-terminal decalysine. Both ratios are based on a 48 bp oligoduplex. The quaternary structure is speculated from several observations in these studies: First, solvent-exposure of the HER-targeting domains is based on the observation that delivery is competitively inhibited by free ligand and governed by receptor level in vitro. Second, the surrounding of DNA-Dox by HerPBK10 is deduced from the DNA-Dox "protection" studies: HerPBK10 directly binds the ds-oligo and protects the DNA from serum degradation. Third, cryoEM imaging shows the formation of ~10 nm diameter round particles after HerDox assembly.

Figure 32:
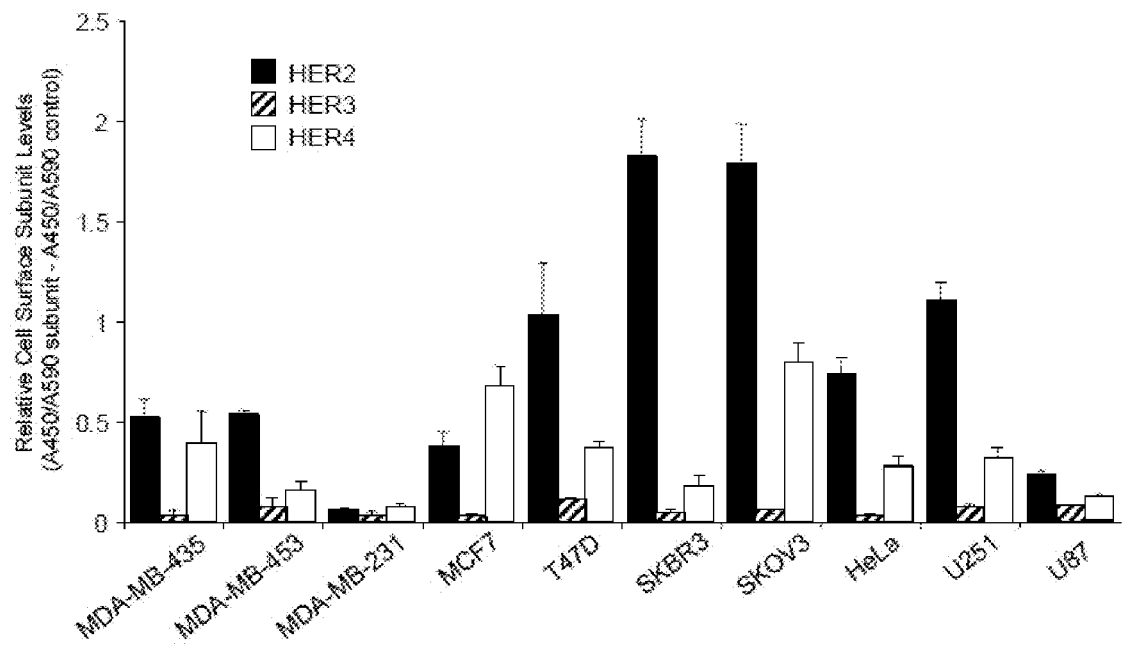

FIG. 32 depicts, in accordance with an embodiment herein, relative cell surface HER subunit levels as measured by ELISA. Human tumor cell lines of breast cancer* (MDA-MB-435, MDA-MB-453, MDA-MB-231, MCF7, T47D, SKBR3), ovarian cancer (SKOV3), cervical carcinoma (HeLa), and glioma (U251, U87) origin were plated on a 96-well plate at 1×104 cells/well and grown ~36 h before fixation and ELISA processing following standard procedures. HER subunits were recognized using the following antibodies: 1 ug/mL anti-erbB-2/HER2 rabbit polyclonal IgG and anti-erbB-3/HER3 mouse monoclonal IgG (Upstate Biotechnology Inc., Lake Placid, N.Y., USA); and 3 ug/mL mouse monoclonal (HFR1) to HER4 (Abcam Inc., Cambridge, Mass., USA). ELISA product formation was quantified by absorbance at 450 nm. Relative cell numbers were quantified by crystal violet staining and absorbance at 590 nm. Relative subunit levels are reported as the ELISA signal of each cell population normalized by the relative cell number, or absorbance 450 nm/590 nm. Control measurements (450 nm/590 nm of cells not receiving primary antibody) were subtracted from the respective experimental measurements. N=3 per data point. Cell lines were obtained directly from the National Cancer Institute (NCI) and ATCC.

Figure 33:
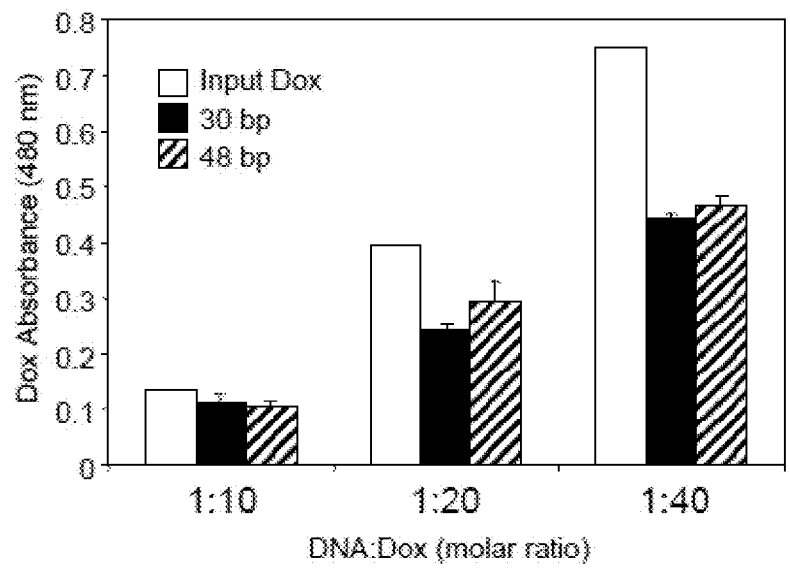

FIG. 33 depicts, in accordance with an embodiment herein, oligonucleotide length does not affect Dox incorporation into the targeted complex. Oligonucleotide duplexes were formed by annealing complementary 30 bp (LLAA-5 and LLAA-3) or 48 bp (BglIIHis-5 and BglIIHis-3) oligonucleotides. Dox was added to each set of duplexes at either 1:10, 1:20, or 1:40 molar ratio duplex:Dox (at a final Dox concentration of either 20, 40, or 80 uM) in 10 mM Tris/HCl buffer, pH 8.0, for 30 min at RT. Free Dox was separated from incorporated Dox by ultrafiltration through 10K mwco membranes (Microcon Ultracel YM10; Millipore). Retentates and filtrates were collected separately from triplicate samples, and retentate absorbances measured at 480 nm. Input Dox, A480 before ultrafiltration.

Figure 34:
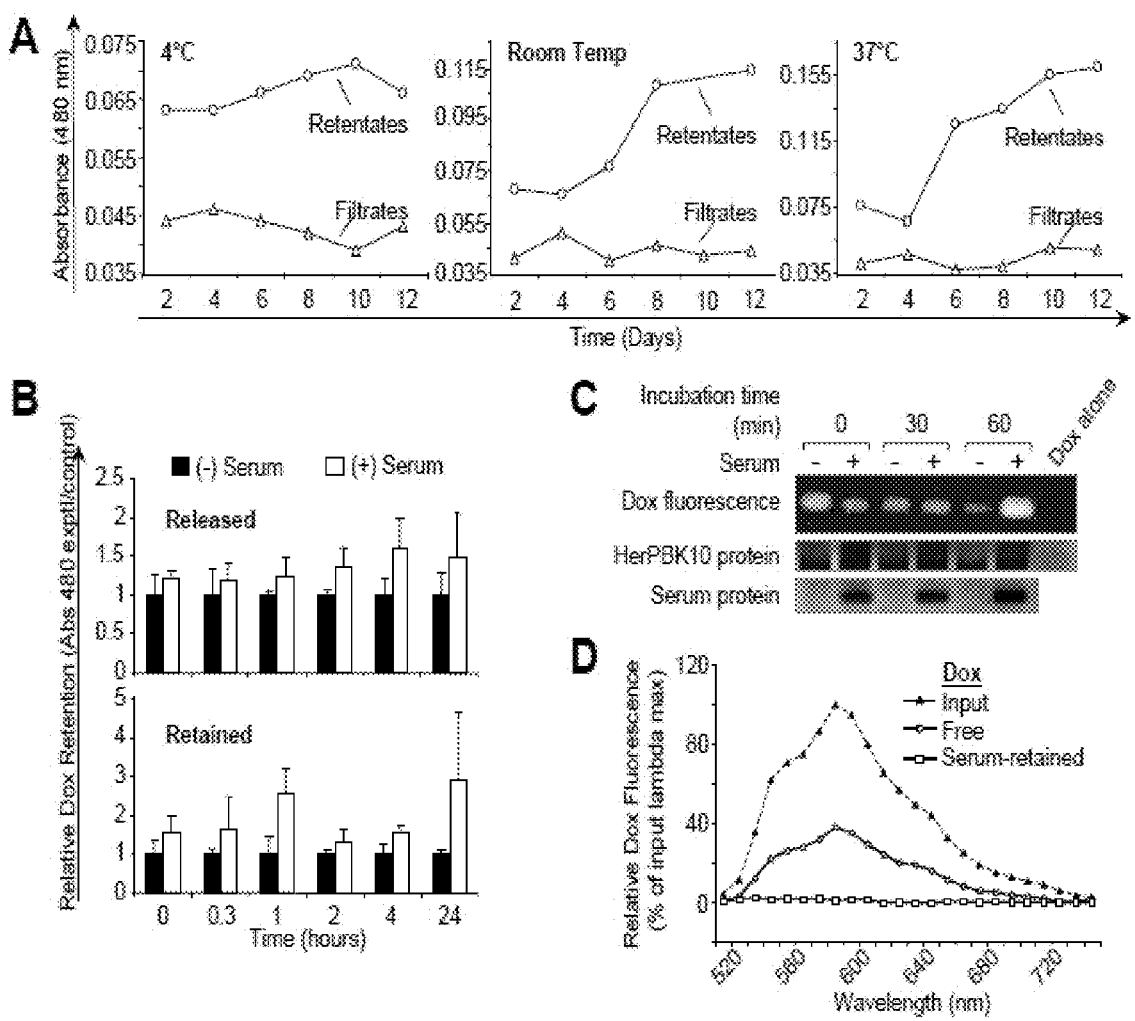

FIG. 34 depicts, in accordance with an embodiment herein, HerDox stability in storage and cell culture. A, HerDox stability in different storage conditions. HerDox was incubated at indicated times and temperatures was applied to a 10K mwco ultrafiltration membrane every other day, and retentate and filtrate A480 measured to determine relative Dox retention or release from complexes, respectively. While storage at different incubation times and temperatures (4° C., RT, or 37° C. over a 12 day period) yielded no detectable Dox release from HerDox, RT and 37° C. produced an increase in retained particle absorbance, suggesting that these conditions may enhance Dox incorporation into HerDox. B, Assessing stability in serum-containing media by ultrafiltration. HerDox immobilized on Ni-NTA beads (Qiagen Inc., Valencia, Calif., USA) by incubation on ice for 2 h with agitation followed by free HerDox removal via bead pelleting/washing in HBS received 10% fetal bovine serum (FBS), to mimic cell culture conditions, and incubated at 37° C. with agitation for the indicated time-points. At each time-point, samples were pelleted and mean A480±SD (N=3) of supernatants (Released) and bead eluates (Retained) were measured. Eluates were obtained by HerDox elution using 400 mM imidazole-containing buffer. Relative Dox release or retention in serum is expressed as normalized to control (corresponding serum-lacking sample). C, Assessing serum stability by gel electrophoresis. HerDox was electrophoresed on a 2% agarose gel after indicated incubation times at 37° C. in serum-containing (DMEM/10% FBS) or serum-free cell culture medium. Dox fluorescence (top panel) was visualized by UV excitation. The gel was stained with Coomassie blue (middle panel) to identify HerPBK10 and serum protein (lower panel) from culture media samples. D, Assessing transfer of free Dox to serum. Dox (1.6 nmoles) was added to serum coated wells and incubated for 30 min at 37° C. with agitation before supernatants were removed and the wells washed once with HBS before fluorescence spectra were measured for pre-incubation sample (Input), supernatant (Free) and wells (Serum-bound). Fluorescence spectra were obtained at Ex 485 nm/Em 520-750 nm with a 515 nm cutoff filter.

Figure 35:
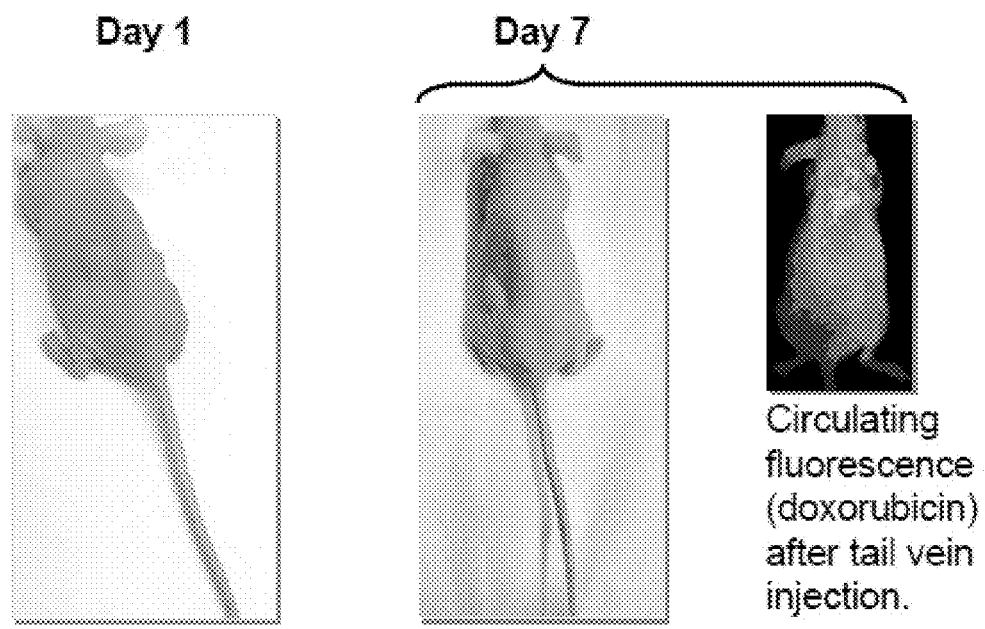

FIG. 35 depicts, in accordance with an embodiment herein, daily tail vein injections. As described herein, tumor-bearing mice received once-daily tail vein injections of indicated reagent for seven sequential days. Using a 29 gauge insulin needle and maintaining as much sterility of injection materials as possible promoted successful procedure with minimal tail vein collapse, infection, or necrosis. Each tail was pre-warmed by brief immersion in a sterile 50 mL conical tube filled with clean, distilled water maintained at 40° C. (to increase circulation to the tail, thus enlarging the veins and making them more visible), then cleaned with an alcohol swab immediately before injection. Two lateral veins and a dorsal vein along the entire length of the tail allowed alternate choices of injection sites if the first site failed. Photos show representative mice and tails after the first (Day 1) and last (Day 7) injections of doxorubicin. Fluorescent image shows circulating doxorubicin after the final injection, indicating that repeated injections did not prevent systemic delivery.

Figure 36:
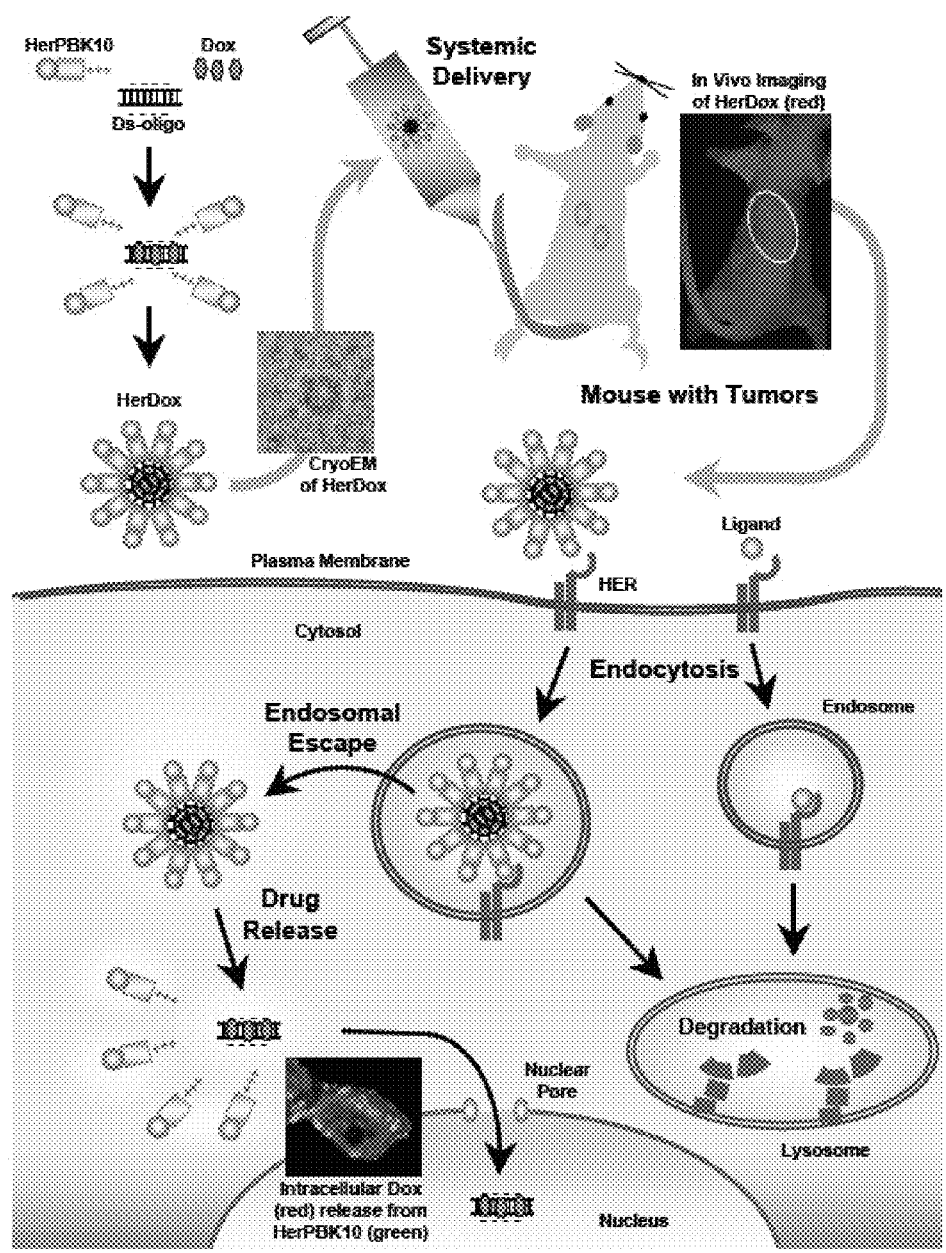

FIG. 36 depicts, in accordance with an embodiment herein, a summary of an overall mechanism of action.

DETAILED DESCRIPTION

All references cited herein are incorporated by reference in their entirety as though fully set forth. Unless defined otherwise, technical and scientific terms used herein have the same meaning as commonly understood by one of ordinary skill in the art to which this invention belongs. Singleton et al., Dictionary of Microbiology and Molecular Biology 3rd ed., J. Wiley & Sons (New York, N.Y. 2001); March, Advanced Organic Chemistry Reactions, Mechanisms and Structure 5th ed., J. Wiley & Sons (New York, N.Y. 2001); and Sambrook and Russel, Molecular Cloning: A Laboratory Manual 3rd ed., Cold Spring Harbor Laboratory Press (Cold Spring Harbor, N.Y. 2001), provide one skilled in the art with a general guide to many of the terms used in the present application.

One skilled in the art will recognize many methods and materials similar or equivalent to those described herein, which could be used in the practice of the present invention. Indeed, the present invention is in no way limited to the methods and materials described. For purposes of the present invention, the following terms are defined below.

"Beneficial results" may include, but are in no way limited to, preventing, reducing, preventing the increase of and inhibiting the proliferation or growth of cancer cells or tumors. Beneficial results may also refer to curing the cancer and prolonging a patient's life or life expectancy.

"Cancer" and "cancerous" refer to or describe the physiological condition in mammals that is typically characterized by unregulated cell growth. Examples of cancer include, but are not limited to, ovarian cancer, breast cancer, colon cancer, lung cancer, prostate cancer, hepatocellular cancer, gastric cancer, pancreatic cancer, cervical cancer, liver cancer, bladder cancer, cancer of the urinary tract, thyroid cancer, renal cancer, carcinoma, melanoma, head and neck cancer, and brain cancer.

"Curing" cancer includes degrading a tumor such that a tumor cannot be detected after treatment. The tumor may be reduced in size or become undetectable, for example, by atrophying from lack of blood supply or by being attacked or degraded by one or more components administered according to the invention.

"Mammal" as used herein refers to any member of the class Mammalia, including, without limitation, humans and nonhuman primates such as chimpanzees and other apes and monkey species; farm animals such as cattle, sheep, pigs, goats and horses; domestic mammals such as dogs and cats; laboratory animals including rodents such as mice, rats and guinea pigs, and the like. The term does not denote a particular age or sex. Thus, adult and newborn subjects, as well as fetuses, whether male or female, are intended to be included within the scope of this term.

"Pathology" of cancer includes all phenomena that compromise the well-being of the patient. This includes, without limitation, abnormal or uncontrollable cell growth, metastasis, interference with the normal functioning of neighboring cells, release of cytokines or other secretory products at abnormal levels, suppression or aggravation of inflammatory or immunological response, neoplasia, premalignancy, malignancy, invasion of surrounding or distant tissues or organs, such as lymph nodes, etc.

"Prevention" as used herein refers to efforts undertaken to hinder the development or onset of a condition or cancer condition even if the effort is ultimately unsuccessful.

"Condition" as used herein refers to an illness or physical ailment.

"Therapeutically effective amount" as used herein refers to that amount which is capable of achieving beneficial results in a patient with cancer. A therapeutically effective amount can be determined on an individual basis and will be based, at least in part, on consideration of the physiological characteristics of the mammal, the type of delivery system or therapeutic technique used and the time of administration relative to the progression of the disease.

"Treatment" and "treating," as used herein refer to both therapeutic treatment and prophylactic or preventative measures, wherein the object is to achieve beneficial results even if the treatment is ultimately unsuccessful.

"Tumor," as used herein refers to all neoplastic cell growth and proliferation, whether malignant or benign, and all pre-cancerous and cancerous cells and tissues.

As used herein, "Her" refers to a segment obtained from the receptor binding domain of heregulin-α, which binds to HER2/HER3 or HER2/HER4 subunit heterodimers. As used herein, "PB" refers to a penton base segment that normally mediates cell binding, entry, and cytosolic penetration of adenovirus serotype 5 during the early stages of infection. This penton base protein normally has an RGD motif (Arg-Gly-Asp). As used herein, "K10" refers to a decalysine motif that has the capacity to bind nucleic acids by electrophilic interaction. Similarly, a point mutation of the RGD motif may be used to create an EGD motif (Glu-Gly-Asp), resulting in a HerPBrgdK10 polypeptide molecule (rather than HerPBK10).

As used herein, the term "HerDox" refers to a nanoparticle made up of a plurality of HerPBK10-siRNA molecules.

As readily apparent to one of skill in the art, any number of variations and examples of polynucleotide and polypeptide sequences described herein. For example, an example of HerPBK10, described herein as SEQ ID NO: 1, may also include the complement polynucleotide sequence. Or, for example, it may include SEQ ID NO: 5, a polypeptide penton base (PB) sequence. Similarly, SEQ ID NO: 2, a 3' primer for PB, SEQ ID NO: 3, a 3' primer for PBK10, and SEQ ID NO: 4, a 3' primer for HerK10, may also be used to generate versions of the HerPBK10 construct in conjunction with various embodiments described herein.

As will be readily apparent to one of skill in the art, any number of antisense sequences or technology may be used in accordance with various embodiments described herein, including siRNA, triphosphate-capped siRNA, shRNA, dsRNA, double stranded nucleic acids, and RNAi. The invention is in no way limited to an siRNA molecule.

As is known to one of skill in the art, any number of targeting ligands may be used in accordance with various embodiments described herein. For example, PB itself may act as a targeting ligand of PBK10 when targeting integrins such as $\alpha_v\beta_3$. As known by one of skill in the art, integrins are overly expressed in various types of metastatic tumors. Thus, in conjunction with various embodiments described herein, PBK10 may be used to target metastatic tumors and cells with a high expression of integrins.

As disclosed herein, the inventors tested whether a recombinant adenovirus (Ad) capsid protein, HerPBK10, which can selectively bind to HER2+ breast cancer, mediates missile-like targeted delivery of siRNA and induces tumor cell-specific death via siRNA-mediated "knock-down" of specific gene transcripts. The inventors designed HerPBK10 to penetrate HER2+ cells by combining the 'Her' domain for binding heregulin receptors, which have an increased ligand affinity on HER2+ tumor cells, and the membrane lysis and intracellular trafficking features of the 'PB' domain, which is derived from the cell-entry functions of the Ad capsid. Binding and transport of nucleic acids can be mediated by the polylysine, 'K10' domain. To demonstrate that Her-PBK10 can mediate targeted siRNA delivery, the inventors first used ELISA and/or immunofluorescence to establish the receptor profiles of frequently-used cell lines characterized by different levels of heregulin receptor subunits. It was observed that HerPBK10 underwent substantially greater cell binding and uptake in HER2+ human breast cancer cells while minimal to negligible levels of binding and uptake were detected from HER2− cells. Using in vivo fluorescence imaging, it was observed that the targeting ligand used here specifically accumulates at HER2+ tumor tissue in mice while evading accumulation in other tissues. It was also observed that HerPBK10 could mediate the uptake of a Cy3-labeled oligonucleotide in HER2+ cells. The formation of noncovalent conjugates resulting from incubating HerPBK10 with siRNA was verified by the observation that siRNA electromobility dose-dependently decreased as HerPBK10 concentration increased. Ultrafiltration of conjugates under high speed centrifugation demonstrated that free siRNA could be separated from siRNA bound to the HerPBK10, and also indicated that the conjugate can withstand high shear forces without releasing the siRNA molecule. Targeted conjugates delivering anti-Her2 siRNA were added to HER2+ human breast cancer cells in culture, and yielded specific gene "knock-down" in target cells. Associated with this reduction was substantial target cell death. Depending on the cell line, up to 85% reduction was observed in HER2+ cell survival whereas HER2− cells receiving the targeted conjugate were little affected. HerPBK10 also augmented liposomal delivery of siRNA: when combined with liposome-coated siRNA, HER2+ cell numbers were considerably reduced whereas HER2− cell numbers showed only slight to negligible reduction. SiRNA Lipoplexes alone (lacking HerPBK10) only modestly to negligibly reducted the survival of both HER2+ and HER2− cells. Altogether, these findings indicate that HerPBK10 enables missle-like delivery of siRNA, resulting in targeted cell death.

Figure 1:
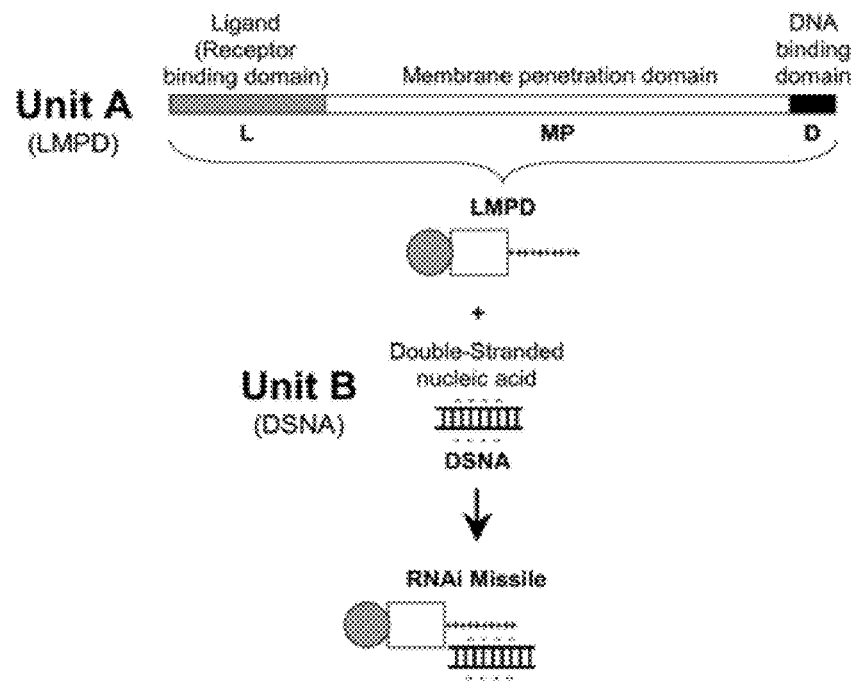
FIG. 1 depicts on representation of an siRNA delivery system in accordance with an embodiment herein.

In one embodiment, this invention is designed to direct antisense and/or RNA interference (RNAi) to target cells. In another embodiment, the invention is comprised of two components that self-assemble into one targeted complex. In one form, the first component (Unit A) is a unique cell-penetrating carrier that can bind and enter target cells (FIG. 1). The second component (Unit B) may be a double-stranded nucleic acid that binds to the first component via electrostatic interactions (FIG. 1).

In one embodiment, the carrier is comprised of three main segments: 1. a unit designed to bind to specific target cells (FIG. 1, "L"); 2. a unit designed to mediate penetration into the interior of target cells (FIG. 1, "MP"); 3. a unit that can interact with nucleic acids designed to mediate RNAi (FIG. 1, "D").

In another embodiment, the nucleic acid may be comprised of: small interfering RNA (siRNA) of any length made from either synthetic or biological sources, small hairpin RNA (shRNA) of any length, complimentary oligonucleotides of any length, etc., to mediate RNAi in target cells. The nucleic acid may also contain any type of modification (i.e. addition of phosphate groups, etc) that may enhance its therapeutic efficacy. In another embodiment, an additional unit is formed where a plurality of HerPBK10 combined with siRNA form a nanoparticle.

Figure 2:
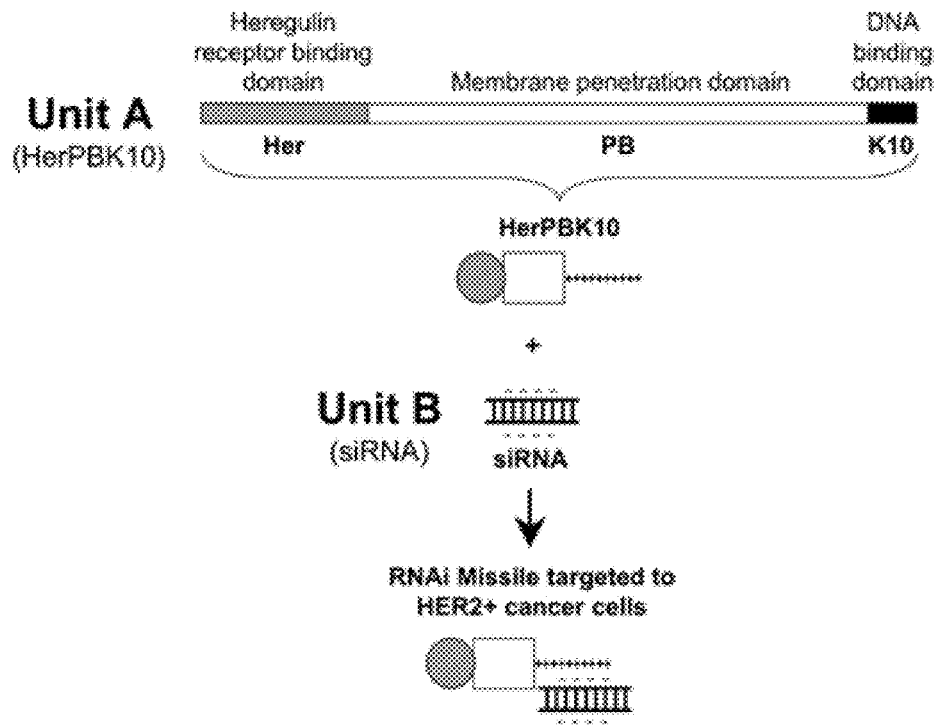
FIG. 2 depicts, in accordance with an embodiment herein, an assembly of HER-targeted siRNA missile.

The feasibility of this new type of therapeutic has been tested on HER2+ breast cancer in vitro and in vivo. To target HER2+ breast cancer, Unit A may be comprised of a protein called HerPBK10 (FIG. 2). HerPBK10 may contain the receptor binding domain of heregulin fused to the cell penetrating adenovirus penton base protein modified by a carboxy (C)-terminal decalysine (FIG. 2). The 'Her' segment of HerPBK10 may be obtained from the receptor binding domain of heregulin which binds specifically to HER2/HER3 or HER2/HER4 subunit heterodimers. Although heregulin interacts directly with HER3 or HER4, but not HER2, ligand affinity is greatly enhanced by HER2. Thus, tumor cells that over-express HER2 (known as HER2+ tumor cells) are ideal candidates for heregulin-directed targeting.

The membrane penetrating activity of the adenovirus serotype 5 (Ad5) penton base protein is incorporated into the 'PB' segment of HerPBK10 to facilitate penetration into target cells. The 'K10' segment is comprised of 10 lysine residues, whose positive charge can facilitate the transport of negatively charged molecules, such as nucleic acids, by electrophilic interaction.

The targeted RNAi delivery system enables the utilization of recombinant pathogen proteins modified for missile-like delivery and penetration of the RNAi therapeutic into target cells. This system is modular in its design, thus the cell targeting ligand may be exchanged for other ligands, depending on the cell targeted. In its practically applied form for tumor targeting and treatment, siRNA containing secondary modifications may be used to induce target cell induction of anti-tumor cytokines, and thus enhance tumor toxicity. The latter feature is unique to the method of use presented here, as sequence-independent cytotoxicity elicited by siRNA is currently considered an undesirable side effect by the research community at large. In one embodiment, this feature is exploited to enhance tumor toxicity by targeting the siRNA to tumor cells via the delivery agent.

The siRNA molecule delivery system includes a complex that can be administered to a mammal by various routes of administration, whereupon it hones in on target cells (e.g., cancer cells) to deliver an siRNA molecule into the cells. In one embodiment, the complex provides for delivery of an siRNA molecule to cancer cells while sparing normal, healthy cells. Current methods of siRNA therapy fail due to the many off-target effects of the therapy and use of chemical modification strategies that impair therapeutic activity, in accordance with embodiments described herein, an advantage of the inventive siRNA molecule delivery system is its targeting effects.

In various embodiments, the siRNA molecule delivery system can be incorporated into a pharmaceutical composition, which may be formulated for delivery via any route of administration. "Route of administration" may refer to any administration pathway known in the art, including but not limited to aerosol, nasal, oral, transmucosal, transdermal or parenteral. "Parenteral" refers to a route of administration that is generally associated with injection, including intraorbital, infusion, intraarterial, intracapsular, intracardiac, intradermal, intramuscular, intraperitoneal, intrapulmonary, intraspinal, intrasternal, intrathecal, intrauterine, intravenous, subarachnoid, subcapsular, subcutaneous, transmucosal, or transtracheal. Via the parenteral route, the compositions may be in the form of solutions or suspensions for infusion or for injection, or in the form of lyophilized powders.

The pharmaceutical compositions according to the invention can also contain any pharmaceutically acceptable carrier. "Pharmaceutically acceptable carrier" as used herein refers to a pharmaceutically acceptable material, composition, or vehicle that is involved in carrying or transporting a compound of interest from one tissue, organ, or portion of the body to another tissue, organ, or portion of the body. For example, the carrier may be a liquid or solid filler, diluent, excipient, solvent, or encapsulating material, or a combination thereof. Each component of the carrier must be "pharmaceutically acceptable" in that it must be compatible with the other ingredients of the formulation. It must also be suitable for use in contact with any tissues or organs with which it may come in contact, meaning that it must not carry a risk of toxicity, irritation, allergic response, immunogenicity, or any other complication that excessively outweighs its therapeutic benefits.

The pharmaceutical compositions according to the invention can also be encapsulated, tableted or prepared in an emulsion or syrup for oral administration. Pharmaceutically acceptable solid or liquid carriers may be added to enhance or stabilize the composition, or to facilitate preparation of the composition. Liquid carriers include syrup, peanut oil, olive oil, glycerin, saline, alcohols and water. Solid carriers include starch, lactose, calcium sulfate, dihydrate, terra alba, magnesium stearate or stearic acid, talc, pectin, acacia, agar or gelatin. The carrier may also include a sustained release material such as glyceryl monostearate or glyceryl distearate, alone or with a wax.

The pharmaceutical preparations are made following the conventional techniques of pharmacy involving milling, mixing, granulating, and compressing, when necessary, for tablet forms; or milling, mixing and filling for producing hard gelatin capsule forms. When a liquid carrier is used, the preparation will be in the form of a syrup, elixir, emulsion or an aqueous or non-aqueous suspension. Such a liquid formulation may be administered directly p.o. or filled into a soft gelatin capsule.

The pharmaceutical compositions according to the invention may be delivered in a therapeutically effective amount. The precise therapeutically effective amount is that amount of the composition that will yield the most effective results in terms of efficacy of treatment in a given subject. This amount will vary depending upon a variety of factors, including but not limited to, the characteristics of the therapeutic compound (including activity, pharmacokinetics, pharmacodynamics, and bioavailability), the physiological condition of the subject (including age, sex, disease type and stage, general physical condition, responsiveness to a given dosage, and type of medication), the nature of the pharmaceutically acceptable carrier or carriers in the formulation, and the route of administration. One skilled in the clinical and pharmacological arts will be able to determine a therapeutically effective amount through routine experimentation, for instance, by monitoring a subject's response to administration of a compound and adjusting the dosage accordingly. For additional guidance, see Remington: The Science and Practice of Pharmacy (Gennaro ed. 20th edition, Williams & Wilkins PA, USA) (2000).

Typical dosages of the siRNA molecule delivery system as well as the siRNA molecule itself and additional compounds delivered by it such as therapeutical compounds and/or imaging agents, can be in the ranges recommended by the manufacturer where known therapeutic compounds or imaging agents are used, and also as indicated to the skilled artisan by the in vitro responses or responses in animal models. The actual dosage will depend upon the judgment of the physician, the condition of the patient, and the effectiveness of the therapeutic method.

The invention also relates to methods of treating diseases by administration to a mammal in need thereof of elimination of a specific target, such as a tumor, or to silence target genes. In one embodiment of the invention, the disease is cancer. In another embodiment of the invention, the disease is breast cancer and/or HER2+ breast cancer.

The invention also relates to methods of diagnosing and/or prognosing a disease in a mammal by administering to the mammal an effective amount of the delivery system of the invention including an imaging agent appropriate to enable the imaging of cells and/or tissues relevant to the disease. In one embodiment of the invention, the disease is cancer and an imaging agent is delivered to image cancerous cells or tissue. In another embodiment of the invention, the disease is breast cancer and/or HER2+ breast cancer. The methods may include administration of the delivery system with a suitable imaging agent and the use of conventional imaging techniques to thereafter image the target tissue or cells and thereby diagnose and/or prognose the disease condition.

In other embodiments, the aforementioned methods may be used as research tool to allow greater understanding of relevant pathways or the pathology of a disease. Researchers in the cancer field, for example, could silence specific genes, inducing cell death and/or mediate cellular intake and intracellular release of co-delivered compounds.

In still further embodiments of the present invention, the aforementioned methods may be used in concert to, for example, image cells or tissues to research the effect of silencing specific genes or eliminating specific target cells. For instance, in one embodiment of the present invention, an imaging agent such as a GFP may be delivered with the siRNA molecule delivery system.

The present invention is also directed to a kit to treat cancer, including, but in no way limited to, breast cancer and more particularly HER2+ breast cancer. The kit is useful for practicing the inventive method of treating such conditions. The kit is an assemblage of materials or components, including at least one of the components of the siRNA molecule delivery system.

The exact nature of the components configured in the inventive kit depends on its intended purpose. For example, some embodiments are configured for the purpose of treating the aforementioned conditions in a subject in need of such treatment. The kit may be configured particularly for the purpose of treating mammalian subjects. In another embodiment, the kit is configured particularly for the purpose of treating human subjects. In further embodiments, the kit is configured for veterinary applications, for use in treating subjects such as, but not limited to, farm animals, domestic animals, and laboratory animals.

Other embodiments are configured for the purpose of imaging particular cells or tissues in a subject after deliver of an siRNA molecule. The kit may be configured particularly for the purpose of imaging cells or tissues in mammalian subjects. In another embodiment, the kit is configured particularly for the purpose of imaging cells or tissues in human subjects, including, but in no way limited to, breast cancer cells and more particularly HER2+ breast cancer cells. In further embodiments, the kit is configured for veterinary applications, for use in imaging cells and tissues in subjects such as, but not limited to, farm animals, domestic animals, and laboratory animals.

Instructions for use may be included in the kit. "Instructions for use" typically include a tangible expression describing the technique to be employed in using the components of the kit to effect a desired outcome, such as to treat a disease condition (e.g., cancer) or to image particular cells or tissues in a subject. Optionally, the kit also contains other useful components such as diluents, buffers, pharmaceutically acceptable carriers, syringes, catheters, applicators, pipetting or measuring tools, bandaging materials or other useful paraphernalia as will be readily recognized by those of skill in the art.

The materials or components assembled in the kit can be provided to the practitioner stored in any convenient and suitable ways that preserve their operability and utility. For example, the components can be in dissolved, dehydrated, or lyophilized form; they can be provided at room, refrigerated or frozen temperatures. The components are typically contained in suitable packaging material(s). As employed herein, the phrase "packaging material" refers to one or more physical structures used to house the contents of the kit, such as inventive compositions and the like. The packaging material is constructed by well known methods, preferably to provide a sterile, contaminant-free environment. The packaging materials employed in the kit are those customarily utilized in treatment of pituitary disorders and/or tumors and/or cancer. As used herein, the term "package" refers to a suitable solid matrix or material such as glass, plastic, paper, foil, and the like, capable of holding the individual kit components. Thus, for example, a package can be one or more glass vials used to contain suitable quantities of the components of the inventive delivery system in an unassembled, a partially assembled, or a completely assembled form. The packaging material generally has an external label which indicates the contents and/or purpose of the kit and/or its components.

EXAMPLES

The following example is provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

Example 1

Generally

The inventors tested whether a recombinant adenovirus (Ad) capsid protein, HerPBK10, which can selectively bind to HER2+ breast cancer, mediates missile-like targeted delivery of siRNA and induces tumor cell-specific death via siRNA-mediated "knock-down" of specific gene transcripts. The inventors designed HerPBK10 to penetrate HER2+ cells by combining the 'Her' domain for binding heregulin receptors, which have an increased ligand affinity on HER2+ tumor cells, and the membrane lysis and intracellular trafficking features of the 'PB' domain, which is derived from the cell-entry functions of the Ad capsid. Binding and transport of nucleic acids can be mediated by the polylysine, 'K10' domain. To demonstrate that HerPBK10 can mediate targeted siRNA delivery, the inventors first used ELISA and/or immunofluorescence to establish the receptor profiles of frequently-used cell lines characterized by different levels of heregulin receptor subunits. It was observed that HerPBK10 underwent substantially greater cell binding and uptake in HER2+ human breast cancer cells while minimal to negligible levels of binding and uptake were detected from HER2− cells. Using in vivo fluorescence imaging, it was observed that the targeting ligand used here specifically accumulates at HER2+ tumor tissue in mice while evading accumulation in other tissues. It was also observed that HerPBK10 could mediate the uptake of a Cy3-labeled oligonucleotide in HER2+ cells. The formation of noncovalent conjugates resulting from incubating HerPBK10 with siRNA was verified by the observation that siRNA electromobility dose-dependently decreased as HerPBK10 concentration increased. Ultrafiltration of conjugates under high speed centrifugation demonstrated that free siRNA could be separated from siRNA bound to the HerPBK10, and also indicated that the conjugate can withstand high shear forces without releasing the siRNA molecule. Targeted conjugates delivering anti-Her2 siRNA were added to HER2+ human breast cancer cells in culture, and yielded specific gene "knock-down" in target cells. Associated with this reduction was substantial target cell death. Depending on the cell line, up to 85% reduction was observed in HER2+ cell survival whereas HER2− cells receiving the targeted conjugate were little affected. HerPBK10 also augmented liposomal delivery of siRNA: when combined with liposome-coated siRNA, HER2+ cell numbers were considerably reduced whereas HER2− cell numbers showed only slight to negligible reduction. SiRNA Lipoplexes alone (lacking HerPBK10) only modestly to negligibly reduced the survival of both HER2+ and HER2− cells. Altogether, these findings indicate that HerPBK10 enables missile-like delivery of siRNA, resulting in targeted cell death.

Example 2

Description

This invention is designed to direct RNA interference (RNAi) to target cells. In one embodiment, the invention is comprised of two components that self-assemble into one targeted complex. In one form, the first component (Unit A) is a unique cell-penetrating carrier that can bind and enter target cells (FIG. 1). The second component (Unit B) may be a double-stranded nucleic acid that binds to the first component via electrostatic interactions (FIG. 1).

In one embodiment, the carrier is comprised of three main segments: 1. a unit designed to bind to specific target cells (FIG. 1, "L"); 2. a unit designed to mediate penetration into the interior of target cells (FIG. 1, "MP"); 3. a unit that can interact with nucleic acids designed to mediate RNAi (FIG. 1, "D").

In another embodiment, the nucleic acid may be comprised of: small interfering RNA (siRNA) of any length made from either synthetic or biological sources, small hairpin RNA (shRNA) of any length, complimentary oligonucleotides of any length, etc., to mediate RNAi in target cells. The nucleic acid may also contain any type of modification (i.e. addition of phosphate groups, etc) that may enhance its therapeutic efficacy.

The feasibility of this new type of therapeutic has been tested on HER2+ breast cancer in vitro and in vivo. To target HER2+ breast cancer, Unit A may be comprised of a protein called HerPBK10 (FIG. 2). HerPBK10 may contain the receptor binding domain of heregulin fused to the cell penetrating adenovirus penton base protein modified by a carboxy (C)-terminal decalysine (FIG. 2). The 'Her' segment of HerPBK10 may be obtained from the receptor binding domain of heregulin-_lpha, which binds specifically to HER2/HER3 or HER2/HER4 subunit heterodimers. Although heregulin interacts directly with HER3 or HER4, but not HER2, ligand affinity is greatly enhanced by HER2. Thus, tumor cells that over-express HER2 (known as HER2+ tumor cells) are ideal candidates for heregulin-directed targeting.

The membrane penetrating activity of the adenovirus serotype 5 (Ad5) penton base protein is incorporated into the 'PB' segment of HerPBK10 to facilitate penetration into target cells. The 'K10' segment is comprised of 10 lysine residues, whose positive charge can facilitate the transport of negatively charged molecules, such as nucleic acids, by electrophilic interaction.

Example 3

Novel Embodiments

The targeted RNAi delivery system enables the utilization of recombinant pathogen proteins modified for missile-like delivery and penetration of the RNAi therapeutic into target cells. This system is modular in its design, thus the cell targeting ligand may be exchanged for other ligands, depending on the cell targeted. In its practically applied form for tumor targeting and treatment, siRNA containing secondary modifications may be used to induce target cell induction of anti-tumor cytokines, and thus enhance tumor toxicity. The latter feature is unique to the method of use presented here, as sequence-independent cytotoxicity elicited by siRNA is currently considered an undesirable side effect by the research community at large. Here, this feature is exploited to enhance tumor toxicity by targeting the siRNA to tumor cells via the delivery agent.

Example 4

Figure 3A:
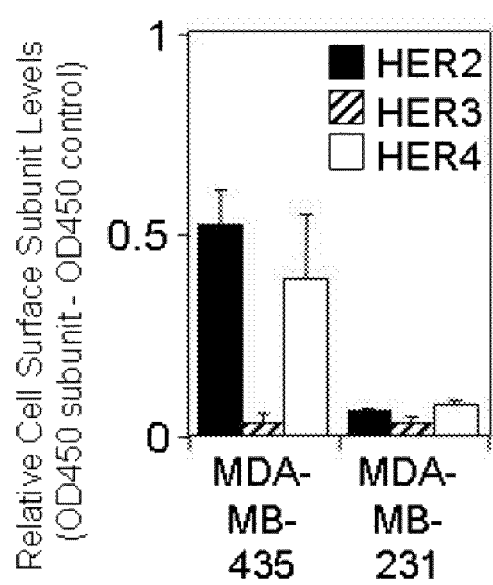
FIG. 3 depicts, in accordance with an embodiment herein, HerPBK10 cell binding and entry. A, Relative cell surface levels of HER subunits on MDA-MB-435 (HER2+) and MDA-MB-231 (HER2−) human breast cancer cells. Cells growing on 96-well plates were incubated with anti-HER subunit antibodies followed by HRP-conjugated secondary antibodies using standard ELISA procedures. Relative cell numbers were measured by crystal violet staining and quantified by measuring crystal violet absorbance at 590 nm. Relative subunit levels are reported as the ELISA signal of each cell population normalized by the relative cell number, or Abs 450 nm/590 nm. B, Binding and uptake of HerPBK10 in HER2+ and HER2− cell lines. At 2 days after plating on coverslips in 24 well dishes, cells were incubated with 5 ug HerPBK10/well in Buffer A on ice for 1 h to promote receptor binding but not internalization, then washed twice with buffer A to remove free protein, and incubated at 37° C. for the indicated time points to promote endocytosis. At each time point, separate wells of cells were washed with PBS/Mg 3-times then fixed in 4% PFA for 15' at RT and processed for immunohistochemistry by standard methods. Images were captured using a Leica laser-scanning confocal fluorescence microscope (Leica Microsystems, Wetzlar, Germany) Red, actin; Blue, nucleus; Green, HerPBK10. Bar=~10 microns.
Figure 3B:
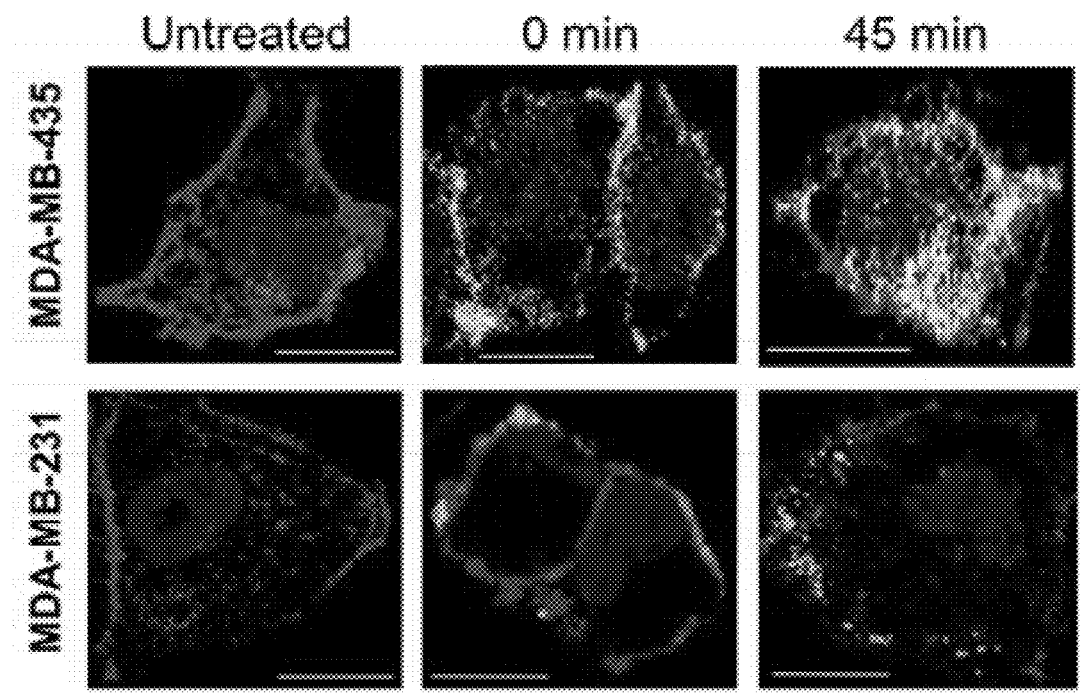

The Targeted Carrier Protein, HerPBK10, Undergoes High Cell Binding and Entry of HER2+ but not HER2− Human Breast Cancer Cells To verify the specificity and internalization activity of HerPBK10 on human breast cancer cells, we treated HER2+ (MDA-MB-435) and HER2− (MDA-MB-231) cells in culture with HerPBK10 and observed the cell binding, internalization, and intracellular trafficking activities using immunofluorescence and confocal microscopy. MDA-MB-435 cells display considerably higher cell surface levels of HER2/4 subunits compared to MDA-MB-231 cells, which display negligible to nearly undetectable HER2 levels (FIG. 3A). Accordingly, it was observed that MDA-MB-435 cells displayed substantially greater HerPBK10 bound to the cell surface than MDA-MB-231, while HerPBK10 fluorescence was minimal to negligible on MDA-MB-231 cells. (FIG. 3B). HerPBK10 internalization into each cell line likewise reflected the level of cell binding, with substantial protein uptake observed in MDA-MB-435 cells while minimal to negligible levels of uptake were detected in MDA-MB-231 cells (FIG. 3B).

Example 5

HerPBK10 Transports Labeled Oligonucleotide into MDA-MB-435 Cells

Figure 4:
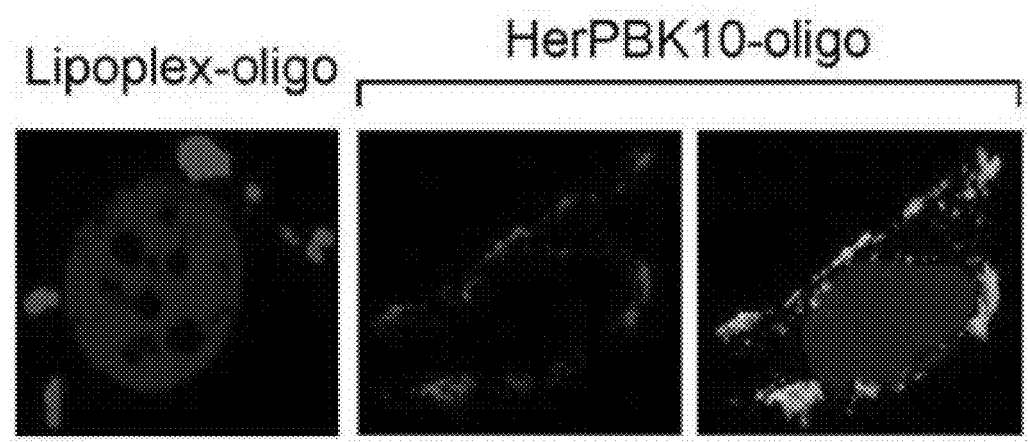
FIG. 4 depicts, in accordance with an embodiment herein, HerPBK10 transports a labeled oligonucleotide in MDA-MB-435 cells. A Cy3-labeled oligonucleotide (50 pmol) was incubated with either HerPBK10 (5 ug) or a commercial transfection reagent (Lipofectamine 2000; Invitrogen, Carlsbad, Calif., USA) in 0.1 M HEPES/Optimem I (Invitrogen; Carlsbad, Calif., USA) for 20 minutes at RT. The resulting mixture was added to MDA-MB-435 cells and incubated for 1 h at 37° C. Cells were fixed in 4% PFA for 15' at RT and processed for immunohistochemistry and confocal microscopy as described in FIG. 1.

To examine the capacity of HerPBK10 to facilitate direct transport of small nucleic acids into cells, a Cy3-labeled oligonucleotide (Cy3-oligo) was incubated with HerPBK10 to mediate assembly via electrophilic interaction, then the resulting complex was added to MDA-MB-435 cells in culture. Confocal fluorescence microscopy of treated cells shows that HerPBK10 and the Cy3-oligo colocalize after uptake (FIG. 4), demonstrating that the oligonucleotide is bound to HerPBK10 after cell entry. As it is possible that the oligo may enter cells by fluid-phase uptake with HerPBK10, the binding interaction between small nucleic acids and HerPBK10 was examined more closely.

Example 6

Recombinant Targeted Proteins Form a Stable Assembly with siRNA

Figure 5:
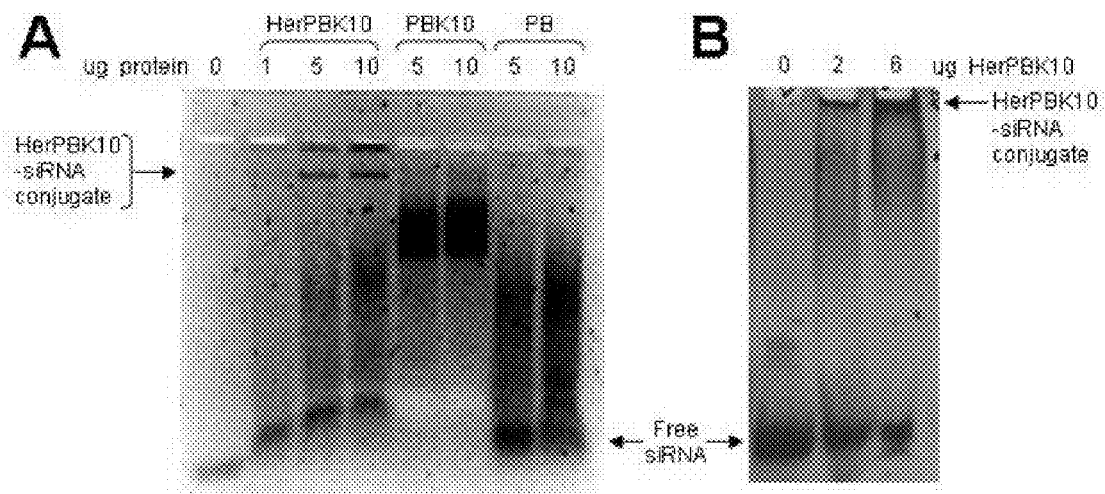
FIG. 5 depicts, in accordance with an embodiment herein, HerPBK10 directly interacts with siRNA via electrophilic binding. A, 50 pmol siRNA from Invitrogen (Carlsbad, Calif., USA; SEQ ID NO: 6 ErbB2 RTF primer: TCTGACGTGCCAGTGTGAA, and SEQ ID NO: 7 ErbB2 RTR primer: TGCTCCCTGAGGACACATCA) was incubated with 0, 5, 10 ug of protein (PB, PBK10 or HerPBK10) in 50 ul of 0.1M Hepes/Optimem I buffer for 20' at RT, then subject to electrophoresis on a 2% agarose gel (1:1, agarose: SeaPlaqiue GTG, low melting agarose). After electrophoresis, the gel was stained ethidium bromide to visualize siRNA and siRNA-protein complexes. B, 50 pmol siRNA was incubated with 0, 2 and 6 ug HerPBK10 protein in 0.1 MHepes/OptimemI buffer for 20' at RT, then subject to 6% PAGE under native (non-denaturing) conditions. The gel was stained with ethidium bromide to visualize siRNA and siRNA-protein complexes.

One goal was to assemble a noncovalent siRNA conjugate. Thus, the interaction of a commercial siRNA duplex with HerPBK10 was examined by gel mobility shift assay. The duplex, which was obtained from Invitrogen (Carlsbad, Calif., USA), has been established elsewhere to specifically eliminate HER2 transcripts and thus induce apoptosis (Choudhury et al., 2004; Faltus et al., 2004). Constant concentrations of the HER2 siRNA were incubated with increasing concentrations of HerPBK10 and each mixture was then analyzed on either an agarose or acrylamide gel. A dose-dependent decrease in siRNA electromobility was evident as HerPBK10 concentration increased (FIGS. 5A and B). Likewise, the protein, PBK10, which lacks the Her domain, also dramatically decreased siRNA mobility, while PB did not (FIG. 5A), indicating that the decalysine, or 'K10', domain is responsible for binding the siRNA. As previously demonstrated using plasmid DNA and labeled oligonucleotides, both HerPBK10 and PBK10 can bind nucleic acids likely via electrophilic interactions between the positively charged polylysine and the negatively charged nucleic acid phosphate backbone (Medina-Kauwe et al., 2001a; Medina-Kauwe et al., 2001b).

Figure 6:
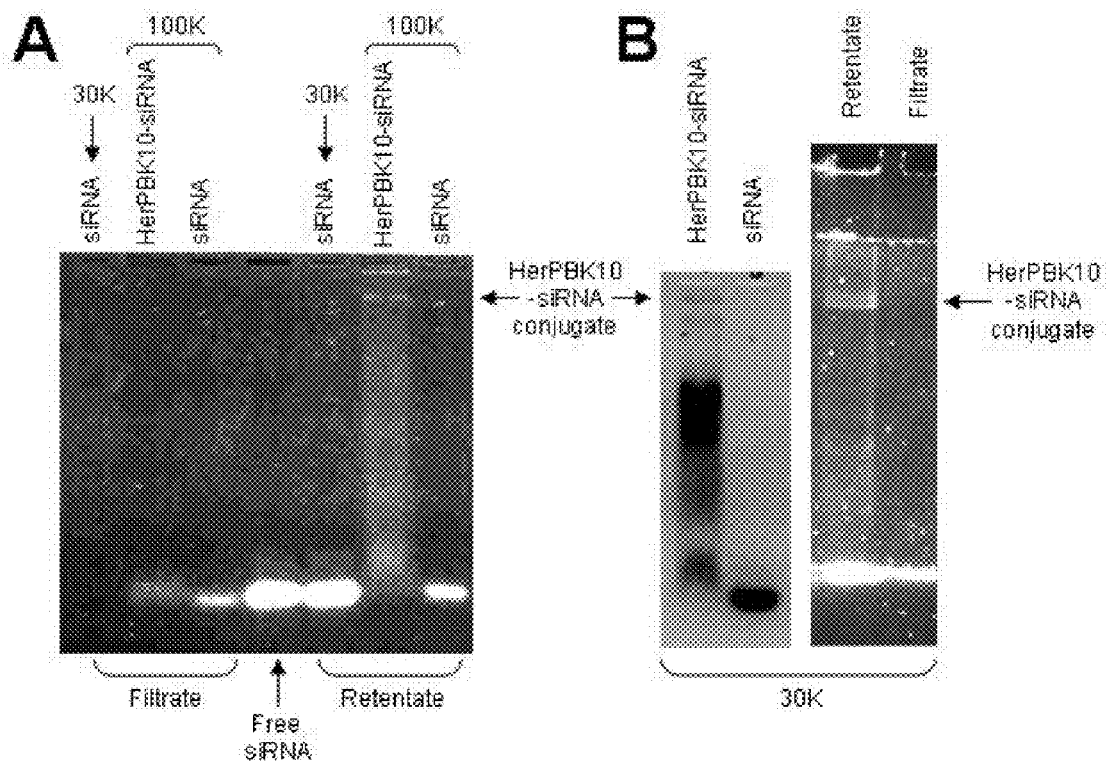
FIG. 6 depicts, in accordance with an embodiment described herein, HerPBK10-siRNA form stable conjugates that can be isolated by ultrafiltration. Conjugates were made in 0.1M Hepes/Optimem I buffer for 20'-RT, as described above. The siRNA alone or HerPBK10-siRNA conjugates were applied 30K or 100K centrifugal filter devices (Nanosep; Pall Filtron, East Hills, N.Y., USA) following the manufacturer's protocol. Filtrates and retentates were collected and loaded onto either a 2% agarose (A and B, left panel) or 5% PAGE/native gel (B, right panel). Gels were stained for Et-Br to visualize siRNA and siRNA-protein complexes.

To demonstrate that the protein-siRNA complex formed a stable assembly that could be separated from free siRNA, the mixture was subject to high speed centrifugation onto filter membranes with specified molecular weight exclusion ranges of either a 30K or 100K molecular weight cut-off (mwco). Both HerPBK10-siRNA and free siRNA are retained on 30K mwco filters (FIGS. 6A and B) whereas the 100K filter retains the conjugate but allows the free siRNA to flow through (FIG. 6A). The ability of the conjugate to withstand high speed centrifugation, as determined by low to no detection of free siRNA in 100K filtrates (FIG. 6A), indicates that this conjugate can withstand high shear forces without releasing the siRNA molecule.

Example 7 siRNA Missiles Mediate Knock-Down in HER2+ but not HER2− Cells in Culture

Figure 7:
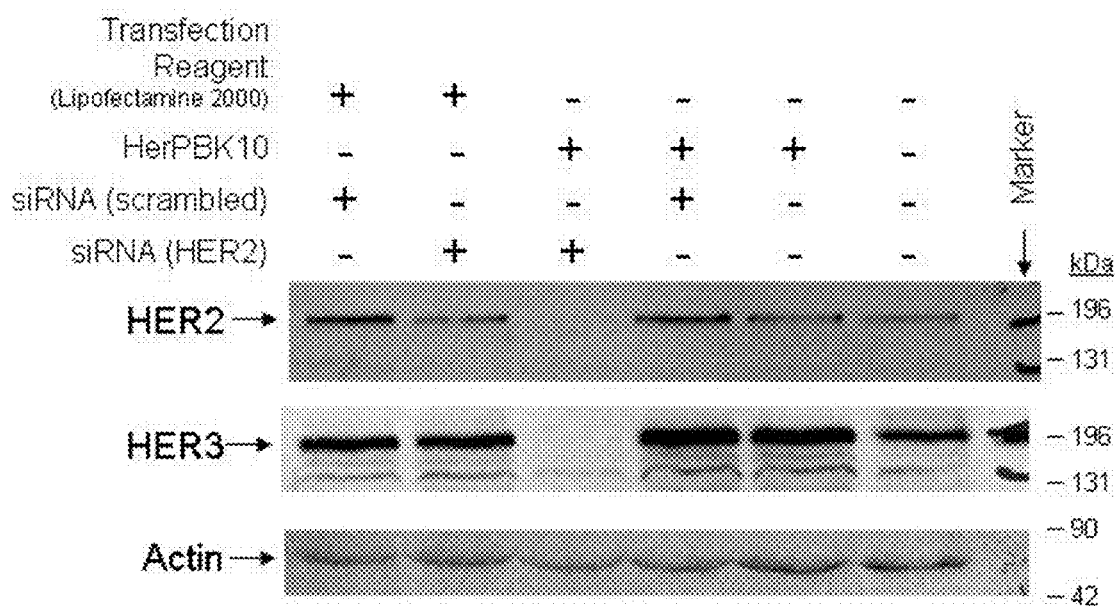
FIG. 7 depicts, in accordance with an embodiment described herein, HerPBK10 facilitates siRNA-mediated knock-down in targeted HER2+ cells. At 2 days after plating, MDA-MB-435 cells were treated with either siRNA lipoplexes or HerPBK10-siRNA conjugates in complete media and incubated for 48 h at 37° C., after which the media was exchanged for fresh media. At 96 h after transfection, cells were analyzed for HER2 and/or HER3 subunit levels by Western blotting. Lipoplexes were formed by incubating 100 pmol siRNA with Lipofectamine 2000 in Optimem I, following the manufacturer's protocol. HerPBK10-siRNA conjugates were formed by incubating 100 pmol siRNA with 20 ug HerPBK10 at 1:2 or 1:4 (siRNA: protein) molar ratios in 100 mM Hepes in Optimem I buffer, at RT for 20' before adding to cells in complete media. For Western blotting, cells were lysed with RIPA buffer (150 mM NaCl, 50 mM Tris base pH 8.0, 1 mM EDTA, 0.5% sodium deoxycholate, 1% NP40, 0.1% sodium dodecyl sulfate, 1 mM DTT, 1 mM PMSF, and 1 mM Na3VO4) supplemented with complete Protease Inhibitor cocktail. Protein concentration was determined using a Bio-Rad protein assay reagent. The cell lysate proteins were separated by 10% PAGE (25 ug of total protein loaded per well), followed by electrotransfer (140 mA for 2 hours) to a nitrocellulose membrane (Hybond-ECL; Amersham Biosciences, Piscataway, N.J., USA). The membranes were blocked in PBS containing 3% dry milk for 1 h at room temperature with constant agitation. The blotted nitrocellulose was incubated with 1 ug/ml Anti-ErbB2/Her2 or Anti-erbB3/Her3 (Upstate/Millipore, Billerica, Mass., USA) diluted in PBS-milk agitating at 4° C. overnight. The membranes were washed twice with water, and incubated with secondary antibody for 1.5 hours at room temperature. The membranes were washed twice with water, then with PBS-0.05% Tween for 3-5 minutes. The nitrocellulose was rinsed with water 4-5 times, and processed for chemiluminescence.

To determine whether the HerPBK10-siRNA conjugate is capable of mediating specific gene "knock-down" in target cells, the conjugate delivering HER2 siRNA was compared to a standard transfection agent (Lipofectamine 2000) on MDA-MB-435 cells in culture. Knock-down of HER2 was analyzed by immunoblotting of cell lysates. The transfection agent mediated very modest reductions of HER2 whereas the targeted conjugate reduced HER2 to undetectable levels (FIG. 7). A scrambled siRNA had no effect on HER2 levels when delivered by either the transfection agent or HerPBK10 (FIG. 7). Interestingly, HER3 levels were also nearly completely reduced by the targeted conjugate whereas the transfection agent had no detectable effect on this subunit (FIG. 7), raising the possibility that protein levels of HER2 may regulate those of HER3. HerPBK10 alone had no effect on HER2 and HER3 levels (FIG. 7), thus ruling out the possibility that HerPBK10 may somehow induce down-regulation of the receptor subunits by virtue of its binding and internalization through HER.

Figure 8:
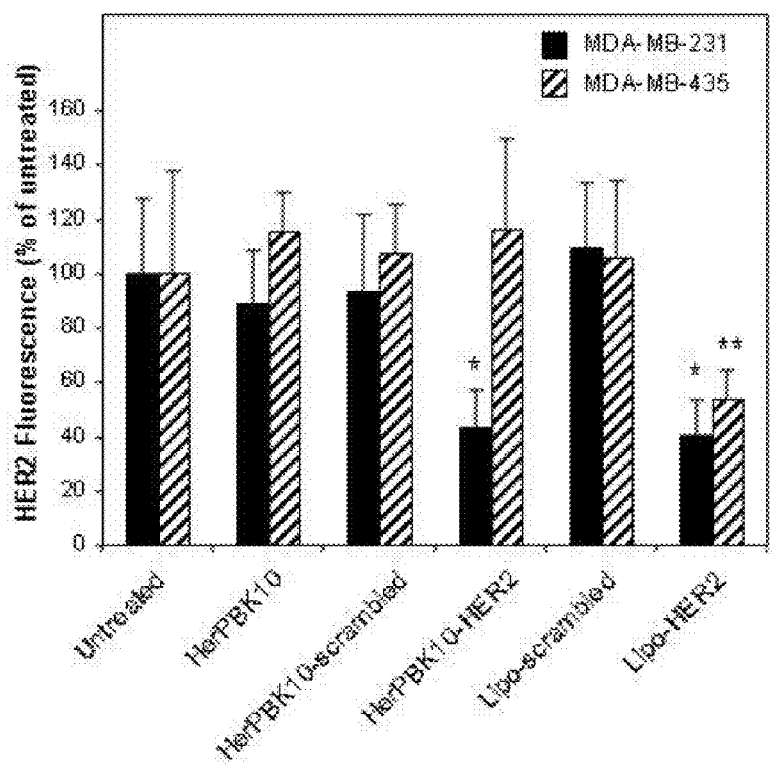
FIG. 8 depicts, in accordance with an embodiment herein, HerPBK10 mediates siRNA delivery and knock-down to HER2+ but not HER2− cells. MDA-MB-435 and MDA-MB-231 cells were plated and treated with either siRNA lipoplexes or HerPBK10-conjugates as described in FIG. 5. At 96 h after treatment, cells were fixed and processed for immunohistochemistry using a HER2 antibody. Significant differences were determined using two-tailed t tests with unequal variance. *, P<0.00002 (compared to untreated); **, P<0.04 (compared to untreated).

HER2 immunofluorescence was compared between MDA-MB-435 cells and MDA-MB-231 cells when each was treated with either the targeted conjugate or transfection reagent. MDA-MB-231 are not HER2 deficient but rather express HER2 intracellularly but not on the cell surface. Whereas the transfection reagent delivering HER2 siRNA mediated 50-60% reduction of HER2 in both cell lines, the targeted conjugate reduced HER2 nearly 60% in MDA-MB-435 cells but had little to no effect in MDA-MB-231 cells (FIG. 8). HerPBK10 alone and targeted conjugate delivering scrambled siRNA had little to no effect on either cell line. Importantly, all siRNA delivery experiments in culture were performed in complete (i.e. serum-containing) media, thus demonstrating that serum will not have an inhibitory effect on the conjugate.

Example 8

Figure 9A:
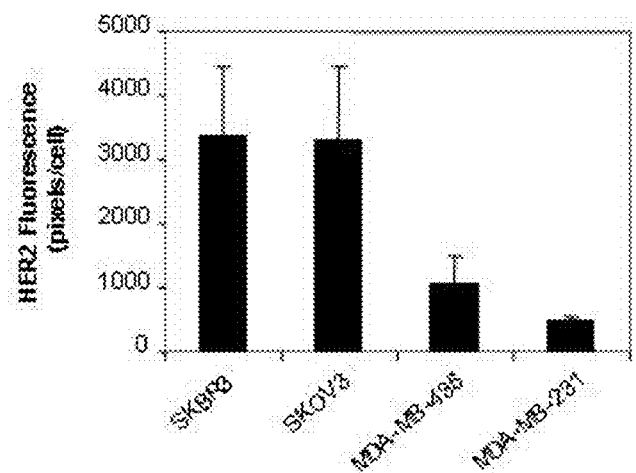
FIG. 9 depicts, in accordance with an embodiment herein, HerPBK10 mediates siRNA delivery to high HER2-expressing cell lines, and augments lipoplex-mediated knock-down. A, HER2 levels of SKBR3 and SKOV3 cell lines in comparison to MDA-MB-435 and MDA-MB-231 cells. Cells were processed for immunohistochemistry using a HER2 antibody and scored for HER2 levels as described in FIG. 1. B, Immunofluorescence of HER2 protein after delivery of lipoplexes or targeted conjugates. SKBR3 and SKOV3 cells were plated and treated with either siRNA lipoplexes or HerPBK10-conjugates as described in FIG. 5. At 96 h after treatment, cells were fixed and processed for immunohistochemistry using a HER2 antibody. Conjugates containing HerPBK10 with lipoplexes were formed by incubating either 1.5, 5, or 10 micrograms of HerPBK10 with siRNA lipoplexes, equating a final molar ratio of either 1:1:1, 1:2:1, or 1:4:1 (siRNA:HerPBK10:Lipofectamine), respectively. These complexes were formed by incubating HerPBK10 with lipoplexes at RT for an additional 20 min after lipoplex formation, then complexes were added to the cells. Control cells were incubated in 100 mM HEPES/Optimem I buffer alone, or with HerPBK10 only or siRNA only. Cells received either HER2/neu-specific or scrambled siRNA. C, Quantification of HER2 knock-down. Cells were scored for HER2 immunofluorescence as described in FIG. 1. Statistical significance was determined using a two-tailed t test at unequal variance. *, $P<0.00006$ (compared to untreated); **, $P<0.04$ (compared to untreated).
Figure 9B:
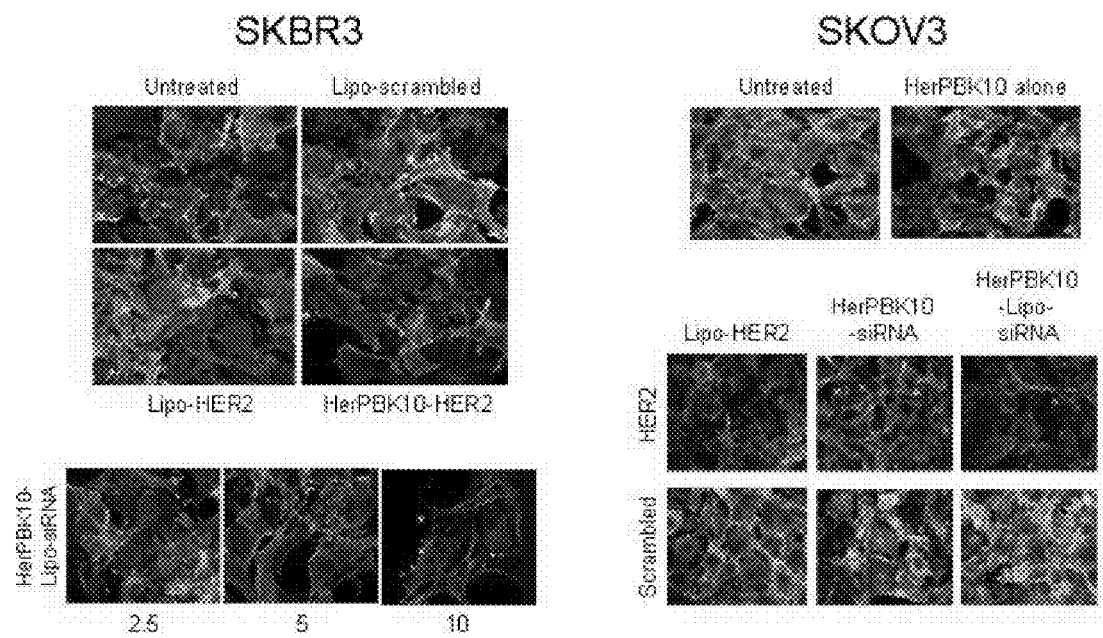
Figure 9C:
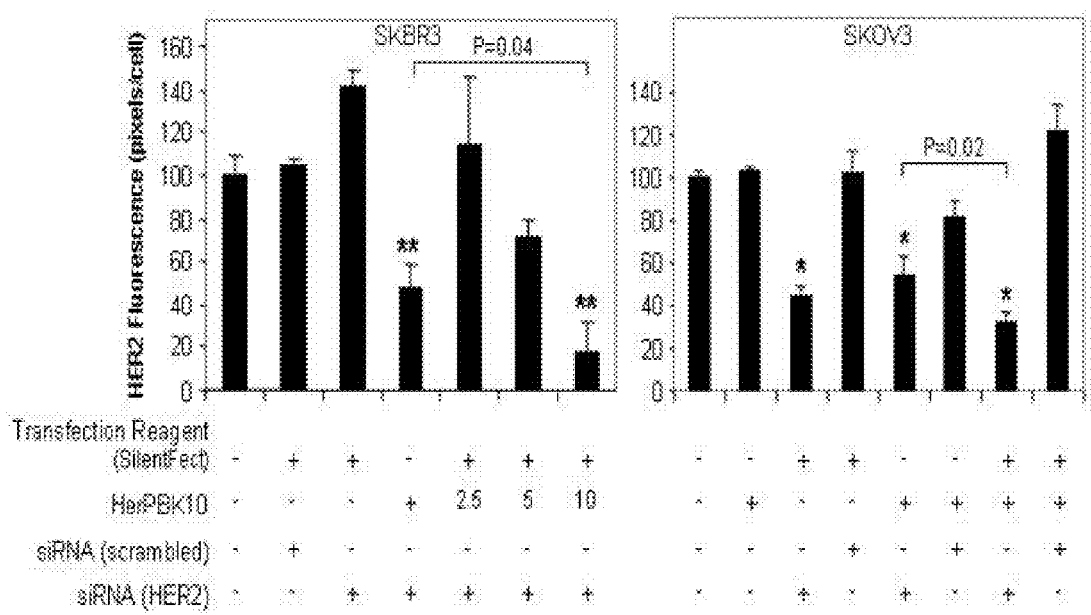

HerPBK10 Augments Lipoplex-Mediated siRNA Delivery in High HER2-Expressing Cells The inventors also examined whether conjugate activity could be expanded to other HER2+ cell lines. Using immunofluorescence, it was determined that SKBR3 and SKOV3 cell lines expressed nearly 3-times higher HER2 compared to MDA-MB-435 cells (FIG. 9A). Whereas a transfection reagent delivering HER2 siRNA had no detectable effect on HER2 levels in SKBR3 cells, the targeted conjugate reduced levels nearly 50% (FIG. 9B). The transfection reagent used here is specified for siRNA delivery (Silentfect; Bio-Rad Laboratories, Hercules, Calif., USA). To see if HerPBK10 could improve delivery by the transfection reagent, increasing concentrations of HerPBK10 were incubated with the lipoplex, resulting in a dose-dependent decrease (up to 80-85% reduction) in HER2 when added to SKBR3 cells (FIG. 9B). The transfection reagent fared better in SKOV3 cells, resulting in nearly 50-55% reduction of HER2 whereas the targeted conjugate mediated nearly 50% reduction (FIG. 9C). Combining HerPBK10 with the lipoplex augmented HER2 reduction, resulting in nearly a 70% HER2 knock-down (FIG. 9C).

Example 9

Serum Stability: HerPBK10 Protects the siRNA from Serum Nucleases

Figure 10:
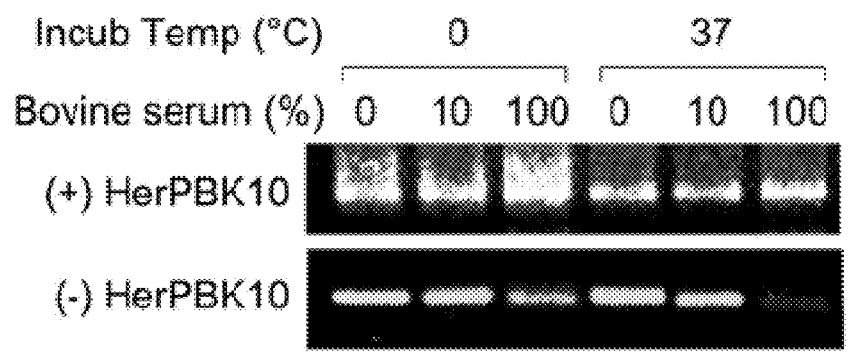
FIG. 10 depicts, in accordance with an embodiment herein, HerPBK10 protects siRNA in serum. Free siRNA alone (60 pmoles) or pre-incubated with HerPBK10 (2 ug, for 30 min at RT) was incubated in either complete media (10% bovine serum) or whole (100%) serum at 37° C. for 1 h, then assessed by agarose gel electrophoresis.

Nucleases present in serum and cells can degrade nucleic acid payloads and thus potentially reduce siRNA delivery (Medina-Kauwe et al., 2005). We examined the stability of siRNA conjugates in whole serum. HerPBK10-siRNA or siRNA alone were incubated in either 100% bovine serum or cell culture media (containing 10% serum) for 1 h at 37° C. and then assessed by agarose gel electrophoresis to examine the state of the siRNA. Ethidium bromide staining of the agarose gel identifies the siRNA molecular size and relative concentration. Ethidium bromide staining is nearly absent from samples in which the free siRNA was incubated with 100% serum, suggesting that the siRNA molecule is degraded by serum nucleases (FIG. 10). The same samples in which the siRNA is complexed with HerPBK10 shows that the siRNA molecule is intact and appears to be protected from serum nucleases (FIG. 10).

Example 10

Figure 11:
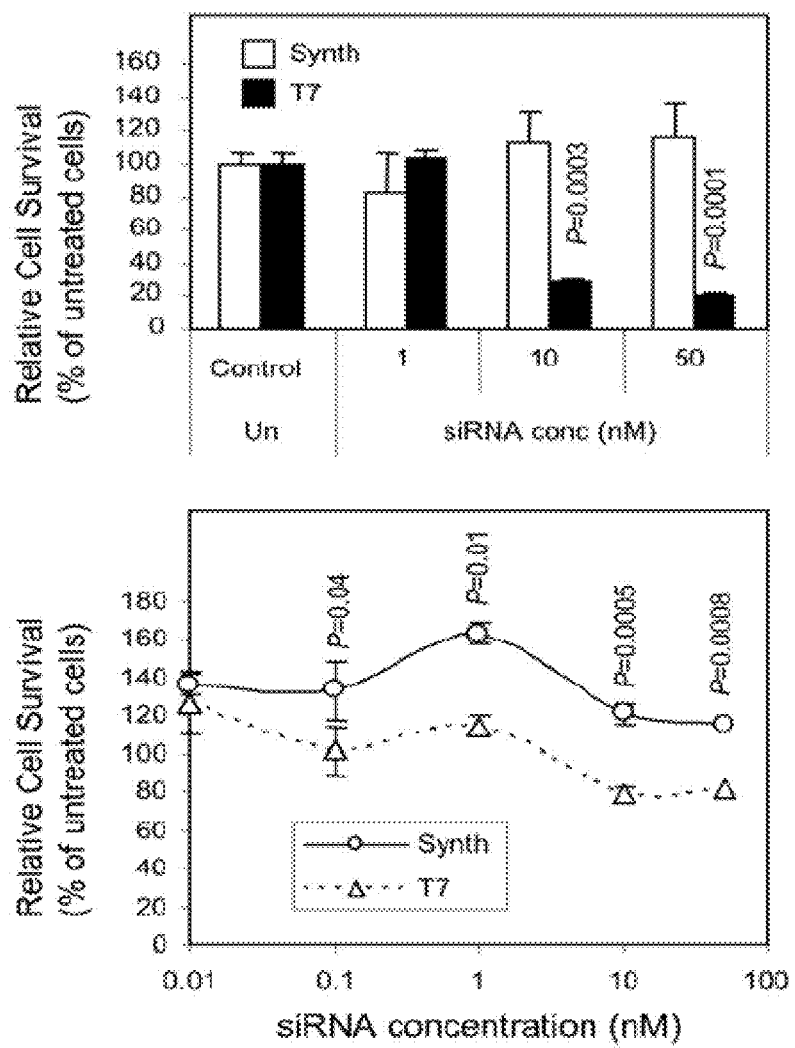
FIG. 11 depicts, in accordance with an embodiment herein, the effect of synthetic (Synth) vs T7-polymerized (T7) siRNA on cell survival. Indicated concentrations of anti-HER2 siRNA were transfected into MDA-MB-435 cells using (A) a commercial transfection agent (RNAimax) or (B) HerPBK10 (pre-assembled with siRNA at 4:1 charge ratio siRNA:protein), and assayed for cell survival using crystal violet stain at 96 h after treatment. HerPBK10-siRNA complexes were assembled by co-incubating siRNA and HerPBK10 in 100 mM Hepes in Optimem I buffer at RT for 30 min, then free siRNA removed by ultrafiltration through a 100 mwco membrane before adding to cells. Control cells were incubated in 100 mM HEPES/Optimem I buffer alone. Un, untreated cells. P values reflect differences between synthetic vs T7 siRNA. Significant differences determined by 2-tailed t tests.

T7-Transcribed siRNA Induces Higher Breast Cancer Cell Cytotoxicity than Synthetic siRNA Previously, it was found that HerPBK10-siRNA complexes induce cell-specific silencing of target HER2 gene transcripts. The siRNA used in those studies were obtained from a commercial source as pre-made, synthetic molecules (Dharmacon). As published findings indicate that T7 transcribed siRNA induce non-specific but potent cytokine-mediated cytotoxicity (Kim et al., 2004), the inventors compared the cytotoxicity of T7 transcribed vs synthetic anti-HER2 siRNA on HER2+ cells. The inventors acquired a 21 nucleotide (nt) synthetic anti-HER2 (ErbB2) siRNA and also produced a T7-transcribed molecule (Silencer siRNA construction kit; Ambion) using the same sequence. Both were transfected into MDA-MB-435 human breast cancer cells in vitro at 1, 10, and 50 nM final siRNA concentrations and the cells assayed for survival at 96 h after treatment. Whereas the synthetic siRNA had no effect on cell survival, the 10 and 50 nM concentrations induced substantial cell death (FIG. 11A). Similarly, when each siRNA is pre-assembled with HerPBK10, treated cells undergo significantly reduced cell survival after receiving the T7-transcribed siRNA compared to the synthetic siRNA (FIG. 11B).

Example 11

Figure 12:
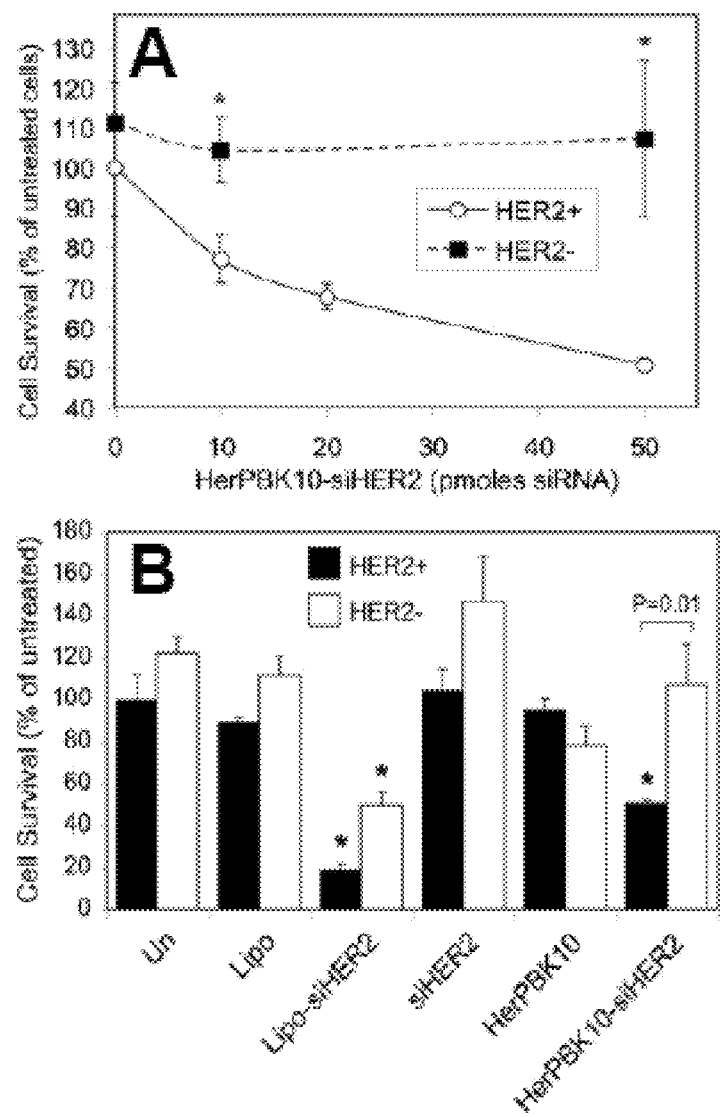
FIG. 12 depicts, in accordance with an embodiment herein, survival (assessed by crystal violet stain) of MDA-MB-435 (HER2+) and MDA-MB-231 (HER2−) cells after receiving (A) dosed HerPBK10-siRNA conjugates, and (B) 50 pmoles siHER2 (anti-HER2 siRNA) by non-specific (Lipo-mediated) or targeted (3 ug HerPBK10) complexes in 100 uL complete media/well of a 96-well plate. Complexes were prepared as described in FIG. 2. Un, untreated. In A, *, $P<0.02$ (HER2+ vs HER2− cells). In B, *, $P<0.05$ (compared to untreated). Significant differences determined by 2-tailed t tests.

SiRNA-Facilitated Cytotoxicity can be Targeted to HER2+ but not HER2− Cells by HerPBK10-Mediated Delivery As the cytotoxicity induced by T7-transcribed siRNA is thought to be non-sequence specific, the inventors explored whether this effect could be targeted using the HerPBK10 protein. Previous studies show that HerPBK10 binds and enters MDA-MB-435 but not MDA-MB-231 cells, whereas commercial transfection reagents are not expected to be as discriminating with respect to receptor-targeting capacity. Several different doses of HerPBK10-siRNA complexes added to MDA-MB-435 (HER2+) and MDA-MB-231 (HER2−) cells produced a dose-dependent reduction in survival of the HER2+ cells (FIG. 12A) but had little to no effect on HER2− cells (FIGS. 12, A & B). In contrast, siRNA delivered by a liposomal transfection reagent (Lipo-si-HER2) significantly reduced the survival of both HER2+ and HER2− cells (FIG. 12B). Transfection reagent alone (Lipo), siRNA alone (siHER2), and HerPBK10 alone (0.03 mg/mL) had negligible effect on both cell lines (FIG. 12B).

Example 12

Ligand-Directed siRNA Carrier Vehicle, HerPBK10, Targets HER2+ Tumors in Mice

To get a sense of the targeting ability of the ligand in vivo and establish an index of in vivo targeting, the inventors used a green fluorescent protein (GFP)-tagged ligand (GFP-Her), which has been used previously to demonstrate targeted receptor binding and endocytosis in HER2+ cells (Medina-Kauwe and Chen, 2002; Medina-Kauwe et al., 2000). Importantly, this ligand is identical to the 'Her' domain of HerPBK10. The inventors established HER2+ tumors in 6-8 week female nude mice via bilateral flank injections of MDA-MB-435 cells. When the tumors reached 250-300 mm$^3$ (~3-4 weeks after tumor cell implant), 3 nmoles of GFP-Her was injected via the tail vein. Mock injected mice received saline alone. Indicated tissues were harvested at 3.5 h after injection and imaged for GFP using a Xenogen IVIS three-dimensional small-animal in vivo imaging system (Xenogen, Alameda, Calif.). Preferential accumulation of GFP fluorescence was detected in the tumors over the other tissues. Low to negligible levels of fluorescence were detected in the liver and muscle, while GFP fluorescence was undetectable in the other tissues, including the heart. Tissues from mock-treated animals showed no fluorescence. To further assess the in vivo targeting capacity of HerPBK10, tumor-bearing mice received systemic administration of HerPBK10 labeled with a fluorescent molecule (S2Ga; (Agadjanian et al., 2006)). Mice were monitored for label circulation and biodistribution in real time using a small animal image acquisition system through the assistance of the Minimally Invasive Surgical Technologies Institute (MISTI) directed by Dr. Daniel Farkas at Cedars-Sinai Medical Center. Whereas the free, untargeted label exhibits distribution throughout most of the mouse (and, interestingly, appeared to be excluded from the tumors), labeled HerPBK10 exhibited preferential tumor accumulation in comparison to other regions of the body (except for the injection site). The occasional high retention of injected material at the injection site of the tail vein is mostly due to technical complications in which some of the material is accidentally injected into the tail muscle rather than wholly in the vessel. This effect can be alleviated as injection technique improves.

Example 13

Figure 13:
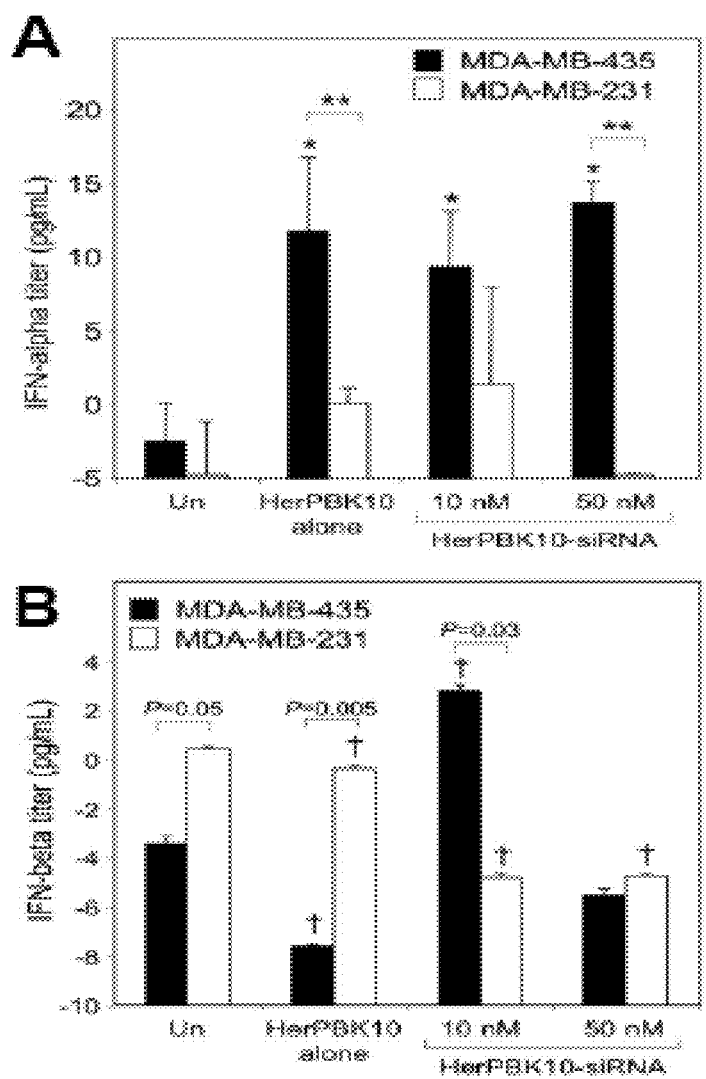
FIG. 13 depicts, in accordance with an embodiment herein, cytokine induction. Cells growing in 96-well plates ($5\times10^3$ cells/well) were treated with indicated concentrations (with respect to siRNA concentration) of HerPBK10-siRNA complexes or HerPBK10 (3 ug per well, at equivalent concentration to HerPBK10 in the 50 nM dose of complex). At 24 h after treatment, media was collected from above the cells and assayed for (A) IFN-alpha, or (B) IFN-beta titer by sandwich ELISA following manufacturer's protocol (PBL Biomedical Laboratories). *, $P<0.01$ (compared to untreated); **, $P=0.01$ (HER2+ vs HER2− cells); †, $P<0.05$ (compared to untreated). Statistical significances determined by 2-tailed t tests.
Figure 14:
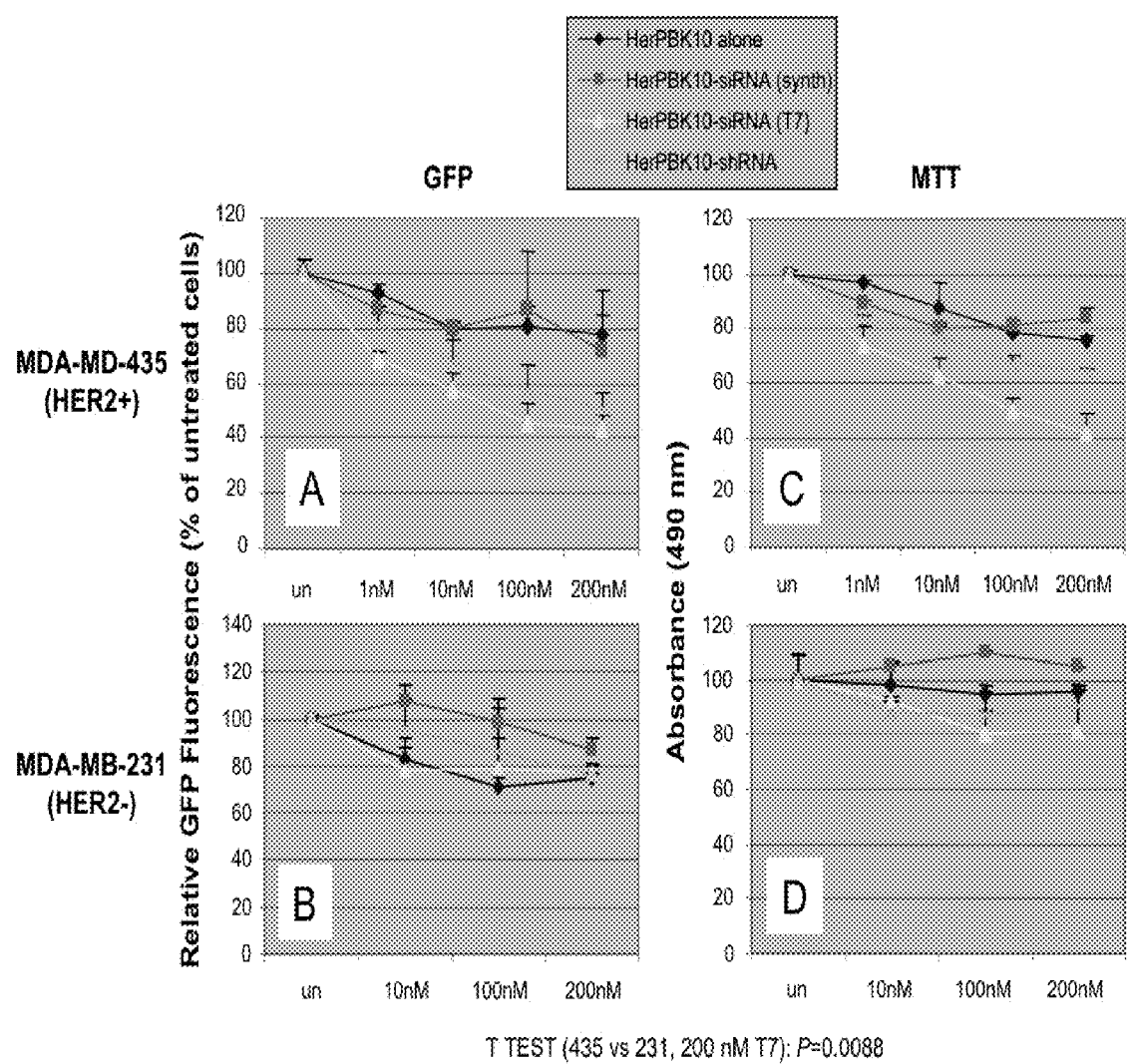
FIG. 14 depicts, in accordance with an embodiment herein, comparing of RNAi species. HerPBK10 was assembled with each RNAi species at a HerPBK10:nucleic acid molar ratio of 4 by co-incubation in 100 mM Hepes+ Optimem I buffer at RT for 30 min, then free RNAi species removed by ultrafiltration through a 100K mwco membrane before adding to separate wells of GFP-tagged MDA-MB-435 (HER2+; A & C) or MDA-MB-231 (HER2−; B & D) human cancer cells. Cells were assayed for GFP expression (A & B) and metabolic (MTT) activity (C & D) at 96 h after treatment.
Figure 15A:
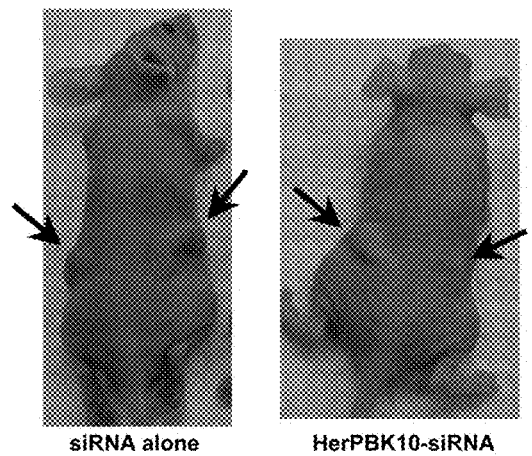
FIG. 15 depicts, in accordance with an embodiment herein, effect on tumor growth. Female (6-8 week) nude mice were inoculated with human HER2+ MDA-MB-435 cancer cells by subcutaneous flank injections of $1\times10^7$ cells per injection. At 4-6 weeks after implant, weekly measurements were taken to quantify tumor volume and track growth. Each tumor received an IT injection of either T7 transcribed anti-HER2 siRNA or HerPBK10-siRNA (1.5 nmoles final siRNA dose) on the second and third weeks of tumor monitoring. Complex was prepared as described in FIG. 14, A, representative mice at week 4 with tumors indicated by arrows. B, tumor volumes from mice receiving siRNA alone or HerPBK10-siRNA.
Figure 15B:
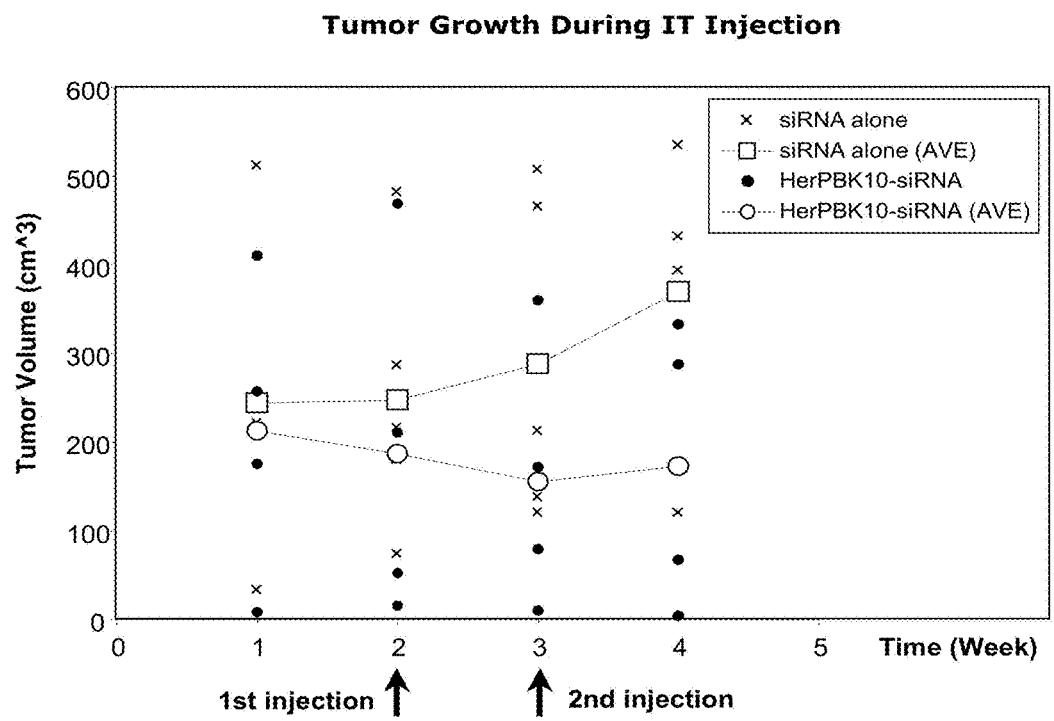
Figure 16:
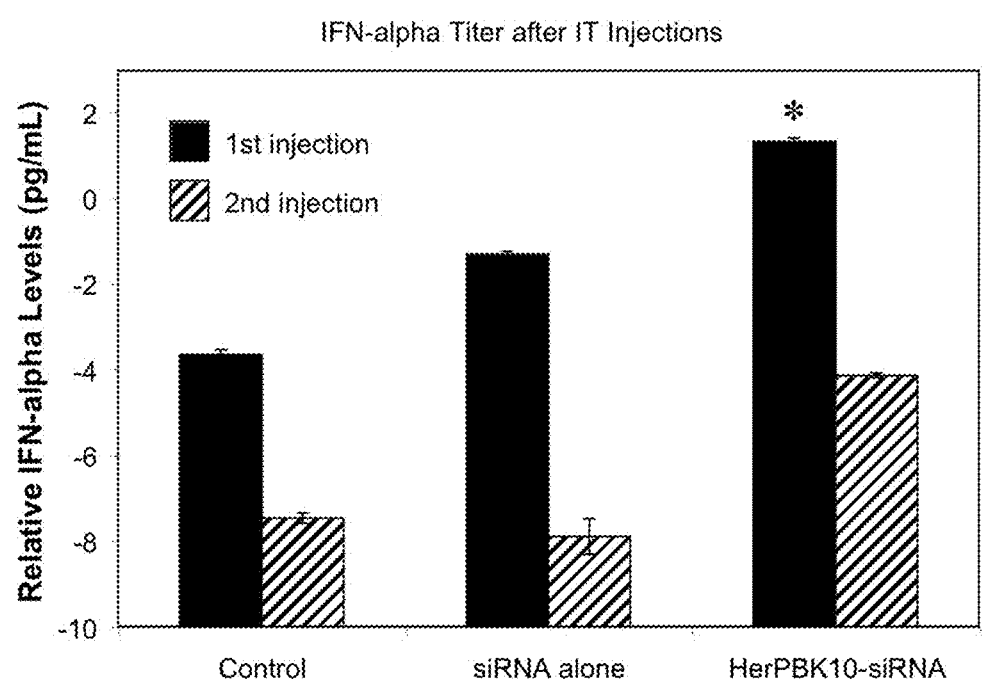
FIG. 16 depicts, in accordance with an embodiment herein, in vivo cytokine induction. Blood was collected from the mice treated in FIG. 15B at 24 h after each IT injection and relative IFN-alpha levels quantified by sandwich ELISA following manufacturer's protocol (PBL Biomedical Laboratories). Control, tumors receiving saline injections. *, $P=0.05$ compared to control (as determined by 2-tailed unpaired T test).
Figure 17:
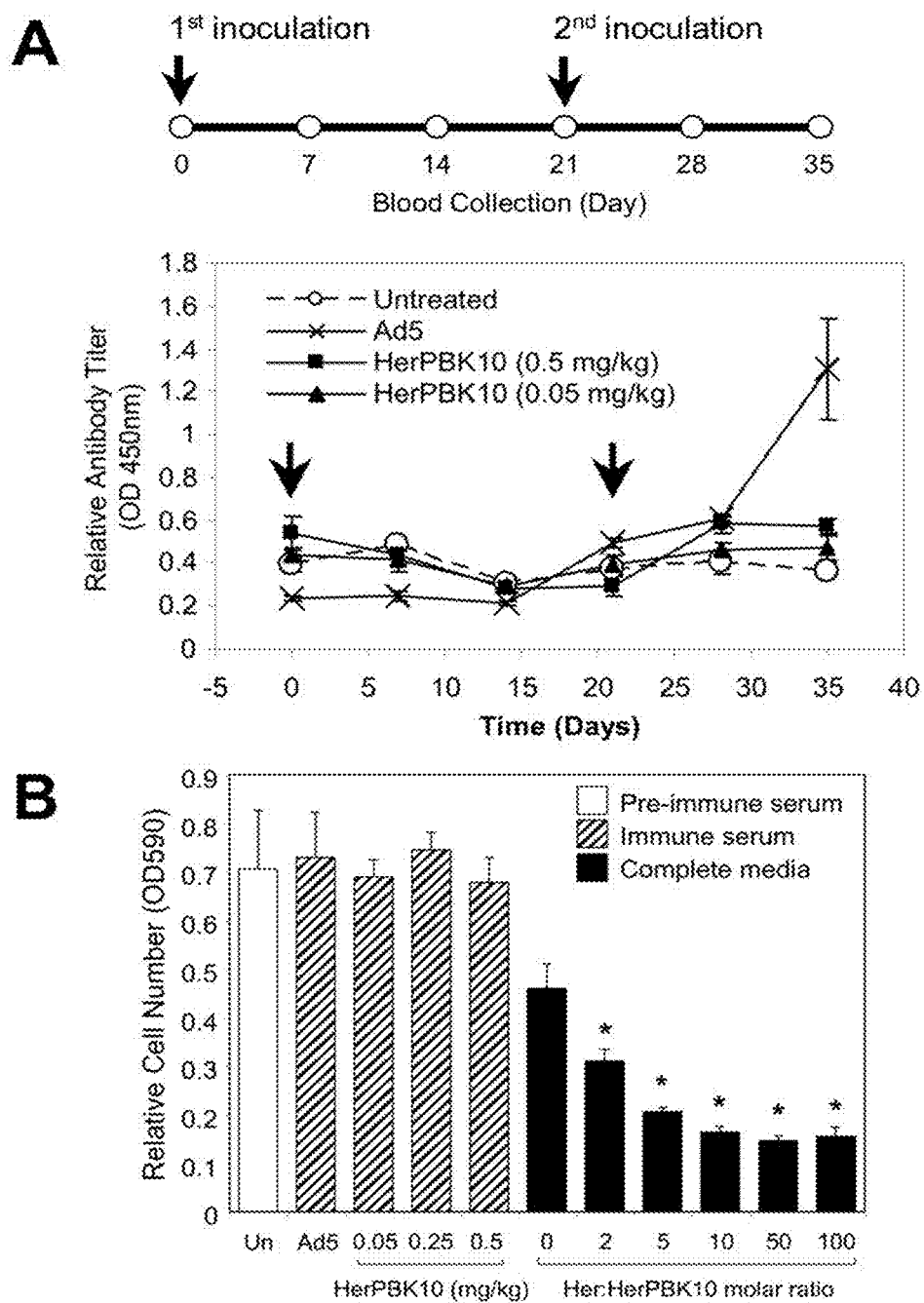
FIG. 17 depicts, in accordance with an embodiment herein, testing for neutralizing antibody induction. A, Immunocompetent (C57BL/6) mice received an initial subcutaneous inoculation of HerPBK10 protein (0.05 or 0.5 mg/kg) or Ad5-GFP ($1.2\times10^9$ pfu/mouse) followed by blood collection scheduled every seven days up to day 35 after the initial inoculation, as summarized by the upper time chart. On day 21, respective mice received a second inoculation of each corresponding reagent. Sera isolated from bleeds were assessed by ELISA for relative antibody titer produced against HerPBK10 (lower graph). Arrows denote days of antigen inoculation. N=4 mice per treatment group dose. B, Effect of immune sera on target cell binding. Ligand-receptor binding was tested by measuring the level of cell attachment to HerPBK10-coated plates in immune or pre-immune serum collected from mice in A. Cells suspended in either pre-immune serum, immune serum from Ad5 or HerPBK10-inoculated mice, or complete media containing 10% bovine serum but no mouse serum were incubated on HerPBK10-coated wells for 1 h at 37° C., followed by removal of free cells and measurement of attached cells by crystal violet assay. The level of receptor-specific binding was assessed on separate cells pre-incubated with competitive inhibitor (Her). Un, untreated mice. *, $P<0.01$ compared to cells attached in pre-immune serum, as determined by 2-tailed unpaired t test.
Figure 18:
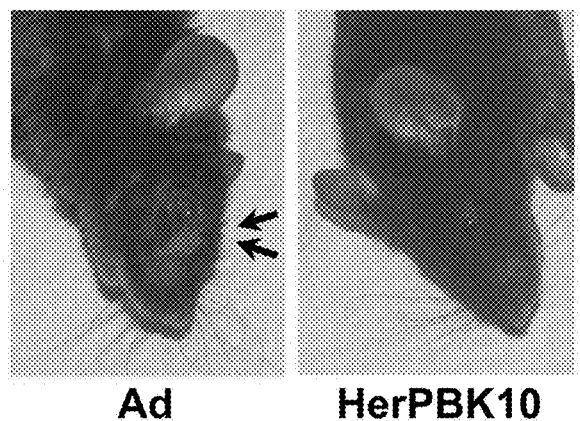
FIG. 18 depicts, in accordance with an embodiment herein, external lesions in Ad vs. HerPBK10 treated mice. C57BL/6 mice inoculated with Ad or HerPBK10 as described in FIG. 17, were observed for notable effects on eyes and periocular hair (arrows).
Figure 19:
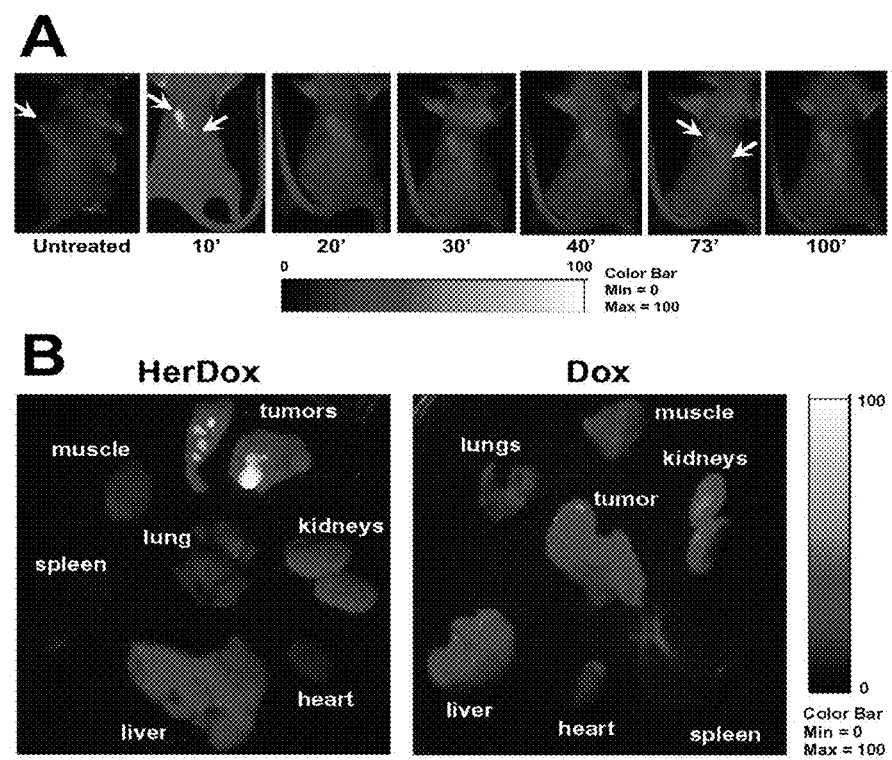
FIG. 19 depicts, in accordance with an embodiment herein, preferential targeting to HER2+ tumors. Tumor-bearing mice were injected with 0.02 mg/kg (final Dox dose) of HerDox or Dox via the tail vein and imaged with a custom small animal imager. A, Imaging of live mice after IV delivery of HerDox. Time points are shown as minutes after injection. Tumors are indicated by arrows. B, Imaging of tumors and tissues harvested at 3 h after injection of HerDox or Dox. Fluorescence signal from Dox is pseudo-colored according to the color bar, with a shift toward 100 indicating high fluorescence intensity.
Figure 20:
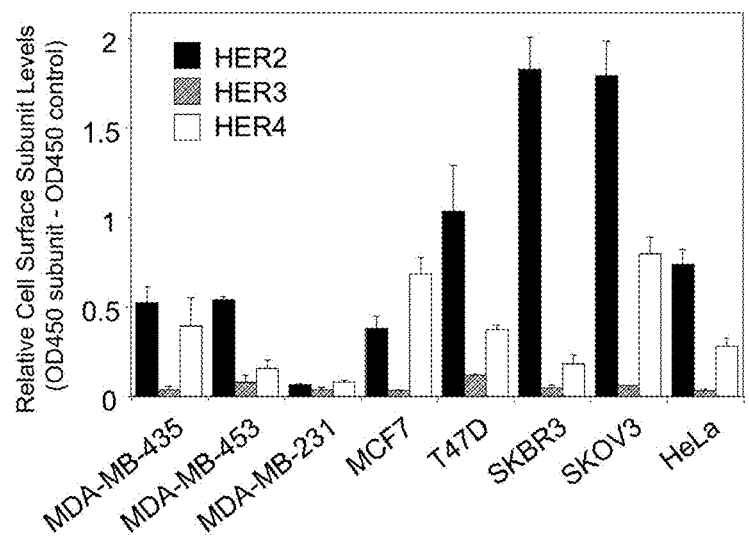
FIG. 20 depicts, in accordance with an embodiment herein, relative cell surface HER subunit levels as measured by ELISA. Cells were plated on a 96-well plate at $1\times10^4$ cells/well and grown two days before 15 min fixation at RT with 4% paraformaldehyde in PBS, followed by rinsing 3× in PBS, and blocking with 1% BSA/PBS solution for 1 h at RT. Fixed cells were incubated with anti-HER subunit antibodies (1 ug/mL anti-erbB-2/Her-2 rabbit polyclonal IgG and anti-erbB-3/Her-3 mouse monoclonal IgG from Upstate Biotechnology Inc., Lake Placid, N.Y., USA; and 3 ug/mL mouse monoclonal [HFR1] to Her4 from Abcam Inc., Cambridge, Mass., USA), followed by incubation with HRP-conjugated secondary antibodies and enzymatic assay using standard procedures (Agadjanian et al., 2009), with product formation quantified by absorbance at 450 nm. Relative cell numbers were quantified by crystal violet staining and absorbance at 590 nm. Relative subunit levels are reported as the ELISA signal of each cell population normalized by the relative cell number, or absorbance 450 nm/590 nm.
Figure 21:
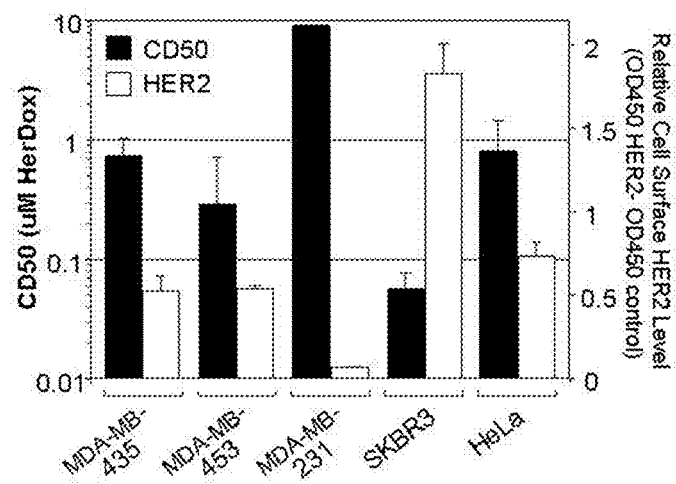
FIG. 21 depicts, in accordance with an embodiment herein, toxicity to cells displaying differential HER2. Cytotoxicities from a range of HerDox doses were assessed on each cell line by metabolic assay and confirmed by crystal violet stain. CD50 values (shown in log scale) were determined by non-linear regression analyses of HerDox dose curves using a scientific graphing program (GraphPad Prism) and confirmed with an on-line calculator (Chang bioscience). The relative HER2 level of each cell line is shown next to each CD50 value.
Figure 22:
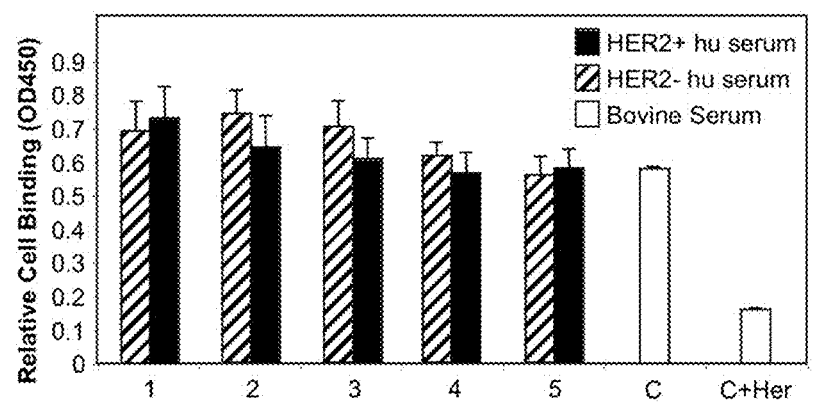
FIG. 22 depicts, in accordance with an embodiment herein, HerPBK10 binding to MDA-MB-435 cells in human serum from HER2+ or HER2− breast cancer patients. Cells were treated with HerPBK10 (1.2 ug/well) in wells containing human serum from each of 5 HER2+ breast cancer patients or age matched HER2− controls, both obtained pre-chemotherapy treatment. Cells were processed for ELISA using an antibody directed at HerPBK10. Control (C) wells receiving HerPBK10 in media containing 10% bovine serum without or with 100× molar excess ligand inhibitor (+ Her) are indicated by open bars. Patient sera were provided by the WCRI tissue bank at Cedars-Sinai Medical Center. N=3 wells per treatment.
Figure 23A:
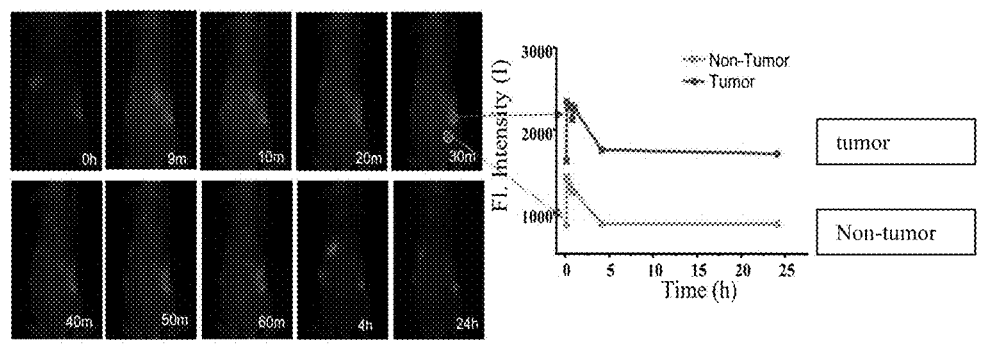
FIG. 23 depicts, in accordance with an embodiment herein, monitoring in vivo tumor targeting. The inventors assembled HerPBK10 with Cy5-labeled HER2 siRNA (siRNA labeling kit, Mirus) and filtered the complex through a 50K MWCO ultrafiltration column to remove free label. A single tail vein injection of either (A) free siRNA or (B) HerPBK10-siRNA, equating ~40 pmoles of Cy5 label, was each delivered into separate female nude mice bearing bilateral flank tumors of HER2+ (MDA-MB-435) cells. The mice were immediately monitored by in vivo fluorescence intensity imaging through our collaborators' imaging facility (Farkas lab, Cedars-Sinai Medical Center). C, Analysis of the fluorescence intensity contrast between tumor and non-tumor areas of A and B (graphs).
Figure 23B:
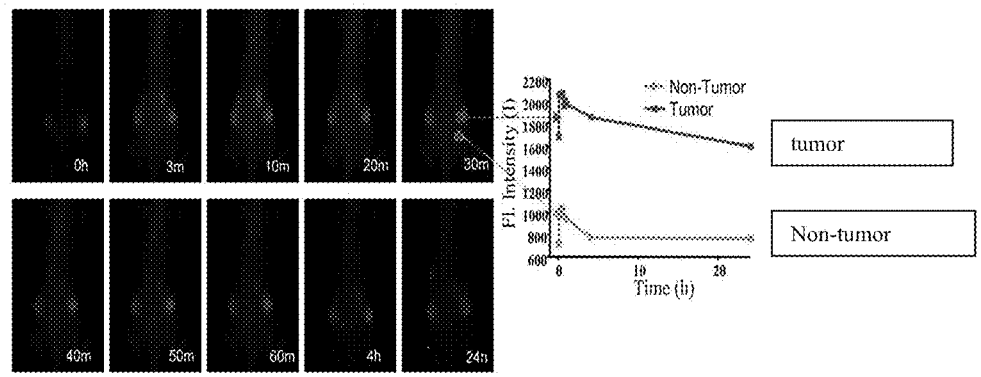
Figure 23C:
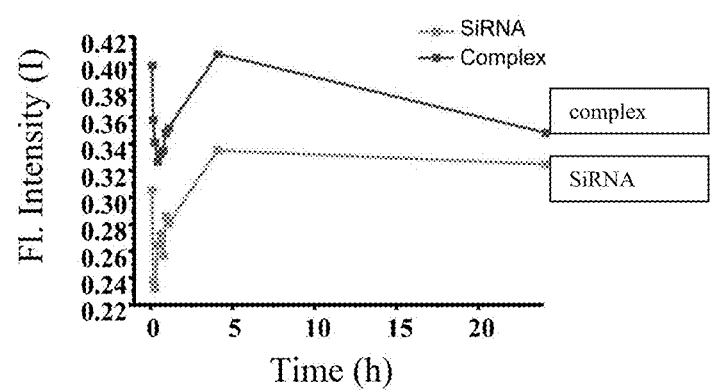
Figure 24:
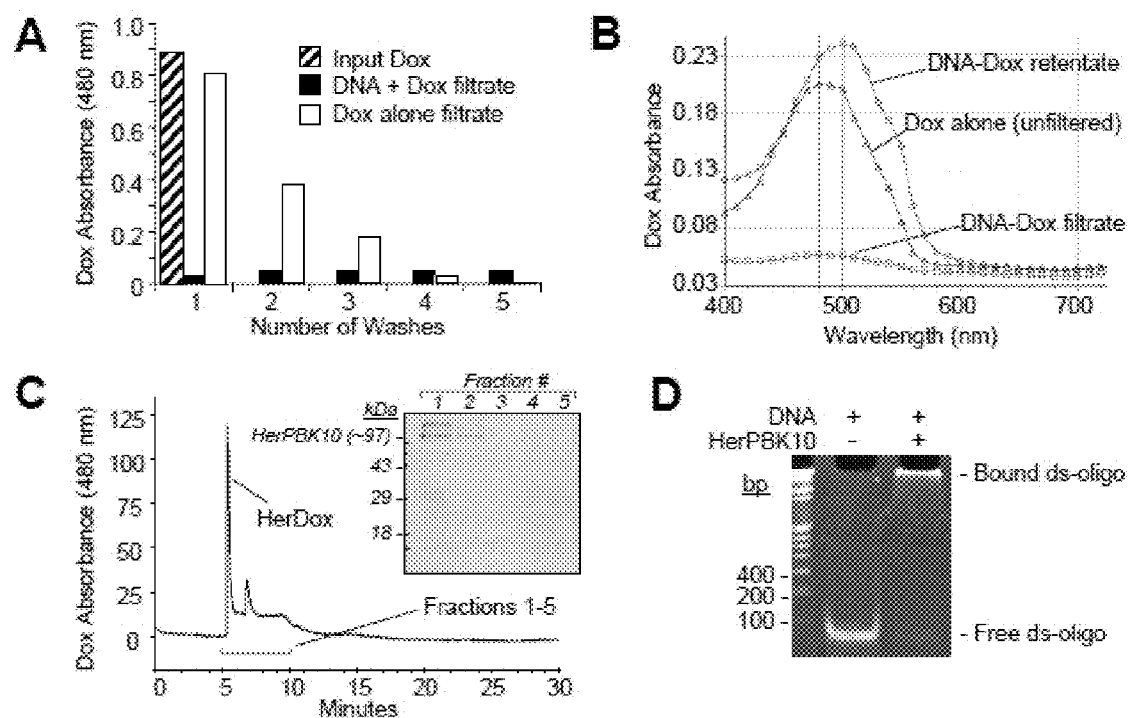
FIG. 24 depicts, in accordance with an embodiment herein, HerDox assembly. A, Assembly of DNA-Dox. Graph shows A480 (Dox absorbance maximum) of DNA-Dox and free Dox filtrates during assembly. Input Dox, A480 before filtration. B, Absorbance spectra of DNA-Dox retentate and filtrate after assembly. C, HerPBK10 binding to DNA-Dox. HPLC graph shows eluates (detected based on Dox absorbance) collected over time from a size exclusion column. Inset, SDSPAGE and immunoblotting of HPLC fractions collected at minutes 6-10 (fractions 1-5). Immunodetection of HerPBK10 was performed as described previously [10]. In subsequent experiments, HerDox was collected from the 6 min peak. D, Electrophoretic mobility shift assay showing HerPBK10 binding to ds-oligo. Duplex (150 ng) was incubated with HerPBK10 (4 ug) for 10 min at RT before 15% PAGE, followed by EtBr stain (30 min) before UV visualization.
Figure 25:
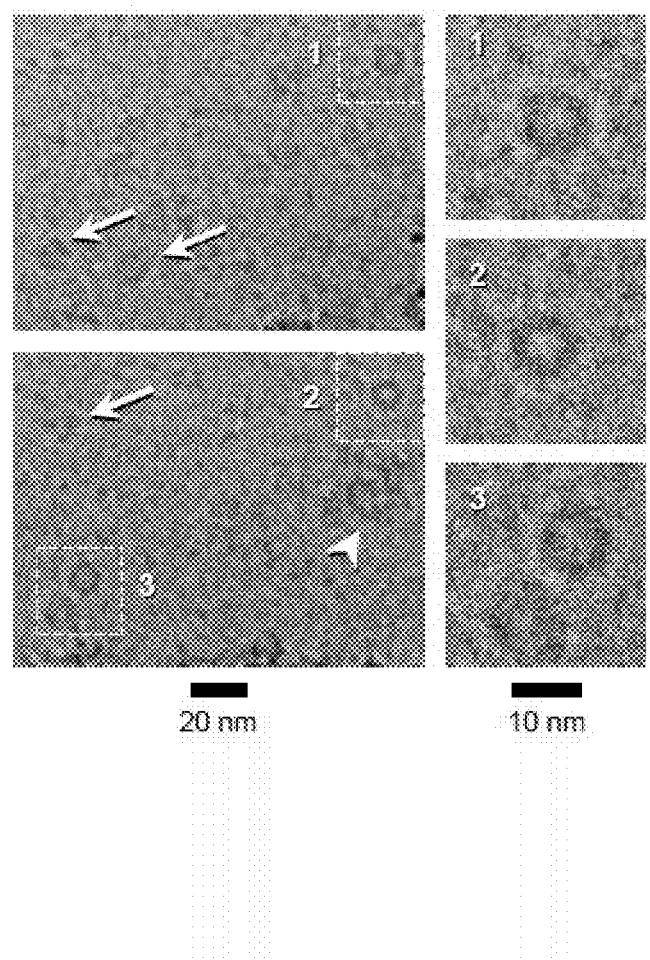
FIG. 25 depicts, in accordance with an embodiment herein, CryoEM of HerDox particles. Micrographs show the formation of small particles that are mostly round (delineated regions) or with less defined shape (arrows), as well as larger aggregates (arrowhead). Macro-aggregates up to 200 nm and larger were also evident. Numbered areas highlighting representative round particles are enlarged in right panels. Sample preparation and imaging was performed by NanoImaging Services, Inc., La Jolla, Calif., USA.
Figure 26:
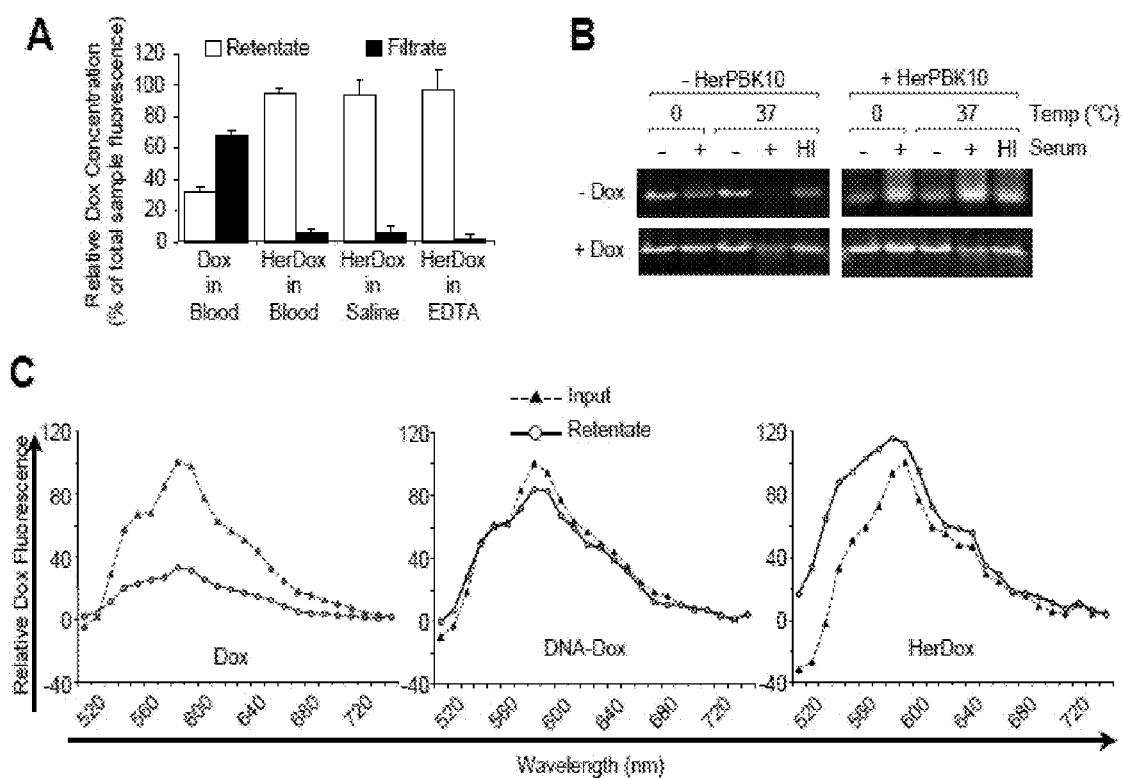
FIG. 26 depicts, in accordance with an embodiment herein, stability in serum. D, Stability in blood. Graph shows retentate and filtrate fluorescences of HerDox or Dox after 1 h incubation in mouse blood, saline, or 0.5 mM EDTA at 37° C., followed by ultrafiltration. N=3. E, Representative gels (N=4 per experiment) showing DNA protection in serum. The dsoligo pre-bound by Dox (+Dox), HerPBK10 (+ HerPBK10), or both was incubated for 20 min in 100% mouse serum (Abcam, Cambridge, Mass., USA) before PAGE and EtBr staining to visualize the DNA (Dox fluorescence was not visible on the gel at the concentrations used). Control conditions preventing digest include using heat-inactivated (HI) serum and 0° C. incubation. F, Assessing Dox retention in serum. Graphs show fluorescence spectra of Dox, DNA-Dox and HerDox before (input) and after incubation in 100% mouse serum followed by ultrafiltration and measurement of retentates.
Figure 27:
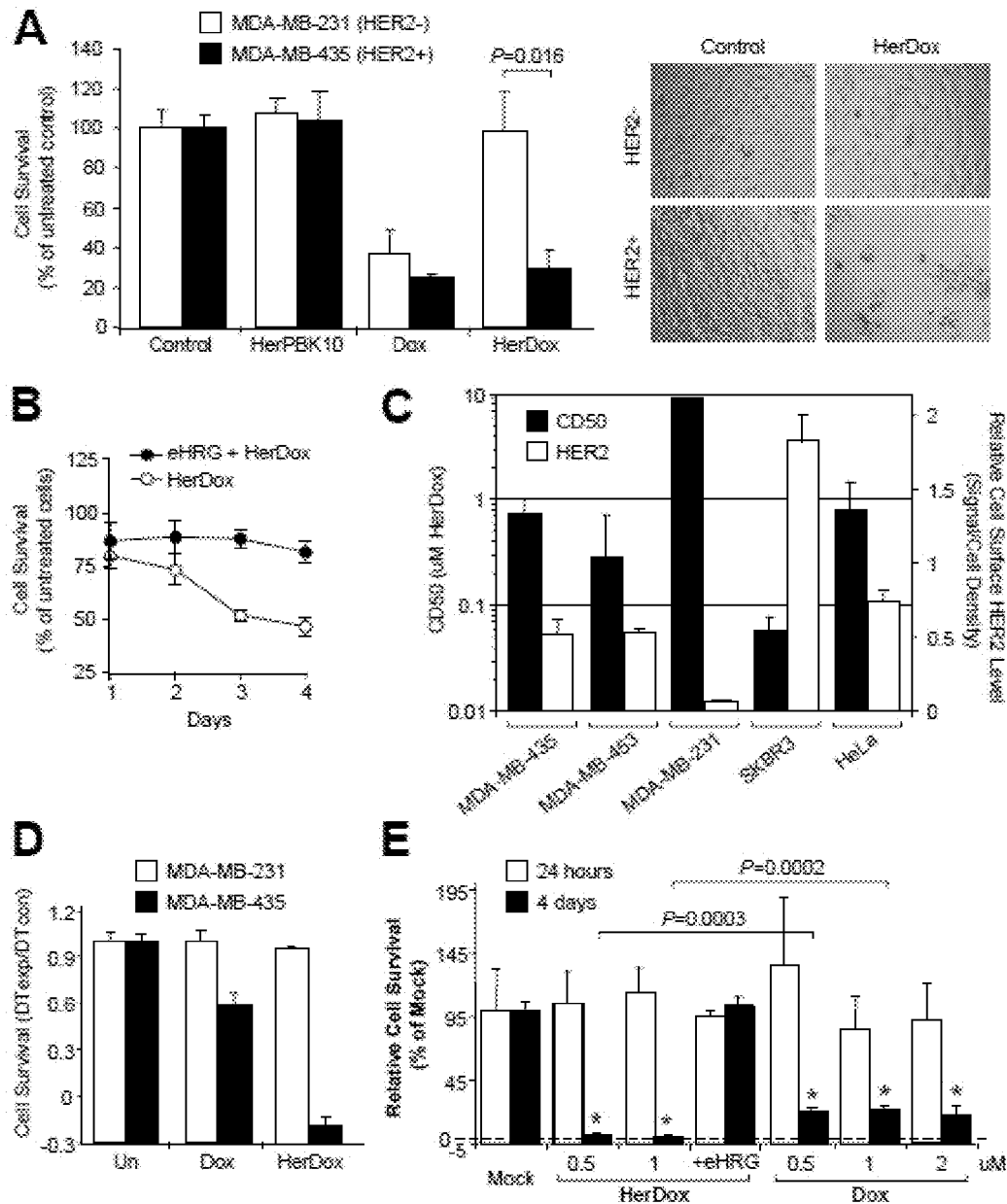
FIG. 27 depicts, in accordance with an embodiment herein, targeted toxicity in vitro. All treatments, N=3. A, Comparing cytotoxicity to HER2+ (MDAMB-435) and HER2− (MDA-MB-231) cells in separate cultures. Left, Relative survival (as % of untreated cells) on day 3 of treatment. Right, Micrograph of live cells after treatment. Control, mock (HBS) treatment. B, Receptor specificity of cytotoxicity. Graph shows relative survival of MDA-MB-435 cells receiving HerDox −/+ competing ligand (eHRG). C, Toxicity to cells displaying differential HER2. Cytotoxicities from HerDox titrations were assessed on each cell line by metabolic assay and confirmed by crystal violet stain on day 3 of treatment. CD50 values (shown in log scale) were determined by non-linear regression analyses of HerDox killing curves using GraphPad Prism. The relative HER2 level of each cell line is shown next to each CD50 value. D, Targeting in a mixed MDA-MB-435(HER2+, GFP−)/MDA-MB-231(HER2−,GFP+) cell culture. Survival was determined by calculating the relative doubling time (DT) of experimental (exp) cells normalized by mock-treated (con) cells based on crystal violet stains (total cells)

The Targeted siRNA Complex as Well as Carrier Protein Alone Induce Interferon (IFN)-Alpha Secretion from HER2+ but not HER2− Breast Cancer Cells The mechanism of T7-transcribed siRNA cytotoxicity is thought to be via the induced secretion of cytotoxic cytokines as a cellular response (Kim et al., 2004). To examine whether cytokines contribute to the targeted toxicity observed earlier, the media of HerPBK10-siRNA (T7-transcribed)-treated HER2+ MDA-MB-435 and HER2− MDA-MB-231 cells were collected and assayed by ELISA for interferons alpha and beta. Our findings show that IFN-alpha secretion from MDA-MB-435 cells is substantially elevated after treatment with HerPBK10-siRNA complex (at 10 and 50 nM siRNA dose) as well as HerPBK10 alone (at equivalent concentration to the 50 nM dose) (FIG. 13A). Whether the effect produced by the protein is elicited by receptor signaling remains to be seen, though it is interesting that despite the high IFN-alpha secretion in response to Her-PBK10, the protein alone does not induce substantial cell death (FIG. 13B). MDA-MB-231 cells are little affected by either HerPBK10 or the complex (FIG. 13A). Both cell lines showed little to no sign of IFN-beta secretion regardless of treatment, though significant differences between HER2+ and HER2− cells were observed, especially after 10 nM HerPBK10-siRNA treatment (FIG. 13B). Given the overall low level of cytokine detected in the medium by all treatments, these differences are likely to have little relevance.

Example 14

Advantages

This invention enables direct RNA interference (RNAi) to target cells.

Targeting and Penetration: Most current therapeutics affect the body globally because they are not targeted to the specific tissue or cell that is meant to be treated. Moreover, if such therapeutics can be targeted to the desired tissue or cell type, delivery does not necessarily entail efficient penetration of the therapeutic into the desired tissue or cell type. Thus, the two main problems of therapeutic delivery addressed here are: 1. targeting, and 2. penetration.

Overcoming complicated formulations and high cost of production: Another general problem of therapeutic development is complexity and cost of production when the therapeutic is a synthetic molecule or combination of covalently bonded molecules. Production of the delivery agent as a recombinant fusion protein as described here enables pharmaceutical quantities to be generated by large-scale fermentation with facile quality control. Noncovalent assembly of the targeted missile avoids the need for complex chemical bonding reactions and additional processing steps to check the purity and integrity of the final product. Altogether, these practical features entail a lower cost of production compared to completely synthetic reagents.

Non-specific cytotoxicity of siRNA: With respect to the delivery of siRNA and similar nucleic acids encoding RNAi, cell specific targeting is necessary to ensure that the RNAi effect is imparted at the desired cell type, as some siRNA molecules can have a generalized cytotoxicity due to the cytokine-inducing effect of the molecule itself, irrespective of the sequence being delivered. The general scientific community has seen this as a pitfall of RNAi, given that the RNAi technology was originally intended to silence specific genes at which the RNAi sequence is targeted. The inventors have exploited this feature by combining it with cell-targeted proteins to target this cytotoxic effect to cancer cells, as an improved means of tumor toxicity. In the practical examples provided herein, the inventors delivered siRNA carrying sequences known elsewhere to induce cell death after gene silencing, thus the combination of both gene-specific silencing and molecule-induced toxicity should entail high potency, especially when combined with the targeting and efficient penetration imparted by the recombinant carrier protein.

Example 15

Flawed Alternatives

HER2+ breast tumors, which over-express subunit 2 of the human epidermal growth factor receptor (HER), comprise a significant subset of breast cancers that are recalcitrant to standard methods of treatment, and predict a high mortality. The abnormally high level of HER on the surface of these tumor cells may enable targeted therapeutics to home in on these cells, thus making HER2+ tumors ideal candidates for targeted therapy. The current strategies for targeting therapy to these tumors include antibody-targeted chemotherapy agents (immunoconjugates), targeted toxins, signal-blocking antibodies, and antibody-targeted liposomes (immunoliposomes).

Immunoconjugates:

Immunoconjugate therapies rely on the chemical coupling of single-chain antibodies to drugs, whereby the antibody directs the drug to specific cells by recognizing certain cell surface proteins or receptors (Chester et al., 2000; Frankel et al., 2000). Studies have shown, however, that such antibodies can unfold and aggregate at physiological temperature, which would impede binding to target cells, and result in low therapeutic efficacy (Glockshuber et al., 1990; Schmidt et al., 1999). Moreover, covalent linkage of drug to carrier can impair the activity of both molecules, as well as entail high production cost.

Targeted Toxin:

An alternative approach to tumor targeting has been the development of toxic proteins, such as plant or bacterial toxins, that are modified by appendage to a targeting peptide (or ligand) (Frankel et al., 2000). Such proteins are produced by recombinant methods (i.e. genes are engineered to produce the proteins in a cell system, from which the proteins can then be isolated), and the resulting protein is a fusion of the toxin to the ligand. While fusion toxin proteins can be produced by large scale fermentation as a more efficient and lower cost alternative to antibody generation, the toxin requires special processing to be active, thus limiting potency (Jeschke et al., 1995; Schmidt et al., 1999). For example, the activity of recombinant diptheria toxin transmembrane domain, used to enhance non-viral gene transfer, is reduced by as much as 75% when fused to a foreign peptide, indicating that appending a peptide to a toxin disables toxin activity (Fisher and Wilson, 1997).

Signal Blocking Antibodies:

Antibodies directed at the extracellular domain of HER2 have been used to target drug complexes to the HER2 subunit, but have not necessarily induced internalization of the drug complex, thus limiting potency (Goren et al., 1996). Such findings illustrate that targeting is not enough, as a lack of targeted uptake can limit efficacy. Alternatively, signal blocking antibodies have been developed to inhibit the proliferative signal transduced through overexpression and high cell surface display of HER2 (Baselga et al., 1996; Cobleigh et al., 1998). The currently used targeted therapy, trastuzumab (Herceptin), an antibody directed against the HER2 subunit, blocks normal signaling but has been ineffective in about 70% of treated patients, possibly due to aberrant intracellular pathways in tumor cells that may not respond to signal inhibition (Vogel et al., 2002) (Kute et al., 2004). More importantly, an ongoing concern with trastuzumab is the exquisite sensitivity of heart tissue to HER2 signal inhibition, which is further exacerbated by anthracycline chemotherapy agents (Slamon et al., 2001).

While targeted uptake facilitates drug entry into target cells, the intracellular disposition of the drug can still affect potency. Targeting antibodies delivering covalently linked drugs can be trafficked to lysosomes, thus sequestering the drug from subcellular targets and limiting potency. Approaches to circumventing this include linking the drug to a targeting antibody via an acid labile bond to facilitate release into the endocytic compartment (Braslawsky et al., 1990; Trail et al., 2003; Trail et al., 1992; Trail et al., 1993). However, bond instability can reduce in vivo potency, likely by causing premature drug release and thus delivery to non-target tissue.

Immunoliposomes

Immunoliposomes, carrying doxorubicin (Dox) and targeted to HER2, have been developed and can accumulate in tumor tissue in animal models (Park et al., 2002), likely due to the leaky tumor vasculature (Drummond et al., 1999). Release of Dox from these liposomes is thought to occur via the acidic tumor environment, lipase release from dying cells, and enzyme and oxidizing agent release from infiltrating inflammatory cells (Minotti et al., 2004). These conditions may induce premature drug release and nonspecific delivery, though the accumulation of immunoliposomes at tumor sites may tend to favor drug uptake at the tumor. Studies using the trastuzumab Fab fragment for liposome targeting of Dox have demonstrated antitumor efficacy (Park et al., 2002), though the effect on cardiac tissue was not reported in that study.

In General:

Problems with the current tumor targeting strategies include: requirement for chemical modification, which can be costly and impair activity of drug and/or carrier; use of recombinant antibodies that can lose structure in physiological conditions and thus result in impaired targeting activity; inability to penetrate into the cell; need to modulate receptor signaling, which can be impaired in tumor cells and thus ineffective; and, importantly, off-target effects, including toxicity to the heart.

Example 16

Advantages Over Flawed Alternatives

Advantage Over Immunoconjugates:

Whereas covalent linkage of drug to carrier can impair the activity of both molecules, as well as entail high production cost, our studies show that our targeted carrier protein, HerPBK10, retains receptor targeting under physiological conditions in the presence of serum, indicating that our targeted carrier does not unfold or lose receptor binding. Furthermore, embodiments of the invention is engineered so that the drug self-assembles with the carrier molecule and thus does not require chemical modifications to covalently link the molecules together. This noncovalent assembly would thus allow both the targeted carrier and drug to remain unmodified and thus preserve structure and activity. Finally, recombinant proteins such as HerPBK10 can be produced in bulk quantities by large-scale fermentation for a lower cost compared to monoclonal antibody generation and production.

Advantage Over Targeted Toxins:

As most toxins require special processing to be active, producing these as fusions can limit potency. Thus, delivery by noncovalent means (i.e. self-assembly) as proposed herein is likely to be advantageous in terms of retaining drug potency.

Advantage Over Signal Blocking Antibodies:

Antibodies generated to recognize a specific epitope have the potential to direct therapies to normal cells presenting normal levels of the epitope being targeted. In conjunction with various embodiments described herein, the inventors take advantage of the binding interaction of the natural ligand for HER, which have a greatly increased ligand affinity when HER2 is overexpressed. This is likely to translate to lower, and thus safer, doses of drug when targeted, thus avoiding the likelihood of cardiac damage. Accordingly, the targeting approach should avoid binding to tissues displaying low to normal receptor subunit levels but exhibit preferential binding to HER2+ tumor cells. Moreover, the inventors have shown that the receptor binding domain of heregulin that is incorporated into HerPBK10 induces rapid internalization after binding to the heregulin receptor (Medina-Kauwe and Chen, 2002; Medina-Kauwe et al., 2000), enabling uptake of DNA (Medina-Kauwe et al., 2001b) and fluorescent compounds (Agadjanian et al., 2006). Antibodies generally do not induce receptor-mediated uptake. Our approach, therefore, circumvents the need to modulate receptor signaling, by exploiting the rapid receptor endocytosis induced by ligand binding and the cytosolic penetration features of viral capsid protein to directly transport drugs into the cell and induce cytotoxicity from within. Additionally, the endosomal disruption feature of various embodiments described herein has the advantage of endosomal escape, thus facilitating release of the therapeutic into the cell cytoplasm and access to intracellular targets, including gene transcripts.

Advantage Over Immunoliposomes:

The inventors believe that the system will yield effective targeted drug delivery due to high affinity receptor-ligand binding and rapid endocytosis coupled with the membrane-penetrating activity of the viral penton base protein to ensure efficient delivery into target cells.

Advantage Over Gene Therapy:

While gene therapy approaches are a possibility, the inventors have found that the large size of a DNA plasmid complicates vector assembly by requiring that additional DNA condensing molecules be incorporated into the vector to reduce the size of the plasmid. Such agents not only add to the complexity of the overall vector system but can also hamper targeting and gene expression by binding DNA well (Medina-Kauwe et al., 2001a; Medina-Kauwe et al., 2001b) but releasing DNA poorly (Zabner et al., 1995). Because siRNA molecules are 200-300 times smaller than the average DNA vehicle for gene therapy, development of siRNA missiles involves much simpler and more streamlined procedures compared to non-viral gene therapy vector development. Adding to the benefits of this system is that fewer barriers would need to be overcome compared to gene therapy systems: the siRNA molecule need only be delivered to the cytoplasm as opposed to translocating through the cytosol and being transported into the nucleus.

Toxicity Advantage:

Cell death can be induced by certain modifications carried by siRNA molecules Kim et al (2004) reported that siRNA molecules carrying a 5' triphosphate stimulate interferon alpha and beta (IFNalpha and IFNgamma) secretion from siRNA-transfected cells, inducing cell death in culture (Kim et al., 2004). Such modifications are introduced into siRNA produced from bacteriophage T7 RNA polymerase, but siRNA produced synthetically do not carry such modifications, and likewise do not induce cytokine secretion. Removal of the 5' triphosphate completely eliminated IFN induction. The induction of IFN correlated with cell death by 5 days after siRNA transfection, and the effect could be transferred with the medium from transfected cells.

Example 17

Comparing Various RNAi Species

The inventors wanted to determine what type of RNAi species delivered the most potent cytotoxicity in order to incorporate it into the targeted complex and test it in vivo. They compared HER2-silencing siRNA produced either synthetically by a commercial vendor (Dharmacon), or from a T7 transcription kit (Ambion), and shRNA, which is reportedly a more effective substrate for the dicer mechanism in RNAi. Targeted complexes or the equivalent concentration of HerPBK10 alone were added to separate sets of triplicate wells containing GFP-tagged MDA-MB-435 (HER2+) or MDA-MB-231 (HER2−) human cancer cells. At 96 hours after treatment, cell survival was assessed by convalidating assays: GFP fluorescence and metabolic activity (MTT). Both assays confirmed that the T7 transcribed siRNA is the most potent cytotoxic species. Moreover, the HER2+ cells exhibit substantially greater sensitivity to the targeted complexes compared to the HER2− cells, providing further evidence that the complex is targeted to HER2+ cells.

Example 18

Reduction in Tumor Growth from Intratumoral Injection

Before testing for targeted toxicity of HerPBK10-siRNA, the inventors assessed cytotoxic potential in vivo after intratumoral (IT) injection of complexes in tumor-bearing mice. Tumor bearing nude mice received two IT injections, each a week apart from one another, of either T7 transcribed siRNA alone or HerPBK10-siRNA, and tumor volumes were measured weekly before, during, and after injections. Blood was also collected after each injection to assess cytokine levels. Mice receiving HerPBK10-siRNA exhibited an average reduction in tumor growth whereas tumor growth in mice receiving siRNA alone was unaffected. Even though the complex was not delivered intravenously but rather by IT injection, there still appears to be an advantage to the targeted complex with regard to tumor toxicity.

Example 19

Destruction of Tumor Cells Via Cytokine-Mediated Cytotoxicity

The mechanism of non-specific T7-transcribed siRNA cytotoxicity is thought to be via the induced secretion of cytotoxic cytokines as a cellular response to secondary modifications introduced onto the siRNA as a side-product of the T7 transcription. To examine whether cytokines contribute to the tumor reduction observed and described herein, blood was collected from the same mice at 24 h after each IT injection and assayed for interferon (IFN)-alpha. While overall cytokine levels remained low, HerPBK10-siRNA injection yielded elevated circulating IFN-alpha compared to IT saline injections (control). The trend from the first set of IT injections indicates that siRNA alone tends to elevate circulating IFN-alpha over the controls, though not to statistically significant levels. While previous studies show that HerPBK10 alone has no effect on HER2+ tumor cell growth, the inventors have yet to determine whether the carrier protein contributes directly to cytokine elevation. It is possible that its indirect contribution results from enhanced tumor delivery, penetration, retention. Together with the tumor-shrinkage observed from these injections, these findings provide additional evidence that the targeted carrier, HerPBK10, can deliver both siRNA-mediated silencing and cytokine-mediated cytotoxicity to induce two-pronged targeted destruction to tumor cells.

Example 20

Evidence Targeted Carrier HerPBK10 does not Induce Neutralizing Antibodies

To address concerns regarding the use of an Ad capsid protein-derived carrier for siRNA, the inventors examined whether HerPBK10 induced neutralizing antibody formation. A single inoculation of Ad can produce a long-lasting humoral response in patients and animals, and prevent subsequent administration, thus reducing overall therapeutic efficacy of Ad-mediated therapies. Here the inventors tested the antibody formation potential of HerPBK10 under the same conditions that produce an Ad capsid-elicited immune response.

Immunocompetent (C57BL/6) mice were inoculated with HerPBK10 at 0.05 mg/kg (with regard to protein dose) as well as a 10-fold higher dose (0.5 mg/kg). As a comparison, mice were also inoculated with Ad5 at a dose established elsewhere to induce neutralizing antibodies ($1.2 \times 10^9$ pfu/mouse). Blood was collected from mice before initial antigen injection, followed by blood collections every 7 days up to 35 days post-initial inoculation, while mice received a second inoculation of the same antigens on day 21 to boost any existing immunity.

ELISA of blood serum from treated mice showed that both doses of HerPBK10 produced no significant induction of anti-HerPBK10 antibodies in comparison to untreated mice, whereas the dose of Ad5 used here triggered secretion of antibodies that recognize HerPBK10. As the latter result may simulate the presence of pre-existing antibodies from a previous Ad infection or exposure, it would be critical to determine whether such antibodies could prevent the binding of HerPBK10 to target cells. To test this, the inventors assessed ligand-receptor binding by measuring the attachment capacity of MDA-MB-435 cells to HerPBK10-coated plates in immune serum. In the absence of serum, the cells readily attach to HerPBK10-coated wells, while the heregulin receptor-blocking ligand, Her, significantly reduces this binding, thus confirming that the cells undergo heregulin receptor-specific attachment (P<0.05 compared to binding without serum or competitive inhibitor, as determined by 2-tailed unpaired t test). The level of cell attachment in sera from Ad5-treated mice was comparable to that in the absence of serum and in pre-immune serum. Likewise, sera from mice treated with 0.05 and 2.5 mg/kg HerPBK10 did not reduce attachment, and while 0.5 mg/kg HerPBK10 appeared to slightly reduce attachment, this was not significant (P<0.05 compared to binding without serum or competitive inhibitor, as determined by 2-tailed unpaired t test) (FIG. 4B). Altogether, these findings indicate that the targeted carrier, HerPBK10, does not induce neutralizing antibodies, which would otherwise be inhibitory to therapeutic efficacy.

Additionally, Ad-treated mice showed signs of inflammation and fur loss around the eye area, whereas HerPBK10-treated mice showed no such damage, and appeared similar to mock-treated mice. Whereas such hair loss can be attributed to dominant mouse barbering or cage lesions, all Ad treated mice showed this phenotype and were continuously kept separately from other mice, whereas none of the other mice showed any such phenotype. Acute periocular hair loss and corneal damage can result from herpes simplex virus infection in mice and may involve viral-induced autoimmunity. It is worth noting the correlation between Ad infection, which can induce T-cell immunity and inflammation, and the phenotype observed here.

Example 21

Additional Evidence of HerPBK10 Directed Systemic Targeting of Small Nucleic Acids Such as siRNA The inventors used the fluorescent DNA intercalator, doxorubicin (Dox), to tag a double-stranded oligonucleotide mimicking an siRNA molecule to track its biodistribution after systemic delivery in mice bearing 4-week old tumors (~700-800 $mm^3$) The Dox-intercalated nucleic acid was complexed with HerPBK10 using equivalent conditions for HerPBK10-siRNA assembly. Mice received a single tail vein injection of Dox alone or the complex (HerDox) (0.02 mg/kg with respect to Dox conc) and were imaged live using a customized macro-illumination and detection system. Fluorescence was evident throughout the body at 10 min after HerDox injection, then quickly accumulated at the tumors by 20 min and remained detectable in the tumors up to 100 min after injection. Tissues and tumors harvested at ~3h after HerDox injection showed intense fluorescence in the tumors while substantially lower levels of fluorescence were detectable in the liver. Some fluorescence was barely detectable in the kidneys while other tissues, including the heart, spleen, lungs, and skeletal muscle, did not exhibit any fluorescence. In contrast, tissues harvested from mice injected with the equivalent dose of Dox exhibited detectable fluorescence in the liver, tumor, and kidneys. Lower levels of fluorescence were also detectable in the lungs and skeletal muscle. Overall, these findings indicate that HerPBK10 directs systemic targeting of small nucleic acids (similar to siRNA) to HER2+ tumors in vivo.

Example 22

Additional Evidence of Targeting Efficacy

To assess whether targeting and potency corresponds to HER2 levels, the inventors selected lines displaying HER2 at relatively high (SKBR3), moderate (MDA-MB-435, MDA-MB-453, HeLa), and low to undetectable (MDA-MB-231) levels, according to receptor subunit profiling of a panel of cell lines disclosed herein, and performed cytotoxicity dose curves using the HerDox complex previously used. The inventors observed that HerDox CD50 inversely correlates with cell surface HER2 level on these selected lines: the cell line displaying relatively high HER2 shows a relatively higher sensitivity to HerDox whereas the cell line displaying low HER2 exhibits low sensitivity, and the lines displaying intermediate HER2 levels likewise exhibit intermediate sensitivities. Altogether, these findings indicate that tumor-targeting correlates with HER2 cell surface display levels, supporting the targeting efficacy of the complex.

Example 23

Evidence Human Sera does not Interfere with Targeted Binding

To determine whether HerPBK10 can compete with circulating ligand that may be present in serum, the inventors tested HerPBK10 binding to HER2+ breast cancer cells in human serum obtained from HER2+ patients. The Women's Cancer Research Institute at Cedars-Sinai occasionally acquires limited quantities of patient serum, of which sera from HER2+ patients comprises an even smaller minority. Notably, the human serum used here is from collected whole blood of HER2+ and age-matched HER2− patients. The inventors ensured that cells received considerable exposure to the human sera (2 hours, which provides ample time for receptor binding of any circulating ligand) prior to treatment. Head-to-head comparisons of cell binding in serum from either HER2+ patients, HER2-patients, or bovine serum show no significant differences, indicating that the human sera tested here did not interfere with HerPBK10 binding to target cells. Pre-blocking receptors with 100× competitive ligand (+ Her) confirms that binding is specific to heregulin receptors.

Example 24

Tumor Targeting of siRNA In Vivo

To assess in vivo tumor-targeting ability for the delivery of siRNA, the inventors imaged HER2+ tumor-bearing mice after tail vein injection of fluorescently-labeled siRNA or HerPBK10-siRNA complex. Based on analysis of the fluorescence intensity contrast between tumors and non-tumor areas, HerPBK10-siRNA exhibits preferential tumor accumulation compared to the free siRNA at all time points monitored. Moreover, HerPBK10-siRNA displays tumor retention whereas the free siRNA clears from the tumors by 24 h after tail vein injection. Altogether, these results suggest that HerPBK10 facilitates tumor targeting and tumor retention of siRNA, likely due to the cell binding and penetration capacity of the HerPBK10 protein.

Example 25

Chemotherapy Targeting by DNA Capture in Viral Protein Particles—HerDox

The inventors tested whether DNA intercalation and electrophilic interactions can be exploited to non-covalently assemble doxorubicin in a viral protein nanoparticle designed to target and penetrate tumor cells through ligand-directed delivery. They further tested whether this new paradigm of doxorubicin targeting shows therapeutic efficacy and safety in vitro and in vivo. Serum-stability, tumor-targeting, and therapeutic efficacy in vitro and in vivo using biochemical, microscopy and cytotoxicity assays were tested.

As disclosed herein, the inventors found self-assembly formed serum-stable ~10 nm diameter nanoparticles that can target and ablate HER2+ tumors at >10× lower dose compared to untargeted doxorubicin while sparing the heart after intravenous delivery. The targeted nanoparticle tested allows doxorubicin potency to remain unaltered during assembly, transport, and release into target cells while avoiding peripheral tissue damage and enabling lower, and thus safer, drug dose for tumor killing. This nanoparticle can be an improved alternative to chemical conjugates and signal-blocking antibodies for tumor-targeted treatment.

Example 26

HerDox—Materials

Polyhistidine-tagged recombinant protein production and affinity chromatography purification is previously described. The following respective 48 and 30 base oligonucleotide sequences, SEQ ID NO: 8 BglIIHis-5 (5' ACTACAGATCT-CATCATCATCATCATCATGAGCTCAAGCAGGAATTC-3') and SEQ ID NO: 9 LLAA-5 (5'-CGCCTGAG-CAACGCGGCGGGCATCCGCAAG-3'), and corresponding reverse complements (BglIIHis-3 and LLAA-3) were custom-synthesized by commercial sources. HBS, HEPES-buffered saline (20 mM HEPES, pH 7.5; 150 mM NaCl). PBS, phosphate-buffered saline. Doxorubicin-HCl was obtained from Sigma-Aldrich (St. Louis, Mo., USA). AlexaFluor 680-labeling of PB was performed following manufacturer's procedures (Invitrogen, Carlsbad, Calif., USA). Ad5 polyclonal antibody (recognizing the PB domain of HerPBK10) was obtained from Access Biomedical, San Diego, Calif., USA. Anti-human αvδ3 and αvδ5 antibodies (used at 1:1,000 and 1:500, respectively, for immunofluorescence) were obtained from Chemicon/Millipore, Billerica, Mass., USA.

Example 27

HerDox—Cells

Human tumor cell lines of breast cancer (MDA-MB-435, MDA-MB-453, MDA-MB-231, MCF7, T47D, SKBR3), ovarian cancer (SKOV3), cervical carcinoma (HeLa), and glioma (U251, U87) origin were obtained directly from the National Cancer Institute repository and ATCC, maintained in DMEM, 10% fetal bovine serum under 5% C02, and immediately profiled for relative cell surface receptor subunit levels.

Example 28

HerDox—Particle Assembly

Annealed complementary oligonucleotides (ds-oligo), BglIIHis or LLAA duplexes, were incubated with Dox at 1:16 or 1:10 molar ratio of DNA:Dox, respectively, at room temperature (RT) for 30 min. Ratios were chosen based on the theoretical number of Dox molecules bound at saturation. Unincorporated Dox was removed by centrifugation through 10K MW cutoff (mwco) filter membranes. DNA-Dox was then incubated with HerPBK10 (2 h on ice) at 9:1 or 6:1 molar ratio (BglIIHis or LLAA duplexes, respectively) of HerPBK10:DNA-Dox in HBS, followed by either (where indicated): size-exclusion HPLC (TSKgel G3000SWXL 7.8 mm ID×30 cm; TOSOH Bioscience, LLC) equilibrated with HBS (1 mL/min flow rate) to isolate HerDox from incompletely assembled components; or ultrafiltration as described earlier. Treatment doses reflect the Dox concentration in HerDox, which was assessed by extrapolating the measured absorbance (A480) or fluorescence (Ex480/Em590) against a Dox absorbance or fluorescence calibration curve (SpectraMax M2; Molecular Devices, Sunnyvale, Calif., USA). Note: HerDox comprising BglIIHis duplex was initially used in pilot and in vitro experiments. As we observed no detectable differences in Dox retention by BglIIHis and LLAA oligoduplexes, the subsequent in vivo experiments were performed using HerDox comprising LLAA duplexes.

Example 29

HerDox—Cryo Electron Microscopy

CryoEM was performed by NanoImaging Services, Inc. (La Jolla, Calif., USA) implementing the following procedures (provided by NanoImaging Services, Inc.): Samples were preserved in vitrified ice supported by carbon coated holey carbon films on 400 mesh copper grids. All samples were prepared by applying a 3 µL drop of undiluted sample suspension to a cleaned grid, blotting away with filter paper and immediately proceeding with vitrification in liquid ethane. Grids were stored under liquid Nitrogen until transferred to the electron microscope for imaging. All grids were prepared the day the sample was delivered (complexes were assembled immediately before delivery). Electron microscopy was performed using an FEI Tecnai T12 electron microscope, operating at 120 KeV equipped with an FEI Eagle 4K×4K CCD camera. Vitreous ice grids were transferred into the electron microscope using a stage that maintains the grids at below −170 C. Images of the grid were acquired at multiple scales to assess the overall distribution of the specimen. After identifying potentially suitable target areas for imaging at lower magnifications, higher magnification images were acquired at nominal magnifications of 52,000× (0.21 nm/pixel) and 21,000× (0.50 nm/pixel). The images were acquired at a nominal underfocus of −4 µm (52,000×) and −5 µm (21,000×) at electron doses of ~10-15 e/Å2.

Example 30

HerDox—Stability in Blood/Serum

To study stability in blood, HerDox or Dox (60 uM each) were incubated in equivalent volumes of whole blood (containing 0.5 mM EDTA to prevent coagulation and freshly collected from the aorta of an anesthetized mouse following IACUC-approved procedures) for up to 60 min at 37° C., followed by centrifugation through 10K mwco filters. Retentate and filtrate fluorescences were extrapolated against a Dox calibration curve performed in blood plasma to correct for plasma-induced fluorescence shift. Blood alone showed negligible fluorescence. To assess protection from serum nucleases, the ds-oligo pre-bound by Dox, HerPBK10, or both was incubated for 20 min at 37° C. in 100% mouse serum (Abcam, Cambridge, Mass., USA) before polyacrylamide gel electrophoresis (PAGE) and ethidium bromide (EtBr) staining to visualize the DNA (Dox fluorescence was not visible on the gel at the concentrations used). Control conditions preventing digest include using heat-inactivated serum and 0° C. incubation. To confirm particle retention of Dox in serum, Dox, DNA-Dox and HerDox were suspended in 100% mouse serum and fluorescence spectra measured before a 30 min incubation at 37° C., followed by ultrafiltration (10K mwco). Filtrates were collected and membranes washed 3× with HBS before collection and fluorescence measurement of retentates. All fluorescence spectra were obtained using a 515 nm cutoff filter.

Example 31

HerDox—In Vitro Targeting

For all in vitro treatments, cell lines were grown for ~36 h after plating (104/well in 96-well dishes) to allow receptor re-expression, followed by media replacement with new media containing indicated constructs in reduced volume at the indicated final molarities for 4 h with rocking, followed by supplementation with additional media and continued growth for the indicated time periods. Except for the experiments performed on the U251 glioma cells (which received a one-time treatment), cells received these treatments daily while separate sets of wells were assessed for cell death by either metabolic assay (CellTiter Promega Corporation, Madison, Wis., USA) or crystal violet stain each day. Where indicated, cells received competitive inhibitor (eHRG) [26] at 10× molar excess for 30 min-1 h at 4° C. before treatment. Treatment of mixed (HER2+/HER2−) cell cultures with HerDox or Dox (0.5 uM), and cell surface receptor subunit level determination were performed as previously described.

Example 32

HerDox—In Vitro Imaging

General procedures: MDA-MB-435 cells were plated ~36 h before receiving HerDox or Dox (0.5 uM final Dox concentration) in fresh media containing the indicated constructs. For live cell assays, the cells (plated in chambers) were imaged at the indicated time points after treatment, under brightfield or DIC (where indicated) and fluorescence modes to identify the cell structure and Dox fluorescence, respectively. For fixed cell assays, the cells were plated on cover slips in 24-well plates (1×105 cells/well) ~36 h before receiving HerDox or Dox in fresh complete media at 37° C., and separate samples fixed and processed for immunofluorescence against HerPBK10 following established procedures [30]. A Leica SP2 laser-scanning confocal fluorescence microscope was used for fixed and live cell imaging.

Example 33

HerDox—Cytosolic Nuclease Digest Assay

MDA-MB-435 cell lysates were prepared by washing detached cells twice with PBS followed by suspension in 0.1 mL lysis buffer (320 mM sucrose, 20 mM HEPES, 3 mM MgCl2, 1 mM DTT and 1 mM PSMF)/3×106 cells, shearing via passage 20× through a 22 G needle, then freeze-thaw 3× (liquid N2/37° C.), and centrifugation (14,000×g) for 15 min before extracting the supernatant. Duplex or ~3 kb plasmid (~150 ng) was incubated with lysate at 1:3 DNA:lysate volume ratio up to 45 min at 37° C., followed by polyacrylamide gel electrophoresis (PAGE), and ethidium bromide (EtBr) gel staining for 30 min before UV detection of DNA bands.

Example 34

HerDox—In Vivo Procedures

IACUC-approval was obtained for all in vivo and euthanasia procedures in this study. Female immunodeficient (nu/nu) mice (6-8 weeks; Charles River Laboratories International, Wilmington, Mass., USA) received subcutaneous bilateral flank injections of 1×107 indicated cells and monitored until tumors reached ~200-300 mm3, at which point the following treatments were initiated. To assess tumor-targeting in vivo, tumor-bearing mice received a single i.v. (via tail vein)-injection of HerDox or Dox (0.02 mg/kg final Dox dose) and imaged at the indicated time points after injection using a custom small animal imager adjusted to detect Dox fluorescence. After the final time point, mice were euthanized, and tissues harvested for biodistribution analysis. To assess pharmacokinetics, separate groups of tumor-bearing mice receiving a single i.v. injection of HerDox were euthanized at the indicated time points and tissues harvested for fluorescence acquisition using the same custom imager described below. To assess therapeutic efficacy, a new group of tumor-bearing mice received daily i.v. (tail vein) injections of HerDox or Dox at indicated doses for 7 days followed by continued monitoring of tumor volumes (assessed by measuring tumor length and width using calipers, and applying L×W2), animal weights, and heart function. Feasibility of repeated injections in the tail vein was demonstrated. Cardiac function in anesthetized mice was evaluated by a Vevo 770 High-Frequency Ultrasound system (VisualSonics, Toronto, Canada). Heart rate and body temperature were monitored. Superficial hair was removed from the region of interest with a depilatory cream (Nair) before imaging. The 2-dimensional guided M-mode images of the left ventricle were obtained in the short-axis view at the papillary level with the mouse in the supine position. All primary measurements were traced manually and digitized by goal-directed software installed within the echocardiograph. Three beats were averaged for each measurement. All measurements were done from leading edge to leading edge according to the American Society of Echocardiography guidelines. At animal study completion, tissue harvested from euthanized mice were fixed in 4% paraformaldehyde/PBS at 4° C. for 24 h followed by transfer into 20% sucrose/PBS and storage at −80° C. before immunohistochemical processing. Specimens and hematoxylin/eosin staining were prepared by AML Laboratories, Inc., Baltimore, Md., USA.

Example 35

HerDox—In Vivo Imaging

A customized macro-illumination and detection system [35-37] was used for in vivo and tissue imaging. Dox was excited with the 488 nm line of a Coherent Innova ArKr laser. Laser light (300 mW) was directed into a light-tight box via mirrors and expanded by an engineered circular tophat diffuser (Thorlabs ED1-C20) to a uniform circular beam of approximately 15 cm in diameter. The incidence angle to the vertical plane was approximately 150. Fluorescence light was collected via a telecentric lens (Melles-Griot 59LGG925 base lens with a 59LGL428 attachment lens) that can operate at f/#2, has a magnification of 0.9, working distance of 257 mm and a depth of field of 81.5 mm. A bandpass filter (580 nm with a 50 nm bandwidth) was used in the emission pathway to reject the excitation light. Images showing FI were collected with a cooled CCD camera (Hamamatsu ORCA-ER). Where indicated, a Maestro imager was used (Cedars-Sinai Imaging Core Facility). ImageJ was used to calculate average fluorescence intensities of the overall region of each selected tissue.

Example 36

HerDox—TUNEL Staining and Confocal Fluorescence Imaging of Tissue Sections

Fixed, sectioned tissues were processed by incubation in a dry 60° C. oven for 1 h followed by sequential submersion in xylenes for 4 min×5, then hydration in 100%, 95%, 90%, 80%, 70% ethanol for 3 min, 2 times each and final submersion in water. After Proteinase K (20 ug/ml in 10 mM Tris pH 7.8) incubation and rinsing in PBS, sections were treated for TUNEL staining following the manufacturer's instructions (XXX) and assessed by confocal fluorescence imaging. Here, 10 TUNEL images at different locations per tissue were acquired using a Leica confocal SPE microscope (20×, ex: 488 nm, and em: 530 nm). Central regions of each tissue were imaged to avoid fixation artifacts. Nuclear fluorescence intensities, reflective of DNA fragmentation, were measured and averaged using ImageJ.

Example 37

HerDox—Statistical Analyses

All data are expressed as mean±standard deviation of indicated sample sizes, and were analyzed by a one-way ANOVA test followed by a Tukey post-hoc analysis, with the level of significance set at P=0.05.

Example 38

HerDox Results—Particle Assembly Facilitates Serum Stability

Formation of a double-stranded oligonucleotide duplex (dsoligo) by annealing complementary nucleic acid sequences enabled Dox intercalation to form DNA-Dox, which remained intact during ultrafiltration to separate bound from unbound Dox. Whereas free Dox passed through the filter membrane and was detectable in the filtrate, Dox was nearly undetectable in DNA-Dox filtrates, even with subsequent washes to remove any free/released Dox. In agreement, the maximum absorbance wavelength ($\lambda$max) of DNA-Dox retentate coincided with unfiltered Dox (with the DNA binding slightly shifting the $\lambda$max), whereas no such absorbance was detectable in the filtrate. Incubating the retentate with HerPBK10 formed the product, HerDox, in which the majority of Dox absorbance detected during size exclusion HPLC co-eluted with HerPBK10. Electrophoretic mobility shift analysis confirmed that Her-PBK10 directly bound the DNA duplex. CryoEM imaging showed that HerDox formed mostly round ~10 nm diameter particles in addition to some larger amorphous aggregates. Storage at different incubation times and temperatures (4° C., RT, or 37° C. over a 12 day period) yielded no detectable Dox release from HerDox.

To predict stability in vivo, ultrafiltration was used to determine whether incubation in blood induced Dox release from the complex, which would be detected by a partitioning of Dox fluorescence into the filtrates (as exhibited by free Dox after a 1 h incubation at 37° C. in freshly collected blood from mice). In contrast to free Dox, HerDox showed no detectable fluorescence in filtrates nor loss from retentates, suggesting that the complex retains Dox even in blood. In agreement, HerDox incubated up to 24 h in complete cell culture media exhibited no loss of Dox from the complex, suggesting that HerDox retains stability under physiological conditions.

To identify the factors contributing to serum-stability, we first examined ds-oligo vulnerability to degradation by serum nucleases. Naked duplex in mouse serum underwent degradation within 20 min of exposure while pre-assembly with HerPBK10 or heat-inactivation (HI) of the serum prevented this, suggesting that HerPBK10 binding protects the duplex from serum-mediated degradation. Pre-intercalation by Dox also partially protected the DNA from serum degradation, thus preventing its own release in serum. To validate these findings, we subjected HerDox and controls to ultrafiltration after serum exposure and assessed the level of Dox loss from retentates. The majority (~70%) of free Dox was lost from Dox-only retentates whereas no Dox loss was detected from HerDox or DNA-Dox retentates. An assessment of serum-binding activity suggests that the remaining ~30% of free Dox is likely to undergo relatively weak or non-specific binding to serum proteins. Consistent with the gel assays, Dox retention in serum-exposed DNA-Dox suggested that this complex was equally resistant as HerDox to serum nucleases and/or Dox loss. Altogether, these findings indicate that both HerPBK10 binding and Dox intercalation protects the DNA from serum-mediated degradation, which in turns prevents serum-mediated Dox release from HerDox.

Example 39

HerDox Results—HerDox Toxicity In Vitro is Targeted to HER2+ Cells and Correlates with HER2 Subunit Levels HerDox induced significant toxicity to HER2+ (MDA-MB-435) but not HER2-(MDA-MB-231) human breast cancer cells in separate cell cultures, whereas Dox exhibited no preference, and HerPBK10 alone had no effect on proliferation or survival of either cell line. The competitive inhibitor, eHRG, prevented HER2+ cell killing by HerDox, suggesting that HerDox bound and entered cells via the heregulin receptor, HER.

To assess the contribution of HER2 to therapeutic efficacy in vitro, we determined HerDox CD50 on selected human tumor lines displaying HER2 at relatively high (SKBR3), moderate (MDA-MB-435, MDAMB-453, HeLa), and low to undetectable (MDA-MB-231) levels, according to our receptor subunit profiling of a cell line panel. In support of the influence of HER2 on ligand-receptor affinity, HerDox CD50 on selected lines inversely correlated with cell surface HER2 on high (SKBR3, 0.056±0.017 uM) and low HER2 cell lines (MDA-MB-231, >8 uM), while intermediate sensitivities associated with intermediate HER2 levels (0.3-0.8 uM); note CD50 is shown on a log scale).

To confirm selectivity for HER2+ cells and add a further targeting challenge, HerDox was added to HER2+ and HER2− co-cultured breast cancer cells, distinguished from one another by green fluorescent protein (GFP)-tagging of the HER2− cell line, as described previously. While Dox alone exhibited reduced efficacy on a mixed cell culture, HerDox substantially reduced HER2+ but not HER2− cell growth.

Finally, the inventors examined cytotoxicity to HER2+ glioma cells. In vivo, glioma require invasive localized procedures that necessitate high efficacy at low treatment frequency while still benefiting from the tumor retention aspects of targeting. Taking this requirement into consideration, we exposed U251 human glioma cells in vitro (which display higher surface HER2 and similar surface HER3/4 subunit levels compared to MDA-MB-435 cells) to a single dose of HerDox in vitro, which induced nearly complete cell death while an equivalent dose of Dox alone was less effective (75-80% cell death by Dox in comparison to 96-99% cell death by HerDox). Cell death prevention by eHRG confirmed receptor specific delivery by HerDox. Notably, the sensitivity of this tumor line to a single dose is consistent with the earlier CD50 studies showing that high HER2 expression correlates with lower required dosage for therapeutic efficacy.

Example 40

HerDox Results—Dox is Released after Cell Uptake

A microscopic examination of treated MDA-MB-435 cells showed that while untargeted Dox was detectable at the nuclear periphery immediately after administration (consistent with its ability to permeate the plasma membrane and target the nucleus), HerDox appeared mostly at the cell periphery early after administration and exhibited nuclear accumulation by 60 min, consistent with a cell entry mechanism that relies on initial binding at the cell surface. In further contrast, HerDox showed a nucleolar and cytosolic accumulation in live cells in comparison to the typical nuclear accumulation of untargeted Dox. The ability to visualize nuclear Dox fluorescence after cell exposure to free Dox has been used frequently to detect Dox uptake in cells, and has been attributed to interaction with histones. To determine whether these localization differences indicate that Dox remains attached to HerPBK10 during uptake, the inventors used a counterstain for HerPBK10. At 15 min of uptake, HerPBK10 mostly colocalized with Dox, suggesting that a considerable population of HerDox is still intact, though some nuclear accumulation of Dox is already visible. At 30 and 60 min, increasing levels of Dox accumulated in the nucleus while the majority of HerPBK10 remained in the cytoplasm, suggesting that Dox is released from HerPBK10 after uptake.

To test whether intracellular Dox release is facilitated by cytosolic nuclease degradation of the DNA, the inventors assessed the vulnerability of ds-oligo to cytosolic lysates, and observed that whereas a control plasmid underwent DNA nicking, the duplex remained undigested (FIG. 5D). These findings suggest that post-entry Dox separation from HerPBK10 occurs through a nuclease-free displacement mechanism. Hence, there is a possibility that Dox is still bound to the ds-oligo during nuclear entry.

Example 41

HerDox Results—HerDox Targets HER2+ Tumor Cells In Vivo

MDA-MB-435 tumor-bearing mice were imaged live after a single tail vein injection of HerDox, in order to visualize tumor-targeting ability in vivo. The imaging showed tumor-accumulation of HerDox by 20 min, where it remained detectable up to 100 min. The maximum fluorescence intensity (FI) measured in tissues harvested at ~3 h after injection showed that HerDox exhibited preferential tumor accumulation compared to other tissue: liver and kidney FIs were 45% and 65% lower than tumors, respectively, while the heart, spleen, lungs, and skeletal muscle, exhibited no detectable fluorescence. In contrast, Dox exhibited higher accumulation in all other non-tumor tissues compared to HerDox while tumor-accumulation was nearly 50% lower than HerDox and equated liver and kidney FIs. Pharmacokinetics studies suggested that HerDox underwent rapid kidney entry by 10 min that decreased over time whereas tumor-preferential accumulation continued to increase within 40 min and remained considerably higher (500-1000 fluorescence units higher/tissue) up to 24 h compared to normal tissue (heart, liver, muscle, spleen, lung, and kidneys). This pattern contrasted with that observed in mice receiving untargeted Dox, which showed no preferential accumulation of Dox in tumors over other tissue, while tumor accumulated Dox was substantially lower (by 1000 fluorescence units) compared to HerDox. As an additional comparison, HerDox and Dox were delivered i.v. in mice bearing U87 human glioma tumors, which display ~50% lower level of HER subunits compared to MDA-MB-435 cells. In these mice, HerDox delivery to U87 tumors was ~50% lower with reduced contrast between tumor and normal (i.e. kidney, liver) tissue compared to MDA-MB-435 tumor-bearing mice. Non-targeted Dox distribution to non-tumor tissue in these mice was similar to that in the MDA-MB-435 tumor-bearing mice, while delivery to the tumors was actually slightly higher (200-300 fluorescence units per tissue). Altogether, these findings indicate that HerDox preferentially accumulates in HER2+ tumors over non-tumor tissue, and over tumors expressing lower HER levels.

Example 42

HerDox Results—HerDox Ablates Tumor Growth and is Nontoxic to the Heart

To assess therapeutic efficacy in vivo, MDA-MB-435 tumor-bearing mice received daily i.v. injections of HerDox for seven days while tumor volumes were measured after administration. HerDox treatment resulted in ablation of tumor growth, which contrasted with the low efficacy by the equivalent Dox dose, while HerPBK10 alone and saline had no effect on tumor growth. Importantly, 10× higher Dox dose was required to approach the tumor ablation of HerDox, but was still slightly less effective. Mice did not experience detectable weight loss, suggesting that treatments did not affect general health, however echocardiography showed signs of Dox induced cardiac dysfunction that is not detectable in HerDox-treated mice: whereas Dox induced modest to marked reductions in stroke volume, cardiac output, and left ventricular internal dimension and volume, HerDox had no effect on these measurements, which appeared similar to mock (saline)-treated mice. Myocardia from both saline and HerDox-treated mice exhibited normal cardiac morphology, whereas those from Dox-treated mice exhibited myofibrillar degeneration, typifying Dox-induced cardiotoxicity. Whereas in vivo imaging showed that residual levels of HerDox accumulated in the liver and kidney, TUNEL staining of both organs showed that Dox induced marked apoptosis in the liver whereas HerDox did not. Neither Dox nor HerDox showed substantial apoptosis in the kidney.

Example 43

HerDox—Conclusions

The targeted particle tested here avoids peripheral tissue damage while enabling lower drug dose for tumor killing, presenting both therapeutic and safety advantages over the untargeted drug. Delivery of a long established, FDA-approved chemotherapeutic may assist progress toward clinical trials. The lack of covalent modification while retaining stability allows doxorubicin potency to remain unaltered during assembly, transport, and release into target cells, thus presenting an advantage over chemical conjugates. The HER2+ cell targeting shown here avoids the cardiotoxicity associated with anthracyclines and HER2-targeted antibodies, and may provide an alternative treatment for HER2+ tumors that have accumulated signal-pathway mutations and are therefore non-responsive to signal-blocking antibodies. Re-targeting via ligand replacement has the potential to target other tumors. Altogether, these studies provide the groundwork for building an optimized tumor-targeted particle that may be expanded into the facile combination of different types of DNA-binding drugs with carrier molecules similar to HerPBK10, but designed to target different types of cancers.

The targeted particle tested here avoids peripheral tissue damage while enabling lower drug dose for tumor killing, presenting both therapeutic and safety advantages over the untargeted drug.

The lack of covalent modification while retaining stability allows doxorubicin potency to remain unaltered during assembly, transport, and release into target cells, thus presenting an advantage over chemical conjugates.

The HER2+ cell targeting shown here avoids the cardiotoxicity associated with anthracyclines and HER2-targeted antibodies.

Example 43

HerDox—Summary Points

Particle assembly facilitates serum-stability:
Both electrophilic and intercalation interactions that mediate HerDox self-assembly into ~10 nm diameter round nanoparticles also independently facilitate its serum-stability.

HerDox toxicity in vitro is targeted to HER2+ cells and correlates with HER2 subunit levels:
  HerDox exhibits receptor-dependent cell targeting and uptake in several different human HER2+ tumor cells, including breast cancer, cervical carcinoma, and glioma cells, and specifically ablates HER2+ cells in a heterogeneous cell culture.
  Dox is released after cell uptake:
  Dox is released from the nanoparticle intracellularly by a nuclease-independent mechanism and accumulates in nucleoli whereas the untargeted drug remains throughout the nucleus, suggesting that the nucleic acid in HerDox influences the final destination of the drug.
  HerDox targets HER2+ tumor cells in vivo:
  Systemic delivery of HerDox in a preclinical model results in tumor-preferential delivery in comparison to the untargeted drug, which exhibits higher delivery to off-target tissue.
  In vivo tumor targeting is concomitant with receptor level and exhibits considerable tumor retention by 24 h after delivery compared to untargeted Dox.
  HerDox elicits tumor-targeted growth ablation while sparing off-target tissue:
  HerDox ablates tumors at >10× lower dose compared to untargeted doxorubicin while sparing the heart after intravenous delivery.
  Hearts of HerDox-treated mice show no cardiac dysfunction or histological damage in contrast to the myocardial damage induced by the untargeted drug.
  Livers of HerDox-treated mice showed negligible apoptosis in contrast to livers from Dox-treated mice.

While the description above refers to particular embodiments of the present invention, it should be readily apparent to people of ordinary skill in the art that a number of modifications may be made without departing from the spirit thereof. The presently disclosed embodiments are, therefore, to be considered in all respects as illustrative and not restrictive. One skilled in the art will recognize many methods and materials similar or equivalent to those described herein, which could be used in the practice of the present invention. Indeed, the present invention is in no way limited to the methods and materials described. For example, various agents may be delivered in conjunction with embodiments described herein and the invention should not be merely limited to siRNA. Similarly, various motifs could be used interchangeably with or in addition to those described herein and the invention should not be construed as limited to only polylysine motifs and/or RGD motifs. Finally, as recognized by one of skill in the art, the invention can be applied to any number of conditions, disorders and/or diseases where it is advantageous to target delivery of an agent to a cell and/or cell nucleus and the present invention should not be construed in any way as limited to the treatment of breast cancer.

Various embodiments of the invention are described above in the Description of the Invention. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventor that the words and phrases in the specification and claims be given the ordinary and accustomed meanings to those of ordinary skill in the applicable art(s).

The foregoing description of various embodiments of the invention known to the applicant at this time of filing the application has been presented and is intended for the purposes of illustration and description. The present description is not intended to be exhaustive nor limit the invention to the precise form disclosed and many modifications and variations are possible in the light of the above teachings. The embodiments described serve to explain the principles of the invention and its practical application and to enable others skilled in the art to utilize the invention in various embodiments and with various modifications as are suited to the particular use contemplated. Therefore, it is intended that the invention not be limited to the particular embodiments disclosed for carrying out the invention.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention. Furthermore, it is to be understood that the invention is solely defined by the appended claims. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations).

Accordingly, the invention is not limited except as by the appended claims.

REFERENCES

Agadjanian, H., Weaver, J. J., Mahammed, A., Rentsendorj, A., Bass, S., Kim, J., Dmochowski, I. J., Margalit, R., Gray, H. B., Gross, Z., et al. (2006). Specific delivery of corroles to cells via noncovalent conjugates with viral proteins. Pharm Res 23, 367-377. Epub 2006 January 2019.

Baselga, J., Tripathy, D., Medndelsohn, J., Baughman, S., Benz, C. C., Dantis, L., Sklarin, N. T., Seidman, A. D., Hudis, C. A., Moore, J., et al. (1996). Phase II study of weekly intravenous recombinant humanized anti-p185$^{HER2}$ monoclonal antibody in patients with HER2/neu-overexpressing metastatic breast cancer. J Clin Oncol 14, 737-744.

Braslawsky, G. R., Edson, M. A., Pearce, W., Kaneko, T., and Greenfield, R. S. (1990). Antitumor activity of adriamycin (hydrazone-linked) immunoconjugates compared with free adriamycin and specificity of tumor cell killing. Cancer Res 50, 6608-6614.

Chester, K. A., Bhatia, J., Boxer, G., Cooke, S. P., Flynn, A. A., Huhalov, A., Mayer, A., Pedley, R. B., Robson, L., Sharma, S. K., et al. (2000). Clinical applications of phage-derived sFvs and sFv fusion proteins. Disease Markers 16, 53-62.

Choudhury, A., Charo, J., Parapuram, S. K., Hunt, R. C., Hunt, D. M., Seliger, B., and Kiessling, R. (2004). Small interfering RNA (siRNA) inhibits the expression of the Her2/neu gene, upregulates HLA class I and induces apoptosis of Her2/neu positive tumor cell lines. International Journal of Cancer 108, 71-77.

Cobleigh, M. A., Vogel, C. L., Tripathy, D., Robert, N. J. S., S., Fehrenbacher, L., Paton, V., Shak, S., Leiberman, G., and Slamon, D. (1998). Efficacy and safety of Herceptin (Humanized anti-HER2 antibody) as a single agent in 222 women with HER2 overexpression who relapsed following chemotherapy for metastatic breast cancer. Proc Am Soc Clin Oncol 17, 97a.

Drummond, D. C., Meyer, O., Hong, K., Kirpotin, D. B., and Papahadjopoulos, D. (1999). Optimizing liposomes for delivery of chemotherapeutic agents to solid tumors. Pharmacol Rev 51, 691-743.

Faltus, T., Yuan, J., Zimmer, B., Kramer, A., Loibl, S., Kaufmann, M., and Strebhardt, K. (2004). Silencing of the HER2/neu gene by siRNA inhibits proliferation and induces apoptosis in HER2/neu-overexpressing breast cancer cells. Neoplasia 6, 786-795.

Fisher, K. J., and Wilson, J. M. (1997). The transmembrane domain of diphtheria toxin improves molecular conjugate gene transfer. Biochemical Journal 321, 49-58.

Frankel, A. E., Kreitman, R. J., and Sausville, E. A. (2000). Targeted toxins. Clinical Cancer Research 6, 326-334.

Glockshuber, R., Malia, M., Pfitzinger, I., and Pluckthun, A. (1990). A comparison of strategies to stabilize immunoglobulin Fv-fragments. Biochemistry 29, 1362-1367.

Goren, D., Horowitz, A. T., Zalipsky, S., Woodle, M. C., Yarden, Y., and Gabizon, A. (1996). Targeting of stealth liposomes to erbB-2 (Her/2) receptor: in vitro and in vivo studies. Br J Cancer 74, 1749-1756.

Jeschke, M., Wels, W., Dengler, W., Imber, R., Stocklin, E., and Groner, B. (1995). Targeted inhibition of tumor-cell growth by recombinant heregulin-toxin fusion proteins. International Journal of Cancer 60, 730-739.

Kim, D.-H., Longo, M., Han, Y., Lundberg, P., Cantin, E., and Rossi, J. J. (2004). Interferon induction by siRNAs and ssRNAs synthesized by phage polymerase. Nature Biotechnology 22, 321-325.

Kute, T., Lack, C. M., Willingham, M., Bishwokama, B., Williams, H., Barrett, K., Mitchell, T., and Vaughn, J. P. (2004). Development of Herceptin resistance in breast cancer cells. Cytometry A 57, 86-93.

Medina-Kauwe, L. K., and Chen, X. (2002). Using GFP-Ligand Fusions to Measure Receptor-Mediated Endocytosis in Living Cells. In Vitamins and Hormones, G. Litwack, ed. (San Diego, Elsevier Science), pp. 81-95.

Medina-Kauwe, L. K., Kasahara, N., and Kedes, L. (2001a). 3PO, a novel non-viral gene delivery system using engineered Ad5 penton proteins. Gene Therapy 8, 795-803.

Medina-Kauwe, L. K., Leung, V., Wu, L., and Kedes, L. (2000). Assessing the Binding and Endocytosis Activity of Cellular Receptors Using GFP-Ligand Fusions. BioTechniques 29, 602-609.

Medina-Kauwe, L. K., Maguire, M., Kasahara, N., and Kedes, L. (2001b). Non-viral gene delivery to human breast cancer cells by targeted Ad5 penton proteins. Gene Therapy 8, 1753-1761.

Medina-Kauwe, L. K., Xie, J., and Hamm-Alvarez, S. (2005). Intracellular trafficking of nonviral vectors. Gene Ther 12, 1734-1751.

Minotti, G., Menna, P., Salvatorelli, E., Cairo, G., and Gianni, L. (2004). Anthracyclines: molecular advances and pharmacologic developments in antitumor activity and cardiotoxicity. Pharmacol Rev 56, 185-229.

Park, J. W., Hong, K., Kirpotin, D. B., Colbern, G., Shalaby, R., Baselga, J., Shao, Y., Nielsen, U. B., Marks, J. D., Moore, D., et al. (2002). Anti-HER2 immunoliposomes: enhanced efficacy attributable to targeted delivery. Clin Cancer Res 8, 1172-1181.

Schmidt, M., Maurer-Gebhard, M., Groner, B., Kohler, G., Brochmann-Santos, G., and Wels, W. (1999). Suppression of metastasis formation by a recombinant single chain antibody-toxin targeted to full-length and oncogenic variant EGF receptors. Oncogene 18, 1711-1721.

Slamon, D. J., Leyland-Jones, B., Shak, S., Fuchs, H., Paton, V., Bajamonde, A., Fleming, T., Eiermann, W., Wolter, J., Pegram, M., et al. (2001). Use of chemotherapy plus a monoclonal antibody against HER2 for metastatic breast cancer that overexpresses HER2. N Engl J Med 344, 783-792.

Trail, P. A., King, H. D., and Dubowchik, G. M. (2003). Monoclonal antibody drug immunoconjugates for targeted treatment of cancer. Cancer Immunol Immunother 52, 328-337.

Trail, P. A., Willner, D., Lasch, S. J., Henderson, A. J., Greenfield, R. S., King, D., Zoeckler, M. E., and Braslawsky, G. R. (1992). Antigen-specific activity of carcinoma-reactive BR64-doxorubicin conjugates evaluated in vitro and in human tumor xenograft models. Cancer Res 52, 5693-5700.

Trail, P. A., Willner, D., Lasch, S. J., Henderson, A. J., Hofstead, S., Casazza, A. M., Firestone, R. A., Hellstrom, I., and Hellstrom, K. E. (1993). Cure of xenografted human carcinomas by BR96-doxorubicin immunoconjugates. Science 261, 212-215.

Vogel, C. L., Cobleigh, M. A., Tripathy, D., Gutheil, J. C., Harris, L. N., Fehrenbacher, L., Slamon, D. J., Murphy, M., Novotny, W. F., Burchmore, M., et al. (2002). Efficacy and safety of trastuzumab as a single agent in first-line treatment of HER2-overexpressing metastatic breast cancer. J Clin Oncol 20, 719-726.

Zabner, J., Fasbender, A. J., Moninger, T., Poellinger, K. A., and Welsh, M. J. (1995). Cellular and molecular barriers to gene transfer by a cationic lipid. Journal of Biological Chemistry 270, 18997-19007.

What is claimed is:

1. A treatment delivery platform, comprising:
a polypeptide sequence adapted to target and penetrate a cancer cell, wherein the polypeptide sequence comprises, from N-terminus to C-terminus, a Her segment, a penton base segment, and a decalysine motif, and
a delivery molecule bound to the decalysine motif via electrostatic interactions, wherein the delivery molecule comprises a triphosphate-capped siRNA.

2. The treatment delivery platform of claim 1, wherein the polypeptide sequence comprises SEQ ID NO:5.

3. The treatment delivery platform of claim 1, wherein the siRNA comprises a T7 transcribed siRNA.

4. The treatment delivery platform of claim 1, wherein the siRNA is a HER2 siRNA.

5. The treatment delivery platform of claim 1, wherein the polypeptide sequence comprises a sequence encoded by SEQ ID NO:1.

6. The treatment delivery platform of claim 1, wherein the penton base segment is an adenovirus serotype 5 (Ad5) penton base segment.

7. The treatment delivery platform of claim 1, wherein the cancer cell is a HER+ cancer cell.

8. The treatment delivery platform of claim 1, wherein the cancer cell is a breast cancer cell.

9. A pharmaceutical composition, comprising:
a treatment delivery platform, comprising:
a polypeptide sequence adapted to target and penetrate a cancer cell, wherein the polypeptide sequence comprises, from N-terminus to C-terminus, a Her segment, a penton base segment, and a decalysine motif, and
a delivery molecule bound to the decalysine motif via electrostatic interactions, wherein the delivery molecule comprises a triphosphate-capped siRNA; and
a pharmaceutically acceptable carrier.

10. The pharmaceutical composition of claim 9, wherein the polypeptide sequence comprises a sequence encoded by SEQ ID NO:1.

11. The pharmaceutical composition of claim 9, wherein the siRNA comprises a T7-transcribed siRNA.

12. The pharmaceutical composition of claim 9, wherein the siRNA is a HER2 siRNA.

13. The pharmaceutical composition of claim 9, wherein the polypeptide sequence comprises SEQ ID NO: 5.

14. The pharmaceutical composition of claim 9, wherein the pharmaceutical composition is formulated for parenteral administration.

15. The pharmaceutical composition of claim 9, wherein the pharmaceutical composition is a lyophilized powder.

16. The pharmaceutical composition of claim 9, wherein the penton base segment is an adenovirus serotype 5 (Ad5) penton base segment.

17. The pharmaceutical composition of claim 9, wherein the cancer cell is a HER2+ cancer cell.

18. The pharmaceutical composition of claim 9, wherein the cancer cell is a breast cancer cell.

* * * * *

UNITED STATES PATENT AND TRADEMARK OFFICE
CERTIFICATE OF CORRECTION

PATENT NO. : 10,793,853 B2  
APPLICATION NO. : 13/189265  
DATED : October 6, 2020  
INVENTOR(S) : Lali K. Medina-Kauwe Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 192 days.

Signed and Sealed this  
Sixth Day of December, 2022

Katherine Kelly Vidal  
*Director of the United States Patent and Trademark Office*

SEQUENCE LISTING

<160> NUMBER OF SEQ ID NOS: 9

<210> SEQ ID NO 1
<211> LENGTH: 2382
<212> TYPE: DNA
<213> ORGANISM: Homo sapiens

<400> SEQUENCE: 1

| | | | | | |
|---|---|---|---|---|---|
| ttgcctcccc | gattgaaaga | gatgaaaagc | caggaatcgg | ctgcaggttc | caaactagtc | 60 |
| cttcggtgtg | aaaccagttc | tgaatactcc | tctctcagat | tcaagtggtt | caagaatggg | 120 |
| aatgaattga | atcgaaaaaa | caaaccacaa | aatatcaaga | tacaaaaaaa | gccagggaag | 180 |
| tcagaacttc | gcattaacaa | agcatcactg | gctgattctg | gagagtatat | gtgcaaagtg | 240 |
| atcagcaaat | taggaaatga | cagtgcctct | gccaatatca | ccatcgtgga | atcaaacgag | 300 |
| atcatcactg | gtatgccagc | ctcaactgaa | ggagcatatg | tgtcttcaga | gtctcccatt | 360 |
| agaatatcag | tatccacaga | aggagcaaat | acttcttcat | ctacatctac | atccaccact | 420 |
| gggacaagcc | atcttgtaaa | atgtgcggag | aaggagaaaa | ctttctgtgt | gaatggaggg | 480 |
| gagtgcttca | tggtgaaaga | cctttcaaac | ccctcgagat | acttgtgcaa | gtgccaacct | 540 |
| ggattcactg | gagcaagatg | tactgagaat | gtgcccatga | agtccaaaa | ccaagaaaag | 600 |
| gcggaggagc | tgtacggtgg | aagtggtgga | agtggatcca | tgcggcgcgc | ggcgatgtat | 660 |
| gaggaaggtc | ctcctcccctc | ctacgagagt | gtggtgagcg | cggcgccagt | ggcggcggcg | 720 |
| ctgggttctc | ccttcgatgc | tccccctggac | ccgccgtttg | tgcctccgcg | gtacctgcgg | 780 |
| cctaccgggg | ggagaaacag | catccgttac | tctgagttgg | caccctatt | cgacaccacc | 840 |
| cgtgtgtacc | tggtggacaa | caagtcaacg | gatgtggcat | ccctgaacta | ccagaacgac | 900 |
| cacagcaact | ttctgaccac | ggtcattcaa | aacaatgact | acagcccggg | ggaggcaagc | 960 |
| acacagacca | tcaatcttga | cgaccggtcg | cactggggcg | gcgacctgaa | aaccatcctg | 1020 |
| cataccaaca | tgccaaatgt | gaacgagttc | atgtttacca | ataagtttaa | ggcgcgggtg | 1080 |
| atggtgtcgc | gcttgcctac | taaggacaat | caggtggagc | tgaaatacga | gtgggtggag | 1140 |
| ttcacgctgc | ccgagggcaa | ctactccgag | accatgacca | tagaccttat | gaacaacgcg | 1200 |
| atcgtggagc | actacttgaa | agtgggcaga | cagaacgggg | ttctggaaag | cgacatcggg | 1260 |
| gtaaagtttg | acacccgcaa | cttcagactg | gggtttgacc | ccgtcactgg | tcttgtcatg | 1320 |
| cctggggtat | atacaaacga | agccttccat | ccagacatca | ttttgctgcc | aggatgcggg | 1380 |
| gtggacttca | cccacagccg | cctgagcaac | ttgttgggca | tccgcaagcg | gcaacccttc | 1440 |
| caggagggct | ttaggatcac | ctacgatgat | ctggagggtg | gtaacattcc | cgcactgttg | 1500 |
| gatgtggacg | cctaccaggc | gagcttgaaa | gatgacaccg | aacagggcgg | gggtggcgca | 1560 |
| ggcggcagca | acagcagtgg | cagcggcgcg | gaagagaact | ccaacgcggc | agccgcggca | 1620 |
| atgcagccgg | tggaggacat | gaacgatcat | gccattcgcg | gcgacacctt | tgccacacgg | 1680 |
| gctgaggaga | agcgcgctga | ggccgaagca | gcggccgaag | ctgccgcccc | cgctgcgcaa | 1740 |
| cccgaggtcg | agaagcctca | gaagaaaccg | gtgatcaaac | cctgacagaa | ggacagcaag | 1800 |
| aaacgcagtt | acaacctaat | aagcaatgac | agcaccttca | cccagtaccg | cagctggtac | 1860 |
| cttgcataca | actacggcga | ccctcagacc | ggaatccgct | catggaccct | gctttgcact | 1920 |
| cctgacgtaa | cctgcggctc | ggagcaggtc | tactggtcgt | tgccagacat | gatgcaagac | 1980 |
| cccgtgacct | tccgctccac | gcgccagatc | agcaactttc | cggtggtggg | cgccgagctg | 2040 |
| ttgcccgtgc | actccaagag | cttctacaac | gaccaggccg | tctactccca | actcatccgc | 2100 |

-continued

```
cagtttacct ctctgaccca cgtgttcaat cgctttcccg agaaccagat tttggcgcgc    2160
ccgccagccc ccaccatcac caccgtcagt gaaaacgttc ctgctctcac agatcacggg    2220
acgctaccgc tgcgcaacag catcggagga gtccagcgag tgaccattac tgacgccaga    2280
cgccgcacct gccccctacgt ttacaaggcc ctgggcatag tctcgccgcg cgtcctatcg    2340
agccgcactt ttaaaaaaaa aaaaaaaaaa aaaaaaaaaa aa                        2382
```

<210> SEQ ID NO 2
<211> LENGTH: 33
<212> TYPE: DNA
<213> ORGANISM: Homo sapiens

<400> SEQUENCE: 2

```
gcatcagaat tctcaaaaag tgcggctcga tag                                 33
```

<210> SEQ ID NO 3
<211> LENGTH: 63
<212> TYPE: DNA
<213> ORGANISM: Homo sapiens

<400> SEQUENCE: 3

```
catgaattca tttttttttt tttttttttt tttaaaagtg cggctcgata              60
gga                                                                  63
```

<210> SEQ ID NO 4
<211> LENGTH: 66
<212> TYPE: DNA
<213> ORGANISM: Homo sapiens

<400> SEQUENCE: 4

```
atgaattcat tttttttttt tttttttttt tttttttttt ttagatctac ttccaccact    60
tccacc                                                               66
```

<210> SEQ ID NO 5
<211> LENGTH: 571
<212> TYPE: PRT
<213> ORGANISM: Homo sapiens

<400> SEQUENCE: 5

Met Arg Arg Ala Ala Met Tyr Glu Glu Gly Pro Pro Ser Tyr Glu
1               5                   10                  15

Ser Val Val Ser Ala Ala Pro Val Ala Ala Ala Leu Gly Ser Pro Phe
            20                  25                  30

Asp Ala Pro Leu Asp Pro Pro Phe Val Pro Pro Arg Tyr Leu Arg Pro
        35                  40                  45

Thr Gly Gly Arg Asn Ser Ile Arg Tyr Ser Glu Leu Ala Pro Leu Phe
    50                  55                  60

Asp Thr Thr Arg Val Tyr Leu Val Asp Asn Lys Ser Thr Asp Val Ala
65                  70                  75                  80

Ser Leu Asn Tyr Gln Asn Asp His Ser Asn Phe Leu Thr Thr Val Ile
                85                  90                  95

Gln Asn Asn Asp Tyr Ser Pro Gly Glu Ala Ser Gln Thr Ile Asn
            100                 105                 110

Leu Asp Asp Arg Ser His Trp Gly Gly Asp Leu Lys Thr Ile Leu His
        115                 120                 125

Thr Asn Met Pro Asn Val Asn Glu Phe Met Phe Thr Asn Lys Phe Lys
    130                 135                 140

-continued

```
Ala Arg Val Met Val Ser Arg Leu Pro Thr Lys Asp Asn Gln Val Glu
145                 150                 155                 160

Leu Lys Tyr Glu Trp Val Glu Phe Thr Leu Pro Glu Gly Asn Tyr Ser
                165                 170                 175

Glu Thr Met Thr Ile Asp Leu Met Asn Asn Ala Ile Val Glu His Tyr
            180                 185                 190

Leu Lys Val Gly Arg Gln Asn Gly Val Leu Glu Ser Asp Ile Gly Val
            195                 200                 205

Lys Phe Asp Thr Arg Asn Phe Arg Leu Gly Phe Asp Pro Val Thr Gly
            210                 215                 220

Leu Val Met Pro Gly Val Tyr Thr Asn Glu Ala Phe His Pro Asp Ile
225                 230                 235                 240

Ile Leu Leu Pro Gly Cys Gly Val Asp Phe Thr His Ser Arg Leu Ser
                245                 250                 255

Asn Leu Leu Gly Ile Arg Lys Arg Gln Pro Phe Gln Glu Gly Phe Arg
            260                 265                 270

Ile Thr Tyr Asp Asp Leu Glu Gly Gly Asn Ile Pro Ala Leu Leu Asp
            275                 280                 285

Val Asp Ala Tyr Gln Ala Ser Leu Lys Asp Asp Thr Glu Gln Gly Gly
            290                 295                 300

Gly Gly Ala Gly Gly Ser Asn Ser Ser Gly Ser Gly Ala Glu Glu Asn
305                 310                 315                 320

Ser Asn Ala Ala Ala Ala Met Gln Pro Val Glu Asp Met Asn Asp
            325                 330                 335

His Ala Ile Arg Gly Asp Thr Phe Ala Thr Arg Ala Glu Glu Lys Arg
            340                 345                 350

Ala Glu Ala Glu Ala Ala Glu Ala Ala Pro Ala Ala Gln Pro
            355                 360                 365

Glu Val Glu Lys Pro Gln Lys Lys Pro Val Ile Lys Pro Leu Thr Glu
            370                 375                 380

Asp Ser Lys Lys Arg Ser Tyr Asn Leu Ile Ser Asn Asp Ser Thr Phe
385                 390                 395                 400

Thr Gln Tyr Arg Ser Trp Tyr Leu Ala Tyr Asn Tyr Gly Asp Pro Gln
                405                 410                 415

Thr Gly Ile Arg Ser Trp Thr Leu Leu Cys Thr Pro Asp Val Thr Cys
                420                 425                 430

Gly Ser Glu Gln Val Tyr Trp Ser Leu Pro Asp Met Met Gln Asp Pro
            435                 440                 445

Val Thr Phe Arg Ser Thr Arg Gln Ile Ser Asn Phe Pro Val Val Gly
            450                 455                 460

Ala Glu Leu Leu Pro Val His Ser Lys Ser Phe Tyr Asn Asp Gln Ala
465                 470                 475                 480

Val Tyr Ser Gln Leu Ile Arg Gln Phe Thr Ser Leu Thr His Val Phe
                485                 490                 495

Asn Arg Phe Pro Glu Asn Gln Ile Leu Ala Arg Pro Pro Ala Pro Thr
                500                 505                 510

Ile Thr Thr Val Ser Glu Asn Val Pro Ala Leu Thr Asp His Gly Thr
            515                 520                 525

Leu Pro Leu Arg Asn Ser Ile Gly Gly Val Gln Arg Val Thr Ile Thr
            530                 535                 540

Asp Ala Arg Arg Arg Thr Cys Pro Tyr Val Tyr Lys Ala Leu Gly Ile
545                 550                 555                 560
```

```
Val Ser Pro Arg Val Leu Ser Ser Arg Thr Phe
            565                 570

<210> SEQ ID NO 6
<211> LENGTH: 20
<212> TYPE: DNA
<213> ORGANISM: Artificial Sequence
<220> FEATURE:
<223> OTHER INFORMATION: ErbB2 RTF primer

<400> SEQUENCE: 6
tctggacgtg ccagtgtgaa                                              20

<210> SEQ ID NO 7
<211> LENGTH: 20
<212> TYPE: DNA
<213> ORGANISM: Artificial Sequence
<220> FEATURE:
<223> OTHER INFORMATION: ErbB2 RTR primer

<400> SEQUENCE: 7
tgctccctga ggacacatca                                              20

<210> SEQ ID NO 8
<211> LENGTH: 47
<212> TYPE: DNA
<213> ORGANISM: Artificial Sequence
<220> FEATURE:
<223> OTHER INFORMATION: BglIIHis-5

<400> SEQUENCE: 8
actacagatc tcatcatcat catcatcatg agctcaagca ggaattc                47

<210> SEQ ID NO 9
<211> LENGTH: 30
<212> TYPE: DNA
<213> ORGANISM: Artificial Sequence
<220> FEATURE:
<223> OTHER INFORMATION: LLAA-5

<400> SEQUENCE: 9
cgcctgagca acgcggcggg catccgcaag                                   30
```